(12) United States Patent
Sadeghi et al.

(10) Patent No.: US 11,286,251 B2
(45) Date of Patent: Mar. 29, 2022

(54) MATRIX METALLOPROTEINASE INHIBITORS AND IMAGING AGENTS, AND METHODS USING SAME

(71) Applicants: Yale University, New Haven, CT (US); The United States of America as represented by the Department of Veterans Affairs, Washington, DC (US)

(72) Inventors: Mehran Sadeghi, Bethany, CT (US); Yunpeng Ye, Staten Island, NY (US); Hye-Yeong Kim, Hamden, CT (US); Henry(Yiyun) Huang, Madison, CT (US); Jakub Toczek, New Haven, CT (US)

(73) Assignees: YALE UNIVERSITY, New Haven, CT (US); THE UNITED STATES OF AMERICA AS REPRESENTED BY THE DEPARTMENT OF VETERANS AFFAIRS, Washington, DC (US)

(*) Notice: Subject to any disclaimer, the term of this patent is extended or adjusted under 35 U.S.C. 154(b) by 67 days.

(21) Appl. No.: 16/088,868

(22) PCT Filed: Apr. 7, 2017

(86) PCT No.: PCT/US2017/026610
§ 371 (c)(1),
(2) Date: Sep. 27, 2018

(87) PCT Pub. No.: WO2017/177144
PCT Pub. Date: Oct. 12, 2017

(65) Prior Publication Data
US 2020/0283428 A1    Sep. 10, 2020

Related U.S. Application Data

(60) Provisional application No. 62/320,039, filed on Apr. 8, 2016.

(51) Int. Cl.
| | |
|---|---|
| *A61K 51/00* | (2006.01) |
| *A61M 36/14* | (2006.01) |
| *C07D 413/12* | (2006.01) |
| *A61K 51/04* | (2006.01) |
| *C07D 273/01* | (2006.01) |

(52) U.S. Cl.
CPC .......... *C07D 413/12* (2013.01); *A61K 51/044* (2013.01); *C07D 273/01* (2013.01)

(58) Field of Classification Search
None
See application file for complete search history.

(56) References Cited

U.S. PATENT DOCUMENTS 6,281,352 B1 * 8/2001 Xue .................... A61P 19/02
540/451
2015/0023873 A1   1/2015 Sinusas et al.

OTHER PUBLICATIONS

Remington's: the Science and Practice of Pharmacy, Nineteenth Edition, vol. 17, p. 1777.*
International Search Report and Written Opinion for PCT International Application No. PCT/US2017/026610 dated Jul. 20, 2017.
Liu, et al.,"Bifunctional coupling agents for radiolabeling of biomolecules and target-specific delivery of metallic radionuclides," Adv Drug Deliv Rev. 60(12) ,Sep. 2008 ,1347-1370.
Liu, et al.,"Impact of PKM linkers on biodistribution characteristics of the 99mTc-labeled cyclic RGDfK dimer," Bioconjug Chem. 7(6) ,Nov.-Dec. 2006 ,1499-1507.
Parry, et al.,"In vitro and in vivo evaluation of 64Cu-labeled DOTA-linker-bombesin(7-14) analogues containing different amino acid linker moieties," Bioconjug Chem. 18(4) ,Jul.-Aug. 2007 ,1110-1117.
Xue, et al.,"Design and synthesis of cyclic inhibitors of matrix metalloproteinases and TNF-alpha production," J Med Chem. 41(11) ,May 1998 ,1745-1748.

* cited by examiner

*Primary Examiner* — Michael G. Hartley
*Assistant Examiner* — Melissa J Perreira
(74) *Attorney, Agent, or Firm* — Saul Ewing Arnstein & Lehr LLP; Kathryn Doyle; Domingos J. Silva

(57) ABSTRACT

The present invention provides certain compounds, or salts or solvates thereof, which can be used as matrix metalloproteinase-targeted inhibitors or imaging agents.

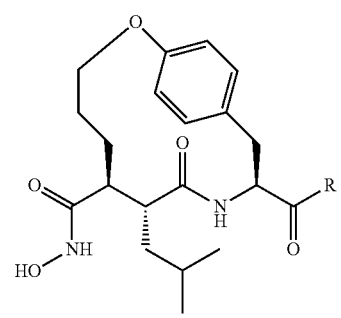

10 Claims, 12 Drawing Sheets

A

B

C

D

MATRIX METALLOPROTEINASE INHIBITORS AND IMAGING AGENTS, AND METHODS USING SAME

CROSS-REFERENCE TO RELATED APPLICATIONS

This application is a 35 U.S.C. § 371 national phase application from, and claims priority to, International Application No. PCT/US2017/026610, filed Apr. 7, 2017, and published under PCT Article 21(2) in English, which claims priority under 35 U.S.C. § 119(e) to U.S. Provisional Patent Application No. 62/320,039, filed Apr. 8, 2016, which are incorporated herein by reference in their entireties.

STATEMENT REGARDING FEDERALLY SPONSORED RESEARCH OR DEVELOPMENT

This invention was made with government support under grants HL112992 and HL114703 awarded by National Institutes of Health, and grant I0-BX001750 awarded by the Department of Veterans Affairs. The government has certain rights in the invention.

BACKGROUND OF THE INVENTION

Matrix metalloproteinases (MMPs) are a family of structurally related zinc-containing enzymes that have the ability to breakdown matrix and other proteins. Upregulation of MMPs is associated with a wide range of diseases, including cancer, as well as pulmonary, musculoskeletal and cardiovascular diseases. MMP inhibitors have thus been proposed as potential therapeutic agents against these diseases. For example, hydroxamate-based MMP inhibitors act by binding to the active site Zn(II) ion in activated MMPs. However, MMP inhibitors as a class of drugs are generally toxic, have debilitating side effects at effective doses (such as musculoskeletal pain or inflammation) and/or exhibit mutagenic properties.

Further, due to the involvement of MMPs in diseases and disorders, there is a high demand for imaging agents that bind to MMPs, helping characterize their expression and/or activation. Such imaging agents would allow physicians to accurately diagnose and treat MMP-associated diseases, such as cardiovascular inflammation. Unfortunately, currently available MMP imaging agents (e.g., $^{99m}$Tc-RP805; FIG. 12, D) exhibit poor target specificity, prolonged blood circulation time, poor stability and/or poor aqueous solubility of their precursors. Such undesired properties limit their utility in clinical applications.

Abdominal aortic aneurysm (AAA) accounts for 10,000-15,000 recorded deaths per year, mainly due to rupture, in the U.S. Current clinical guidelines for surgical repair of AAA are based on aneurysm size, expansion rate and clinical symptoms. However, a significant portion of AAA ruptures occurs in patients who do not meet the criteria for AAA repair, while some large AAA may remain stable for many years. As such, new risk stratification tools are needed to overcome limitations of the current approach to patient selection for AAA repair. Molecular imaging targeted at the determinants of AAA expansion and rupture appears particularly promising in this regard. MMP activation is a main pathophysiological feature of AAA, and is believed to be closely related to aneurysm progression and rupture risk. Thus, molecular imaging of MMP activation can be a useful tool for AAA risk stratification.

There is a need in the art for clinically useful imaging agents that can be used to image MMP activity and/or activation in a patient. There is also a need in the art for compounds that can bind and inhibit MMP activity and/or activation. Such compounds can be used to treat MMP-related diseases and/or evaluate aneurysm (e.g., AAA) progression and rupture risk. The present invention addresses these needs.

BRIEF SUMMARY OF THE INVENTION

The invention provides a compound of formula I, or a salt, solvate, stereoisomer, or tautomer thereof:

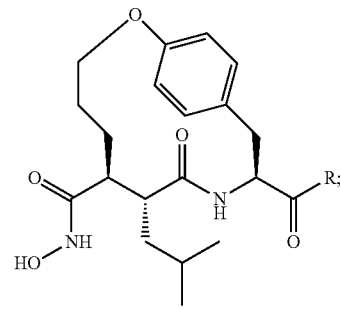

I wherein: R is selected from the group consisting of OH, —NH$_2$, —NHR', —NR'R', —NH(aryl), —NH(heteroaryl) and —NHR$^1$; R$^1$ is selected from the group consisting of:

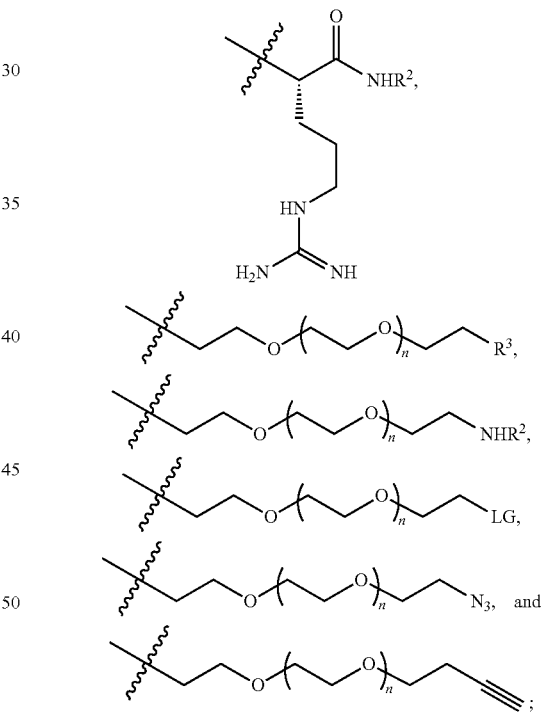

R$^2$ is selected from the group consisting of:

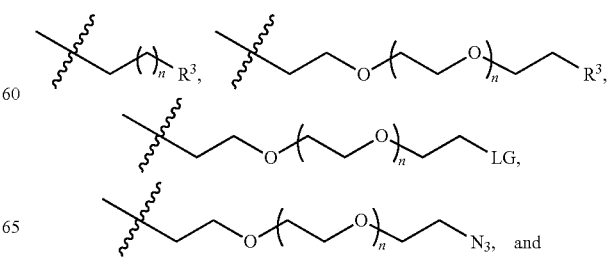

3

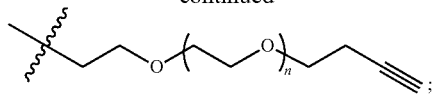

$R^3$ is selected from the group consisting of H, OH, OCH$_3$, F, $^{18}$F,

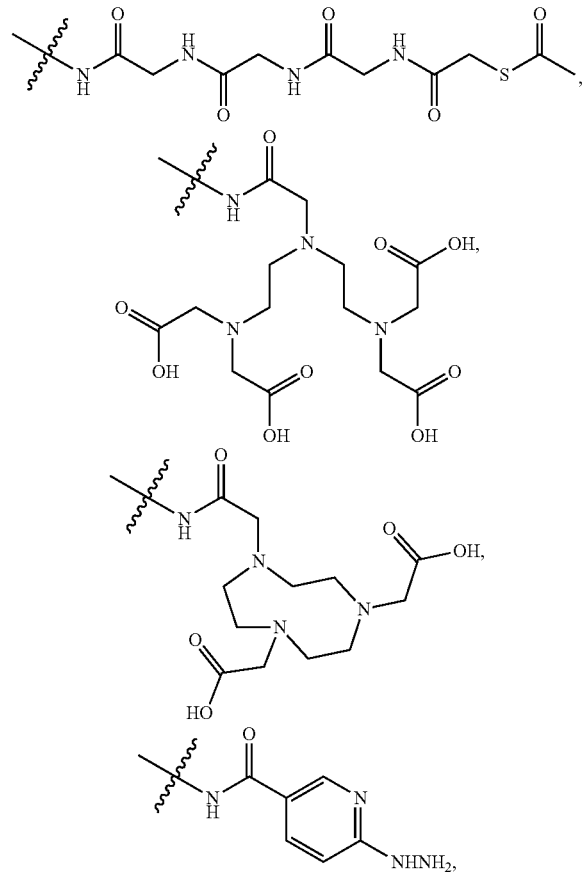

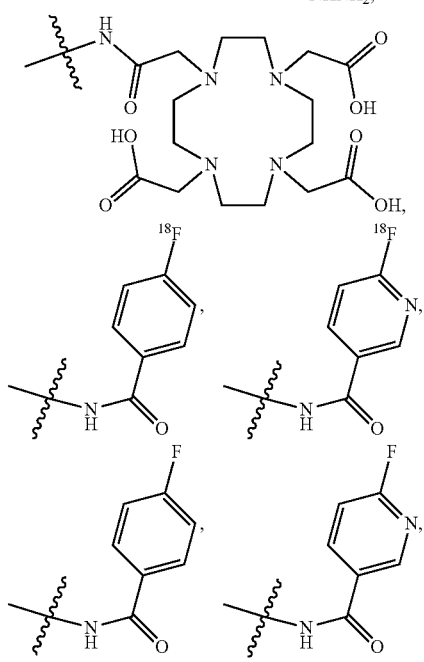

4

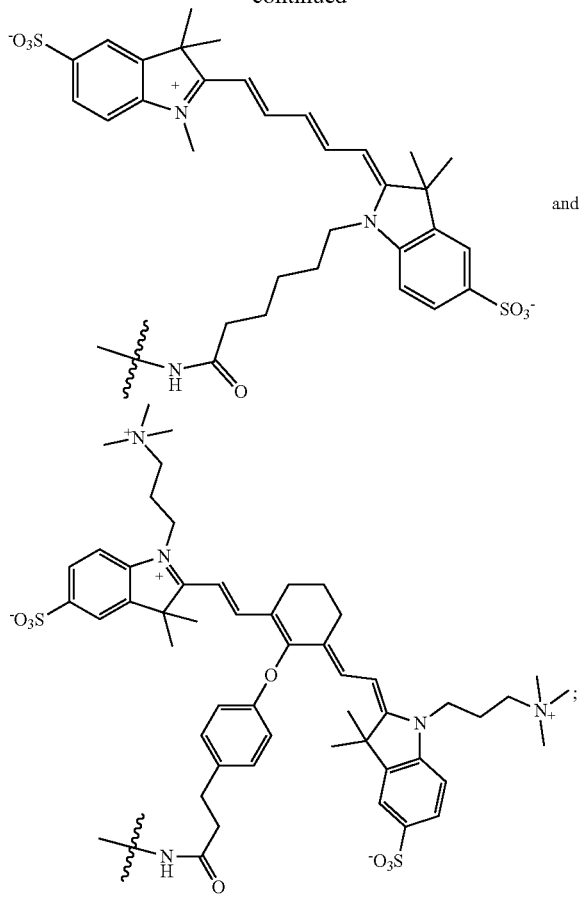

each occurrence of n is independently an integer ranging from 0 to 30; each occurrence of R' is independently selected from the group consisting of C$_1$-C$_6$ alkyl and C$_3$-C$_7$ cycloalkyl; and LG is a group capable of undergoing nucleophilic displacement.

The invention further provides a compound of formula II or a salt, solvate, stereoisomer, or tautomer thereof:

II

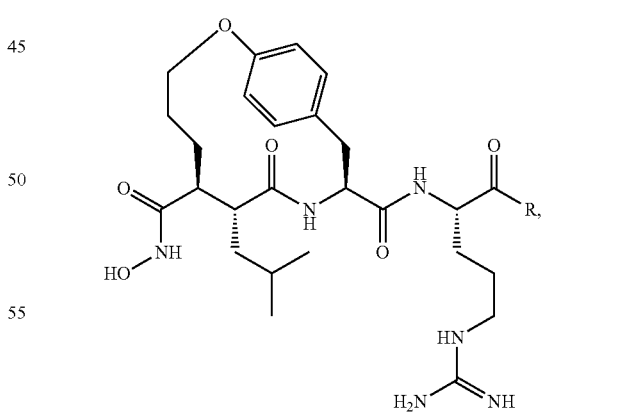

wherein R is selected from the group consisting of H, OH, OR', aroxy, heteroaroxy, SH, thioalkoxy, thiocycloalkoxy, —NH$_2$, —NHR' [such as but not limited to —NHCH$_3$, —NHCH$_2$CH$_3$, —NH(CH$_2$)$_2$CH$_3$ or —NHCH(CH$_3$)$_2$], —NR'R' [such as but not limited to —N(CH$_3$)$_2$, —N(CH$_3$)CH$_2$CH$_3$, or —N(CH$_2$CH$_3$)$_2$], —NH(aryl) and —NH(heteroaryl), wherein each occurrence of R' is independently selected from the group consisting of C$_1$-C$_6$ alkyl and C$_3$-C$_7$ cycloalkyl.

In certain embodiments, the compound of formula I is at least one selected from the group consisting of:
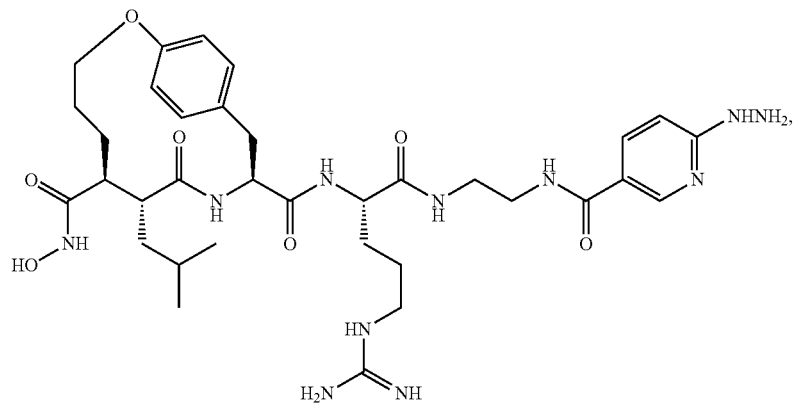
1
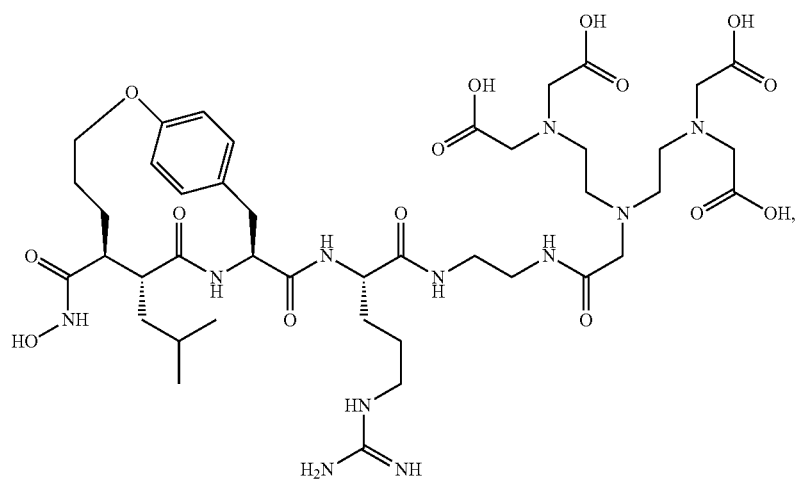
2
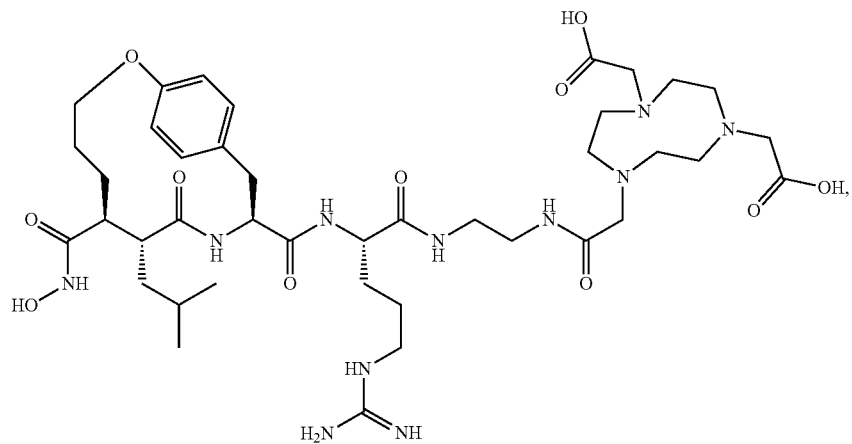
3

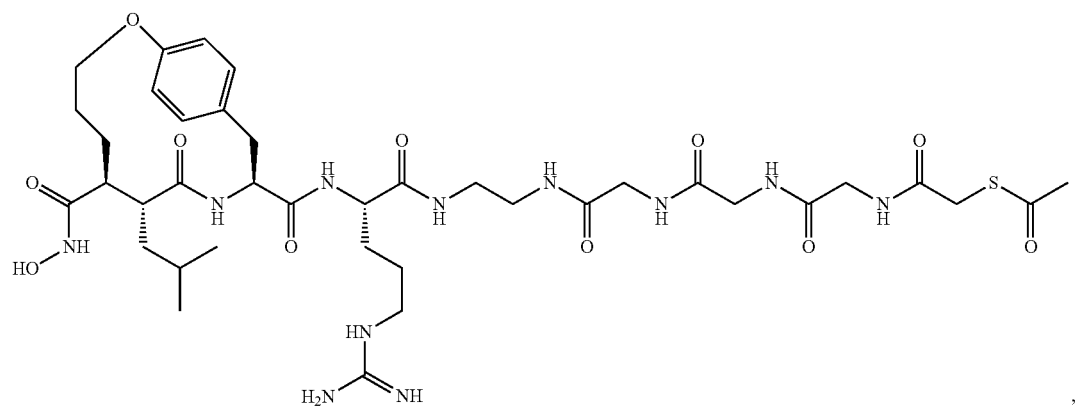
,
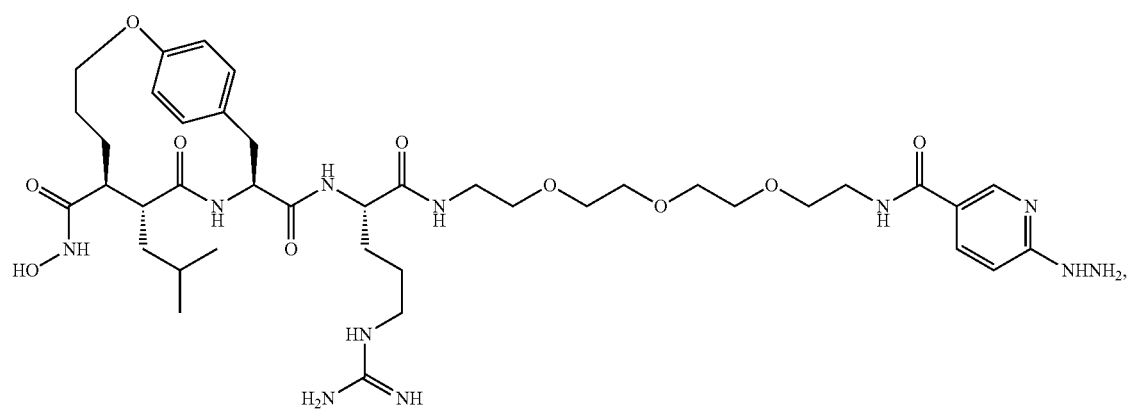
,
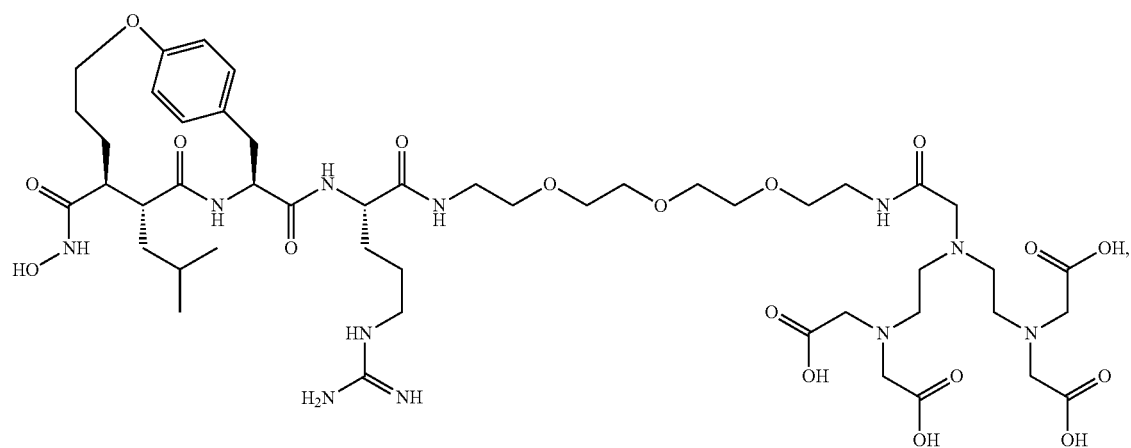

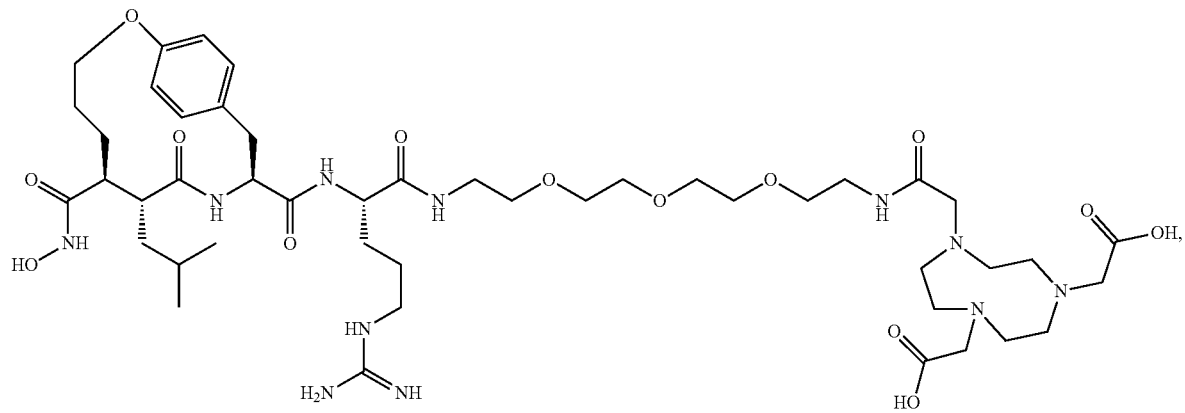
7
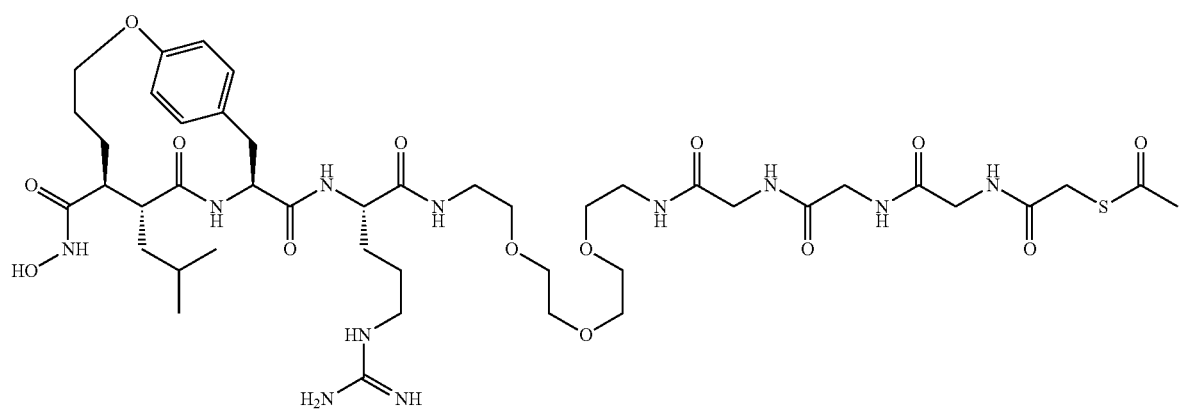
8
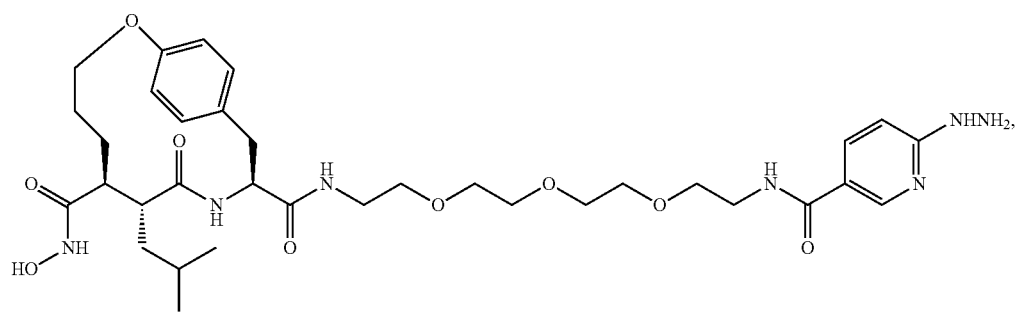
9
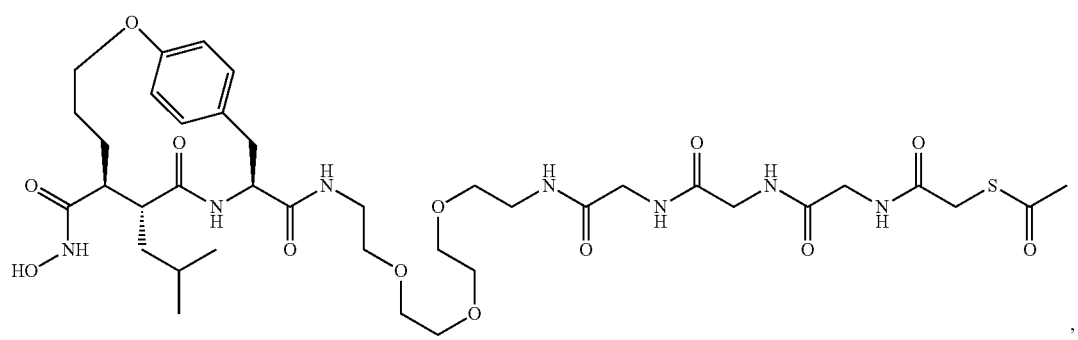
10

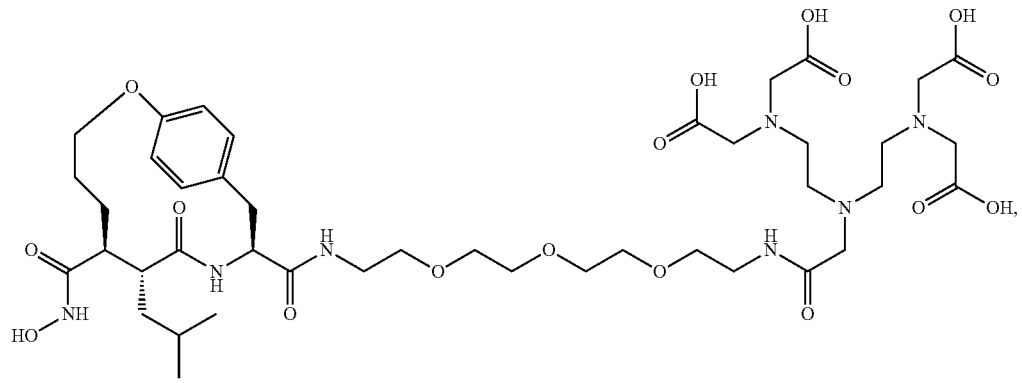
11
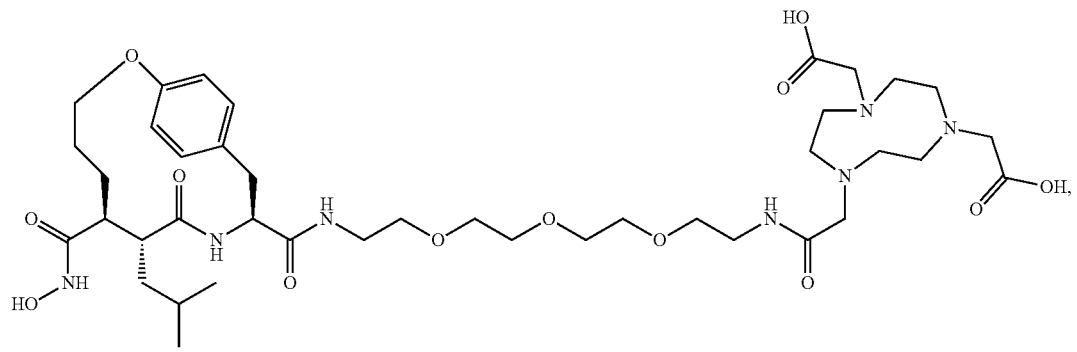
12
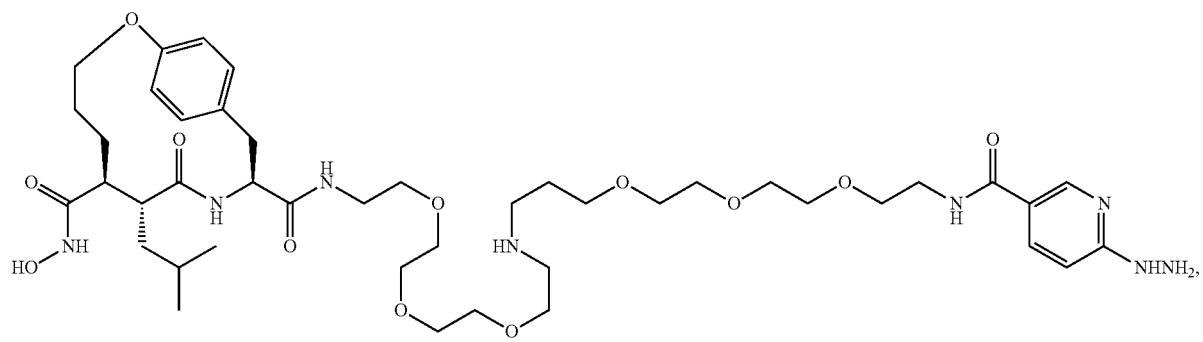
13
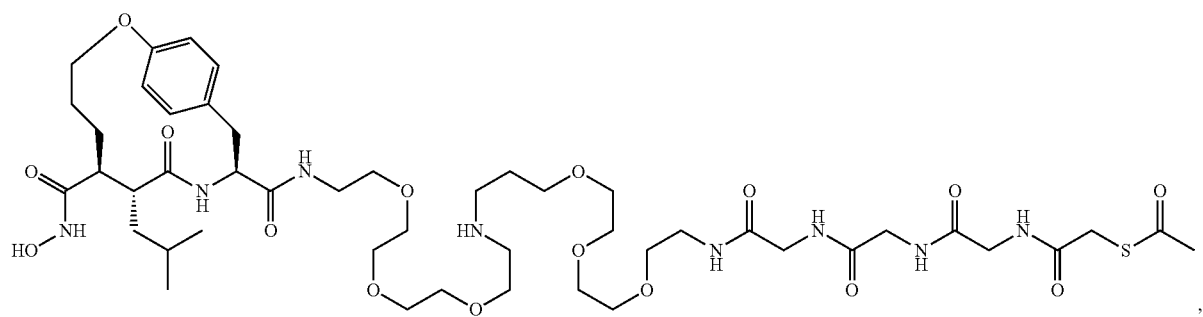
14

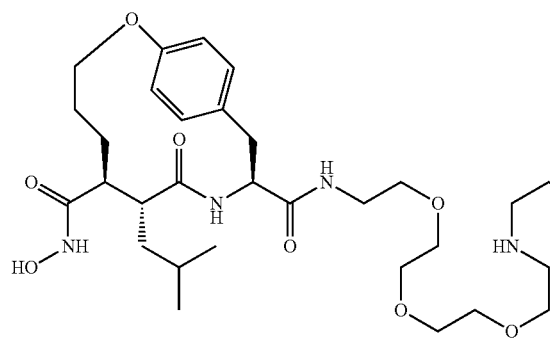

15

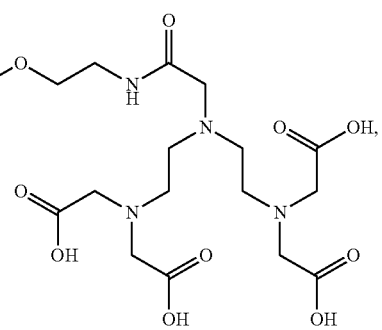

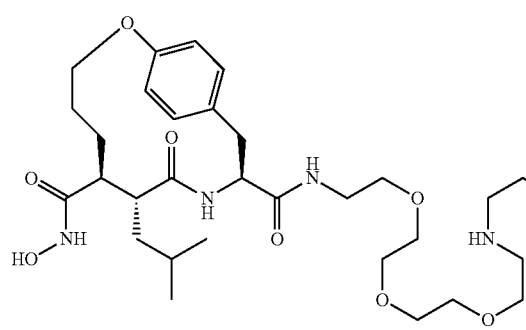

16

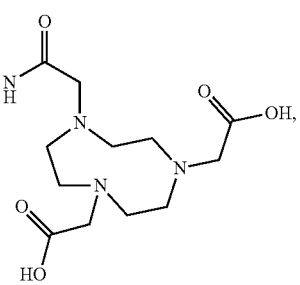

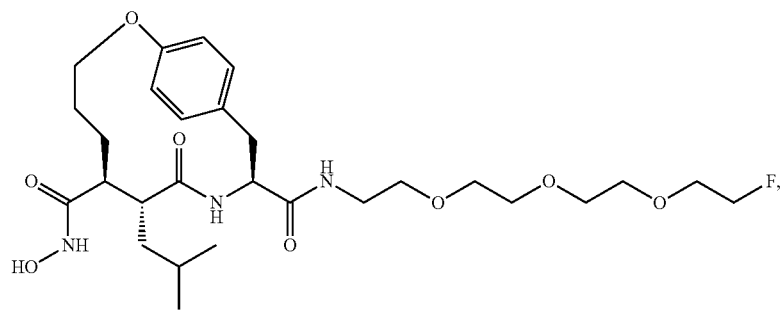

17

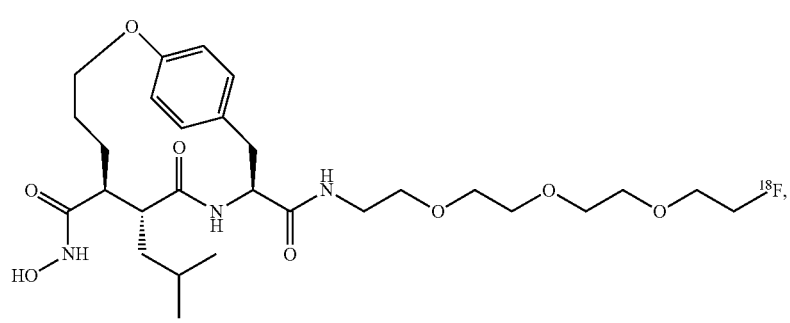

18 or a salt, solvate, stereoisomer, or tautomer thereof.

In certain embodiments, $R^3$ is present, and the compound of formula I further comprises a radioisotope-containing group, wherein the radioisotope is bound to and/or present in $R^3$. In other embodiments, the radioisotope is at least one selected from the group consisting of $^{99m}Tc$, $^{18}F$, $^{111}In$, $^{64}Cu$ and $^{68}Ga$. In yet other embodiments, the radioisotope-containing group further comprises one or more ligands that are bound to the radioisotope. In yet other embodiments, the one or more ligands help stabilize the radioisotope within the compound of formula I.

In certain embodiments, $R^3$ is present, and the compound of formula I further comprises a fluorophore-containing group.

In certain embodiments, $R^3$ is present, and the compound further comprises a radioisotope- and/or fluorophore-containing group comprising a radioisotope selected from the group consisting of $^{99m}Tc$, $^{18}F$, $^{111}In$ $^{64}Cu$ and $^{68}Ga$, and optionally further comprising one or more additional ligands, wherein the radioisotope is bound to $R^3$.

In certain embodiments, $R^3$ is present, and the compound further comprises a radioisotope- and/or fluorophore-containing group comprising a radioisotope selected from the group consisting of $^{99m}Tc$, $^{18}F$, $^{111}In$ $^{64}Cu$ and $^{68}Ga$, and further comprising one or more additional ligands, wherein the radioisotope is bound to $R^3$.

In certain embodiments, $R^1$ and/or $R^2$ comprises the group $N_3$ or $C\equiv CH$, and the compound is capable of undergoing a click reaction with a substrate comprising the group $C\equiv CH$ or $N_3$, respectively.

In certain embodiments, the compound of formula I is at least one selected from the group consisting of:

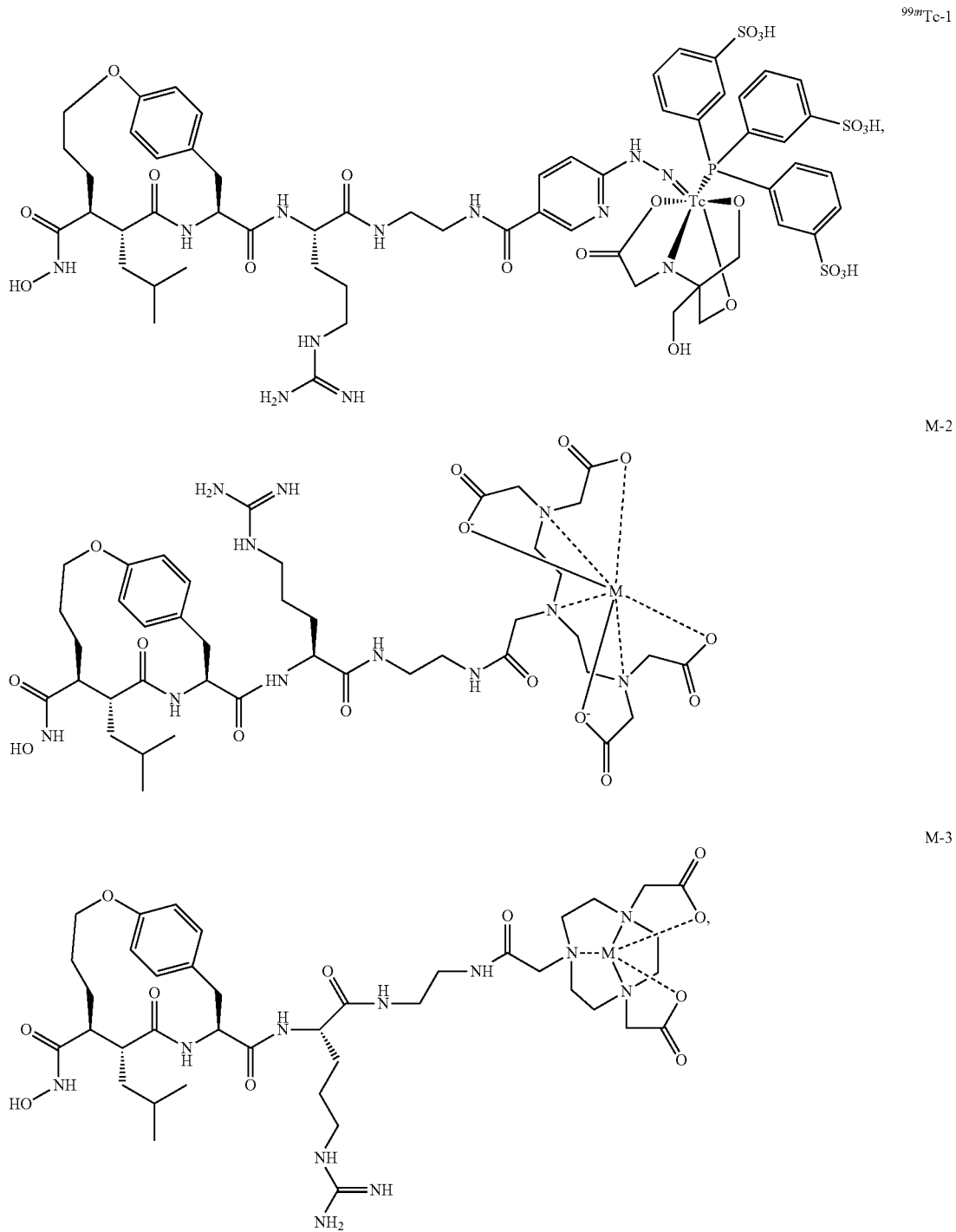

or a salt, solvate, stereoisomer, or tautomer thereof, wherein M is a metal, such as but not limited to a metal radioisotope.

In certain embodiments, the compound of formula II is at least one selected from the group consisting of:

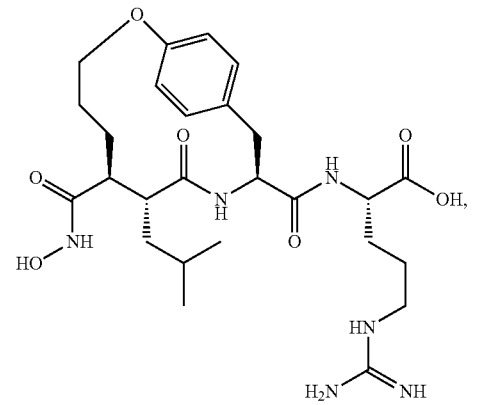

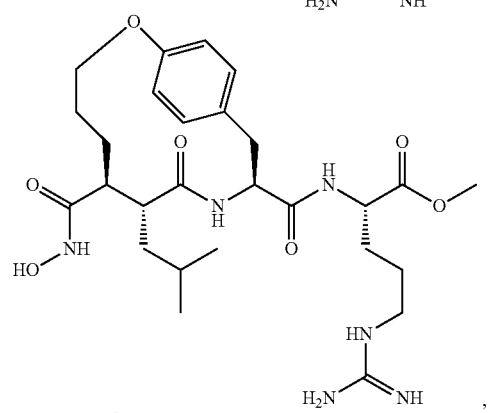

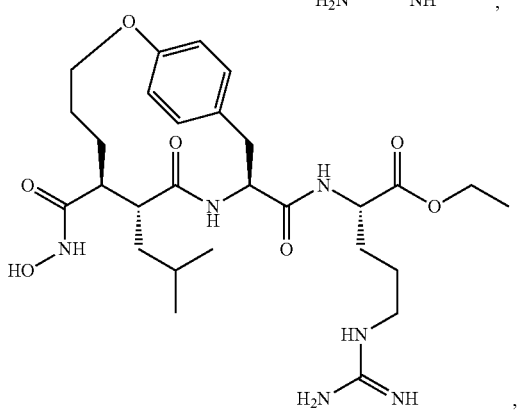

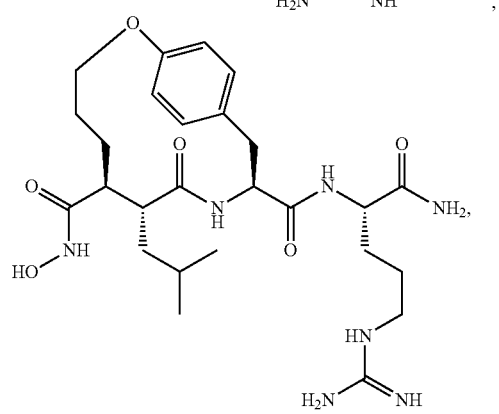

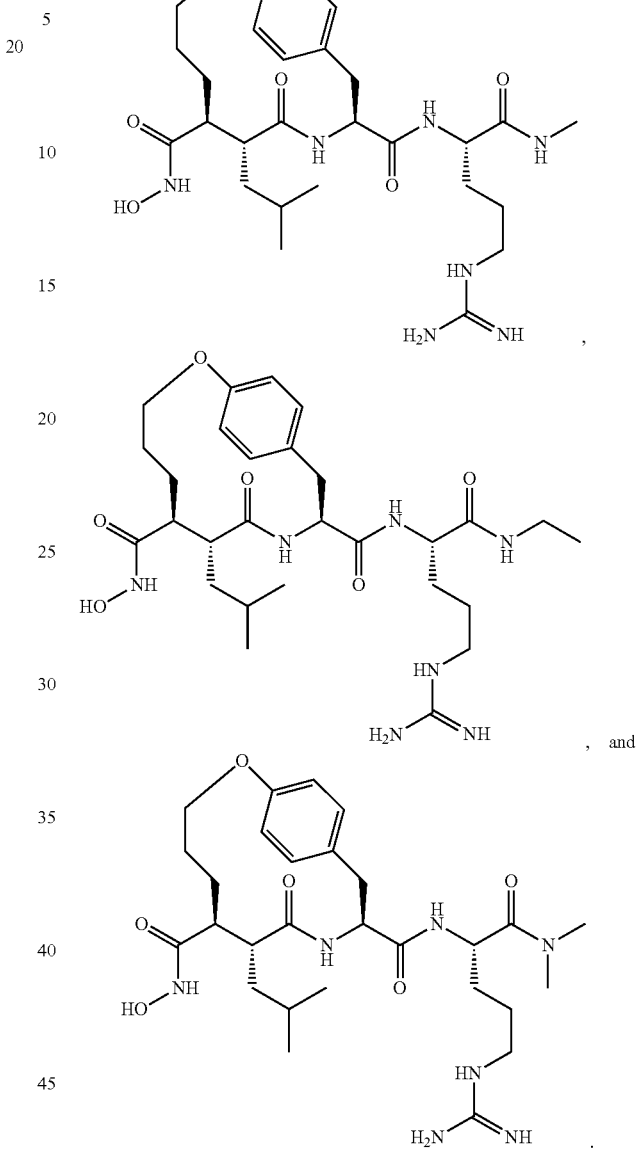

In certain embodiments, the compound is part of a pharmaceutical composition further comprising a pharmaceutically acceptable carrier, such as but not limited to normal saline, 5% dextrose, sodium bicarbonate, sodium phosphate and/or citrate.

The invention further provides a method of evaluating a subject's risk of developing a cardiovascular disease or disorder. The invention further provides a method of treating a matrix metalloproteinase-related disease or disorder in a subject.

In certain embodiments, the method comprises administering to the subject in need thereof a therapeutically effective amount of at least one compound of the invention. In other embodiments, the method comprises administering to a subject at least one compound of the invention, wherein the at least one compound comprises a radioisotope or fluorophore. In yet other embodiments, the method comprises acquiring an image of at least a portion of the subject's body. In yet other embodiments, the method comprises measuring the amount of compound bound to the imaged portion of the subject's body. In yet other embodiments, if the measured amount of bound compound is above a determined control amount, the subject is diagnosed as having an increased risk of developing the cardiovascular disease or disorder.

The invention further provides a kit comprising at least one compound and/or at least one pharmaceutical composition of the invention, an applicator, and instructions to use the at least one compound and/or the at least one composition to evaluate a subject's risk of developing a cardiovascular disease or disorder and/or treat a matrix metalloproteinase-related disease or disorder in a subject.

In certain embodiments, the subject is a mammal. In other embodiments, the subject is a human. In yet other embodiments, the disease or disorder is at least one selected from the group consisting of cancers, inflammatory diseases, cardiovascular diseases, stroke, aneurysm, periodontitis, hepatitis, cirrhosis, portal hypertension, glomerulonephritis, atherosclerosis, emphysema, asthma, pulmonary fibrosis, autoimmune disorders of skin and dermal photoaging, rheumatoid arthritis, osteoarthritis, multiple sclerosis, Alzheimer's disease, chronic ulcerations, uterine involution and bone resorption.

In certain embodiments, the therapeutically effective amount of the at least one compound ranges from about 10 ng to 1000 mg. In other embodiments, the at least one compound is administered to the subject through a route selected from the group consisting of oral, nasal, inhalational, topical, buccal, rectal, pleural, peritoneal, intra-peritoneal, vaginal, intramuscular, subcutaneous, transdermal, epidural, intratracheal, otic, intraocular, intrathecal, and intravenous.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 4A-4D illustrate non-limiting examples of morphology (FIGS. 4A-4B) and autoradiography (FIGS. 4C-4D) of aortae and carotid arteries from apoE$^{-/-}$ mice with CaCl$_2$-induced carotid aneurysm injected with $^{99m}$Tc-1 with (FIGS. 4A, 4C) and without (FIGS. 4B, 4D) excess of unlabeled analogue (19). FIGS. 4E-4F illustrate autoradiographic quantification of $^{99m}$Tc-1 uptake in carotid aneurysm and aorta (FIG. 4E) and aneurysm-to-aorta uptake ratio (FIG. 4F) for control (●) and blocking (✳) groups. ID: injected dose. * P<0.05, ** P<0.01.

FIGS. 9A-9B: Examples of fused $^{99m}$Tc-1 SPECT/CT images of animals from the low remodeling (FIG. 9A) and aneurysm (FIG. 9B) groups, classified based on visual in situ analysis of the abdominal aorta. Transversal (left), coronal (middle) and sagittal (right) views are shown. Arrows point to the areas of maximal tracer uptake in the abdominal aorta. FIG. 9C: Quantification of $^{99m}$Tc-1 signal in area of maximal tracer uptake in the suprarenal abdominal aorta in low remodeling (LR) and aneurysm (AAA) groups. *P<0.05. FIG. 9D: Correlation between $^{99m}$Tc-1 signal in vivo and MMP activity quantified by zymography ex vivo. cpv: counts per voxel, AU: arbitrary units.

FIG. 10A: Maximal external diameter of the abdominal aorta in low remodeling (LR) and aneurysm (AAA) groups. FIG. 10B: Aortic MMP activity quantified by zymography in LR and AAA groups. ** P<0.01. AU: arbitrary units.

DETAILED DESCRIPTION OF THE INVENTION

Figure 1:
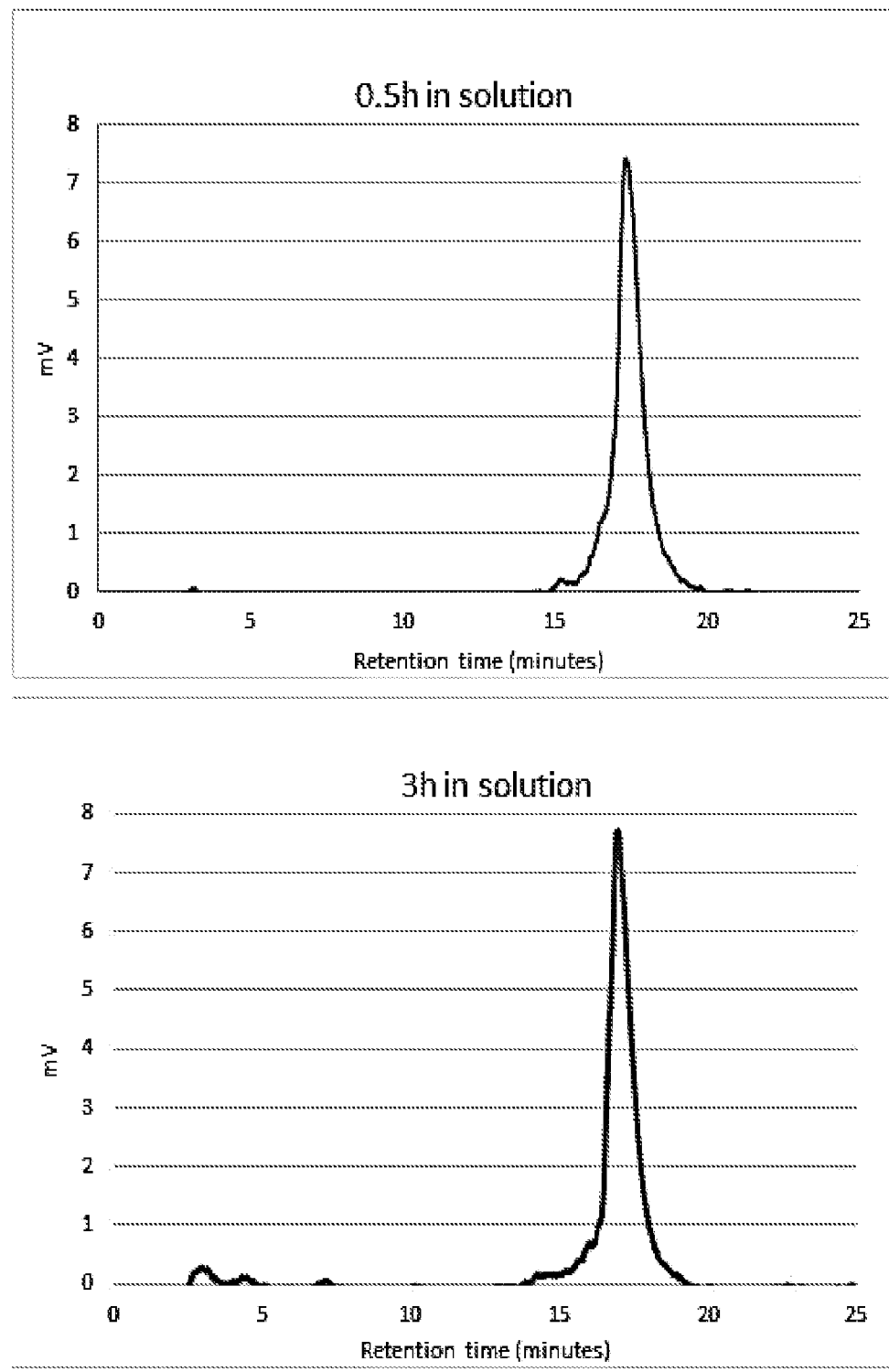
FIG. 1 illustrates a non-limiting radio-HPLC analysis of $^{99m}$Tc-2.

The invention relates, in certain aspects, to the unexpected discovery that compounds of formula I strongly and selectively bind to MMPs. The compounds of the invention can further be labelled with one or more radioisotope-containing and/or fluorophore-containing labels. In certain embodiments, labeled compounds of formula I are used as MMP-targeted imaging agents. In other embodiments, labeled compounds of formula I are used to diagnose MMP-related diseases.

In certain embodiments, labeled compounds of formula I exhibit improved solubility when compared to currently used MMP-targeted imaging agents (such as, but not limited to, $^{99m}$Tc-RP805). In other embodiments, labeled compounds of formula I have faster excretion (shorter retention times in blood) than currently used MMP-targeted imaging agents (such as $^{99m}$Tc-RP805).

The invention relates in other aspects to the unexpected discovery that compounds of formula II strongly and selectively bind to MMPs. In certain embodiments, compounds of formula I and/or II may be used to inhibit MMP activity and/or treat diseases characterized by MMP upregulation and activation.

As demonstrated herein, an illustrative water-soluble zwitterionic MMP inhibitor 1 was designed and evaluated, using RP805 as a comparator. 1 was labeled with $^{99m}$Tc- to yield ($^{99m}$Tc-1), which radiochemical stability was evaluated by radio-high-performance liquid chromatography analysis. Tracer blood kinetics and biodistribution for that compound were compared with $^{99m}$Tc-RP805 in C57BL/6J mice (n=10). $^{99m}$Tc-1 binding to aneurysm and specificity were evaluated by quantitative autoradiography in apolipoprotein E-deficient (apoE$^{-/-}$) mice with CaCl$_2$-induced carotid aneurysm (n=11). Angiotensin II (Ang II)-infused apoE$^{-/-}$ (n=16) were used for micro-single-photon emission computed tomography (SPECT)/computed tomography (CT) imaging. Aortic tissue MMP activity and macrophage marker, CD68 expression were assessed by zymography and reverse transcription-polymerase chain reaction.

1 showed nanomolar range inhibition constants for several MMPs. $^{99m}$Tc-1 was radiochemically stable in mouse blood for 5 hours, and demonstrated rapid renal clearance and lower blood levels in vivo compared to $^{99m}$Tc-RP805.

$^{99m}$Tc-1 binding to aneurysm and its specificity were shown by autoradiography in carotid aneurysm. Ang II infusion in apoE$^{-/-}$ mice for 4 weeks resulted in AAA formation in 36% (4/11) of surviving animals. In vivo $^{99m}$Tc-1 microSPECT/CT images showed higher uptake of the tracer in AAA compared to non-dilated aortae. Specific aortic uptake of $^{99m}$Tc-1 in vivo correlated with aortic MMP activity, CD68 expression and inflammation.

1 showed good water solubility, while retaining MMP binding potential. In comparison with $^{99m}$Tc-RP805, $^{99m}$Tc-1 has a faster blood clearance, which (without wishing to be limited by any theory) is favorable for early time point imaging.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described. As used herein, each of the following terms has the meaning associated with it in this section.

Generally, the nomenclature used herein and the laboratory procedures in cell culture, oncology, cardiology, molecular genetics, pharmacology and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain instances, hyperproliferative disorders are referred to as a type of cancer including but not limited to primary or metastatic melanoma, thymoma, lymphoma, sarcoma, lung cancer, liver cancer, non-Hodgkin's lymphoma, Hodgkin's lymphoma, leukemias, uterine cancer, cervical cancer, bladder cancer, kidney cancer and adenocarcinomas such as breast cancer, prostate cancer, ovarian cancer, pancreatic cancer, and the like.

The terms "cardiovascular disease" and "cardiovascular disorder" as used herein refer to diseases or disorders affecting the heart and/or peripheral vascular system. Examples of cardiovascular diseases or disorders include but are not limited to coronary artery diseases, angina, myocardial infarction ("heart attack"), stroke, hypertensive heart disease, rheumatic heart disease, cardiomyopathy, myocardial remodeling, heart arrhythmia, congenital heart disease, valvular heart disease such as calcific aortic valve disease, carditis, vascular remodeling, restenosis, aortic aneurysms, brain aneurysms, peripheral artery disease such as carotid stenosis, pulmonary arterial hypertension, device (for example pacemaker, defibrillator, left ventricular assist device) infection or clot formation, and arterial and venous thrombosis. Cardiovascular diseases and disorders may be related to, or caused by, for example, atherosclerosis, high blood pressure, smoking, diabetes, lack of exercise, obesity, high blood cholesterol, poor diet, focal or systemic inflammation, and excessive alcohol consumption.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

The term "musculoskeletal diseases" as used herein are defined as diseases or disorders affecting the joints, muscles and bones. Examples of musculoskeletal diseases include arthritis, gout, joint infection, and abnormalities of bones, joints and muscles associated with systemic diseases. Musculoskeletal diseases may be caused by trauma, infection, inflammation, genetics, or idiopathic.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethane sulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation. By "pharmaceutical formulation" it is further meant that the carrier, solvent, excipient(s) and/or salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

As used herein, the term "prevent," "prevention," or "preventing" refers to any method to partially or completely prevent or delay the onset of one or more symptoms or features of a disease, disorder, and/or condition. Prevention is causing the clinical symptoms of the disease state not to develop, i.e., inhibiting the onset of disease, in a subject that may be exposed to or predisposed to the disease state, but does not yet experience or display symptoms of the disease state. Prevention may be administered to a subject who does not exhibit signs of a disease, disorder, and/or condition.

The term "pulmonary disease" as used herein are defined as diseases or disorders affecting the lungs and respiratory system. Examples of pulmonary diseases include but are not limited to chronic obstructive pulmonary disease, pulmonary fibrosis, asthma, pulmonary hypertension, lung inflammation, and lung infection. Pulmonary diseases may be caused by smoking, exposure to irritants, allergy, genetics, or unknown causes (idiopathic).

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "therapeutically effective amount" is an amount of a compound of the invention, that when administered to a patient, treats, minimizes and/or ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Figure 12:
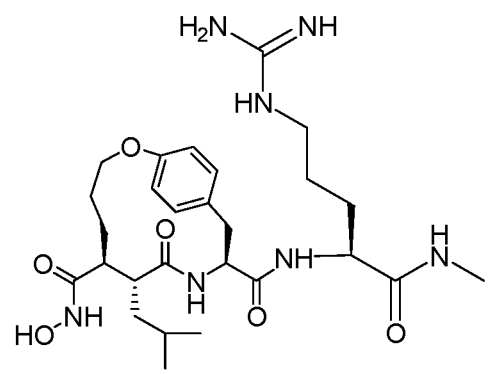
FIG. 12 illustrates chemical structures of formula II, R=NHCH$_3$ (19) (A), 1 (also described as RYM1 herein; B), $^{99m}$Tc-1 (C) and $^{99m}$Tc-RP805 (D).
Figure 12:
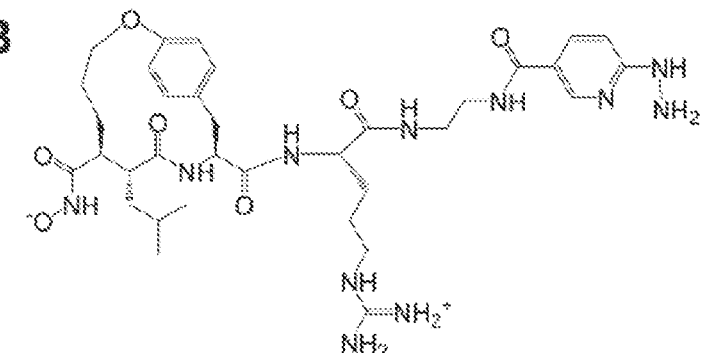
Figure 12:
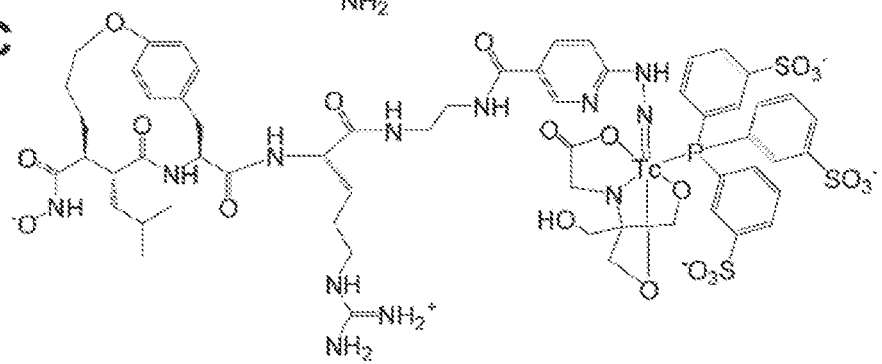
Figure 12:
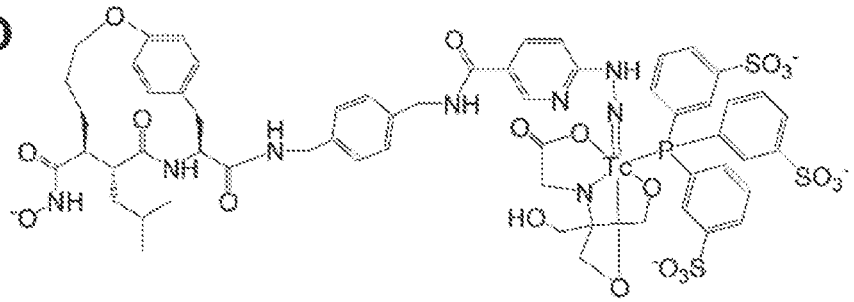

The following abbreviations are used herein: AAA, abdominal aortic aneurysm; AU, arbitrary units; cpv, counts per voxel; CT, computed tomography; DCM, dichloromethane; DTPA, diethylene triamine pentaacetic acid, or a salt thereof; ID, injected dose; LR, low remodeling; MAG, S-acetylmercaptoacetyl triglycine, or a salt thereof; MAS, S-acetylmercaptoacetyltriserine, or a salt thereof; MMP, matrix metalloproteinase; NOTA, 1,4,7-triazacyclononane-1,4,7-trisacetic acid, or a salt thereof; PAH, pulmonary arterial hypertension; pAT, periaortic adipose tissue; PEG, polyethylene glycol; PET, positron emission tomography; rhMMP, recombinant human matrix metalloproteinase; SG, salivary glands; SPECT, single-photon emission computed tomography; $^{99m}$Tc-RP805, compound D in FIG. 12, or a salt or solvate thereof; $t_R$, retention time; WAT, white adipose tissue.

Compounds and Compositions

The present invention relates to a compound of formula I, or a compound of formula II, or a salt, solvate, stereoisomer, or tautomer thereof, as recited elsewhere herein.

In certain embodiments, the compound of formula I binds to at least one MMP. In other embodiments, the compound of formula I binds to at least one MMP and allows for MMP imaging. In yet other embodiments, the compound of formula I is useful as imaging agents for positron emission tomography (PET) and/or single-photon emission computed tomography (SPECT) and/or optical imaging. In yet other embodiments, the compound of formula I is used to diagnose cardiovascular diseases and/or disorders, pulmonary diseases and/or disorders, musculoskeletal diseases and/or disorders, cancer and other diseases and disorders.

The invention provides a compound of formula I, or a salt, solvate, stereoisomer, or tautomer thereof:

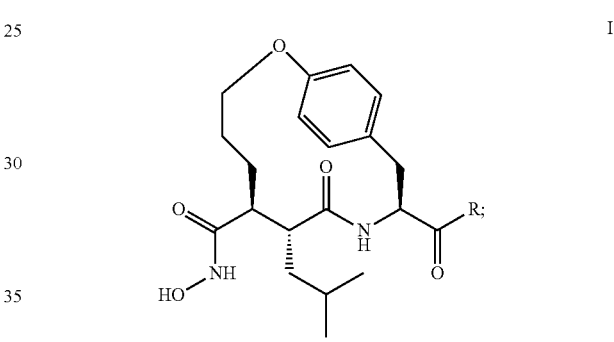

I wherein: R is selected from the group consisting of OH, —NH$_2$, —NHR', —NR'R', —NH(aryl), —NH(heteroaryl) and —NHR$^1$; R$^1$ is selected from the group consisting of:

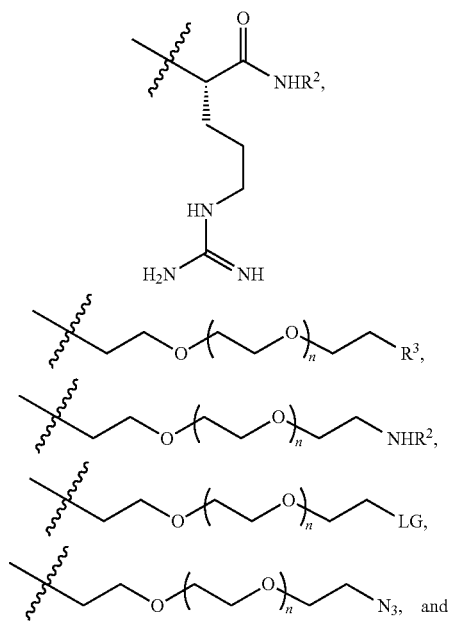

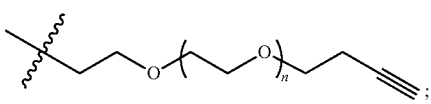

$R^2$ is selected from the group consisting of:

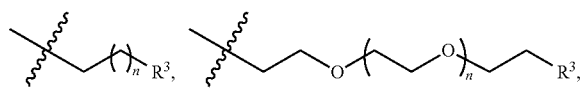

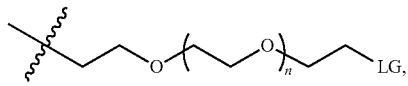

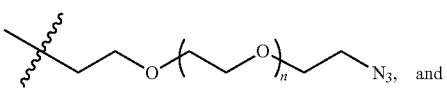

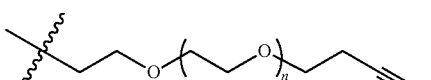

$R^3$ is selected from the group consisting of H, OH, OCH$_3$, F, $^{18}$F,

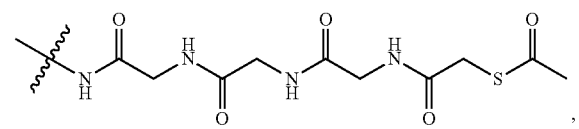

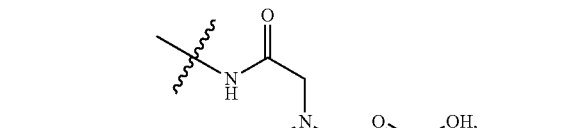

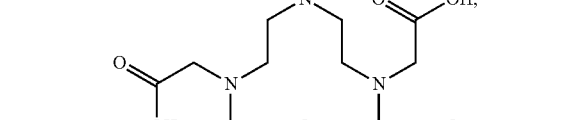

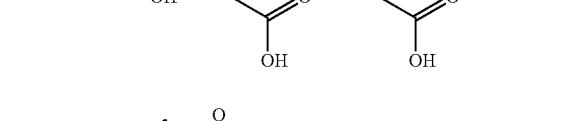

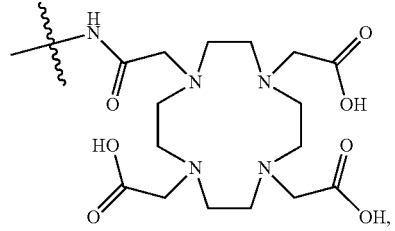

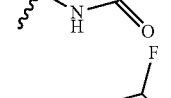

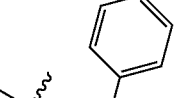

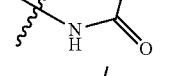

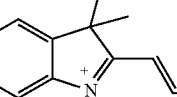

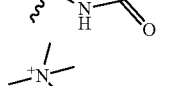

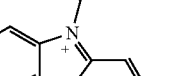

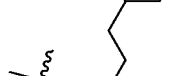

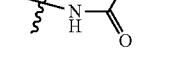

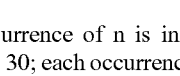

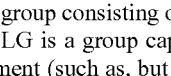

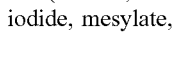

each occurrence of n is independently an integer ranging from 0 to 30; each occurrence of R' is independently selected from the group consisting of C$_1$-C$_6$ alkyl and C$_3$-C$_7$ cycloalkyl; and LG is a group capable of undergoing nucleophilic displacement (such as, but not limited to, fluoride, chloride, bromide, iodide, mesylate, tosylate, triflate, and the like).

The invention further provides a compound of formula II or a salt, solvate, stereoisomer, or tautomer thereof:

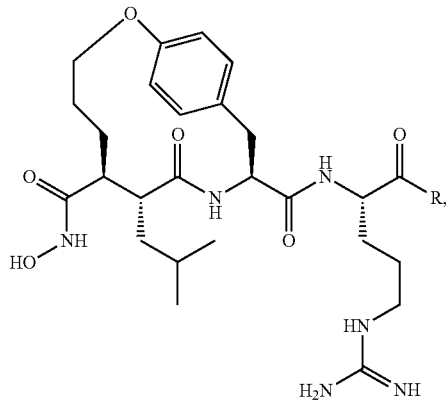

wherein R is selected from the group consisting of H, OH, OR', aroxy, heteroaroxy, SH, thioalkoxy, thiocycloalkoxy, —NH$_2$, —NHR' (such as but not limited to —NHCH$_3$, —NHCH$_2$CH$_3$, —NH(CH$_2$)$_2$CH$_3$ or —NHCH(CH$_3$)$_2$), —NR'R', —NH(aryl) and —NH(heteroaryl), wherein each occurrence of R' is independently selected from the group consisting of C$_1$-C$_6$ alkyl and C$_3$-C$_7$ cycloalkyl.

In certain embodiments, the compound of formula I is a macrocyclic hydroxamate, or a salt, solvate, stereoisomer, or tautomer thereof, selected from the group consisting of 1-18.

In certain embodiments, the labeled compound of formula I is one selected from the group consisting of $^{99m}$Tc-1, M-2, and M-3 (wherein M is a metal).

In certain embodiments, the compound of formula II is at least one selected from the group consisting of:

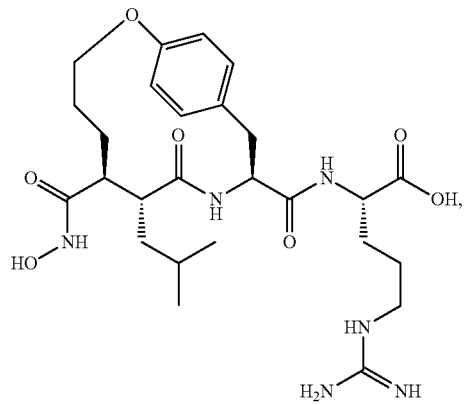

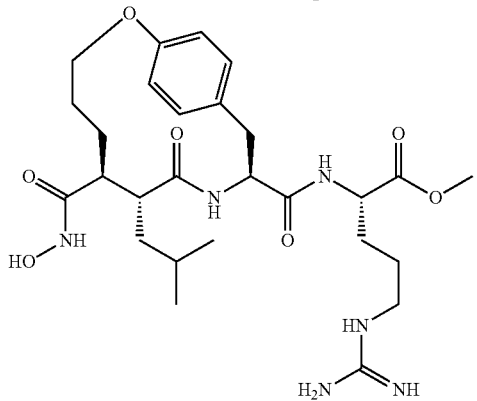

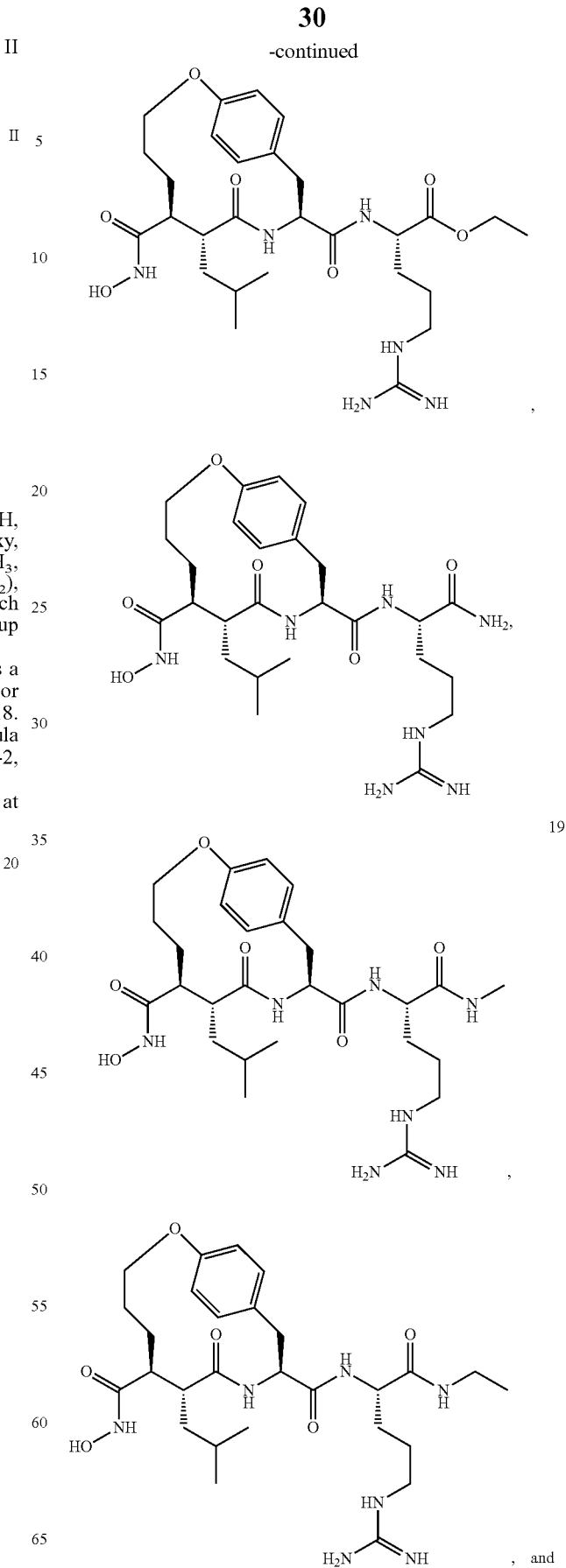

, and

-continued

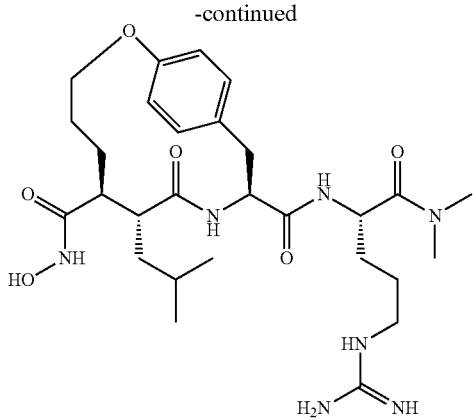

In certain embodiments, each occurrence of n is independently an integer ranging from 0 to 2, 0 to 4, 0 to 6, 0 to 8, 0 to 10, 0 to 12, 0 to 14, 0 to 16, 0 to 18, 0 to 20, 0 to 22, 0 to 24, 0 to 26, 0 to 28, 2 to 4, 4 to 6, 6 to 8, 8 to 10, 10 to 12, 12 to 14, 14 to 16, 16 to 18, 18 to 20, 20 to 22, 22 to 24, 24 to 26, 26 to 28, 28 to 30, or any interval therein.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Methods

In one aspect, the present invention includes methods of using compounds of formula I as MMP-targeted imaging agents. In certain embodiments, the method comprises contacting a compound of the invention with a cell or tissue that expresses at least one MMP. In other embodiments, the method further comprises detecting the compound bound to the MMP-expressing cell or tissue.

In certain embodiments, the compounds of formula I can be used to diagnose matrix metalloproteinase related diseases and disorders. In other embodiments, the diseases or disorders are at least one selected from the group consisting of cancers, inflammatory diseases, cardiovascular diseases (including valvular diseases), periodontitis, hepatitis, cirrhosis, portal hypertension, glomerulonephritis, atherosclerosis, emphysema, asthma, pulmonary fibrosis, autoimmune disorders of skin and dermal photoaging, rheumatoid arthritis, osteoarthritis, multiple sclerosis, Alzheimer's disease, chronic ulcerations, uterine involution and bone resorption.

In another aspect, the invention includes methods of evaluating a subject's risk of developing a cardiovascular disease or disorder, the method comprising administering to the subject a compound of formula I and acquiring an image of at least a portion of the subject's body, wherein the level of compound of formula I bound to the imaged portion of the subject's body is measured. If the measured level of bound compound of formula I is above a determined control level, the subject is diagnosed as having an increased risk of developing a cardiovascular disease or disorder. In other embodiments, the methods of the invention allow for tracking the effect of therapeutic interventions, adjusting the dose or level of therapeutic intervention, and/or assessing its effectiveness. In yet other embodiments, the methods of the invention are used during surgery and other invasive procedures to assess the extent of focal disease, or to characterize the disease, e.g., to assess atherosclerotic plaque vulnerability. In yet other embodiments, the methods of the invention identify a subject that has yet-undiagnosed and/or early-onset disease. In yet other embodiments, the methods of the invention stratify the subject's disease risk.

In yet another aspect, the invention includes methods of using a compound of formula I or II to treat MMP-related diseases. These diseases and disorders can be at least one selected from the group consisting of cancers, inflammatory diseases, cardiovascular diseases, including valvular diseases, periodontitis, hepatitis, cirrhosis, portal hypertension, glomerulonephritis, atherosclerosis, emphysema, asthma, pulmonary fibrosis, autoimmune disorders of skin and dermal photoaging, rheumatoid arthritis, osteoarthritis, multiple sclerosis, Alzheimer's disease, chronic ulcerations, uterine involution and bone resorption.

In certain embodiments, the method comprises administering to a patient in need thereof a therapeutically effective amount of a compound of formula I or formula II, or a salt, solvate, stereoisomer, or tautomer thereof, wherein the compound is optionally formulated in a pharmaceutical composition. In other embodiments, the compound of the invention is administered by a route comprising parenteral (such as for example intravenous), oral, subcutaneous, and/or intradermal administration. After a delay to allow for tracer biodistribution (which can range for 10 seconds to 3 days), uptake of the compound in the subject's tissues can be detected and quantified by PET, SPECT, nuclear planar, or optical imaging, or any other applicable method. The dosage range of the compound of the invention may be, for example, from about 10 ng to 1,000 mg. In certain embodiments, the subject is a mammal. In other embodiments, the subject is human.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. The pharmaceutical compositions useful for practicing the invention may be administered to deliver a dose of from 1 ng/kg/day and 100 mg/kg/day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient. In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent (i.e., capable of treating a disease or disorder contemplated herein) in the composition. In yet other embodiments, the compound of the invention is the only biologically active agent (i.e., capable of treating a disease or disorder contemplated herein) in therapeutically effective amounts in the composition. The carrier may be a solvent or dispersion medium containing, for example, water, ethanol, polyol (for example, glycerol, propylene glycol, and liquid polyethylene glycol, and the like), suitable mixtures thereof, and vegetable oils.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg, or less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intraperitoneal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form. For sustained release, the compounds may be formulated with a suitable polymer or hydrophobic material that provides sustained release properties to the compounds. The compounds useful within the methods of the invention may be administered in the form of microparticles, for example by injection, or in the form of wafers or discs by implantation. In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses. The amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Mouse Model of Carotid Aneurysm:

Arterial aneurysm was induced by exposing the left common carotid artery of apolipoprotein E-deficient (apoE$^{-/-}$) mice to calcium chloride. Briefly, 4- to 6-wk-old female apoE$^{-/-}$ mice (n=96; Jackson Laboratory) were fed high-cholesterol chow ad libitum. After 1 wk, the carotid arteries were exposed by blunt-end dissection under anesthesia. The left common carotid artery just below the carotid bifurcation was adventitially exposed to a 10% solution of $CaCl_2$ for 20 min. The opposite carotid artery was exposed to normal saline and served as a control for imaging studies (Razavian, et al., 2010, J Nucl Med. 51(7):1107-15).

In addition, sixteen weeks-old male apoE$^{-/-}$ (n=16) were infused with human angiotensin II (Ang II, 1000 ng/kg/min, Calbiochem), delivered by a subcutaneous osmotic minipump (Model 2004, Alzet) implanted under anesthesia (isoflurane 2%).

Mouse Model of PAH:

Six to eight week old C57BL/6J mice of either sex were exposed to chronic hypoxia (10%) in a hypoxia chamber for up to 4 weeks. Age and sex-matched normoxic mice were used as control.

Affinity and Selectivity Profile Assessment:

MMPs were purchased from R&D Systems (Minneapolis, Minn.). MMP inhibition assays were carried out in 50 mM Tris/HCl buffer, pH=6.8, 10 mM $CaCl_2$ at 25° C. Pro-MMPs were pre-activated by p-aminophenylmercuric acetate (described in Devel, et al., 2006, J. Biol. Chem. 281:11152-11160). Titration experiments were carried out to determine active enzyme concentration for each MMP prior to the assay. For each probe, the % of inhibition was determined from five different concentrations in triplicates, chosen to reach a range of 20-80% inhibition. K values were determined using the method described in Horovitz & Levitzki, 1987, Proc. Natl. Acad. Sci. USA 84:6654-6658.

Probe Stability Assessment:

Tracers were incubated in blood (200 µL) with gentle agitation (Thermo mixer, 1000 rpm) at 37° C. for 4 h. At 0, 2, and 4 h time points, 40 µL of blood sample were collected and centrifuged at 4° C. (3000 rpm, 20 min). 10 µL of the supernatant (plasma) were collected and diluted in methanol (90 µL). The sample was then vortexed for 30 s at room temperature and centrifuged at 4° C. (3000 rpm, 15 min). 50 µL of the supernatant were concentrated, filtered and analysed by radioHPLC or LC-MS.

Biodistribution

For comparison of $^{99m}$Tc-1 and $^{99m}$Tc-RP805 biodistribution, C57BL/6J mice were injected intravenously with 16±5 MBq of either $^{99m}$Tc-1 (n=5) or $^{99m}$Tc-RP805 (n=5). To investigate biodistribution in apoE$^{-/-}$ mice, animals at seven weeks after peri-adventitial application of CaCl$_2$ or NaCl to carotid arteries were injected with 31±14 MBq (14±2 pg/kg) of $^{99m}$Tc-1, with (n=5) or without (n=6) pre-injection of an excess of the parent inhibitor 19 (23±8 ng/kg). Animals were kept under anesthesia for 60 min and blood samples were collected at various times post-injection. Tissue samples and body fluids were collected and weighed at 2 hours post-injection, and measured for their radioactivity by gamma-well counting (WIZARD2®, PerkinElmer). Data were expressed as percentage of injected dose (ID) per gram of tissue or mL of blood.

Autoradiography:

For autoradiography, the specimens were mounted on a board and placed in contact with to a reusable phosphor screen (MultiSensitive Phosphor Screen, PerkinElmer) along with standards of known activity. The screen was scanned in a phosphor imager system (Typhoon Trio, GE Healthcare Life Sciences) at a pixel size of 25×25 μm and images were analyzed using the Fiji software. Tracer uptake was quantified using a standard curve and expressed a % injected dose (ID)/pixel.

Quantitative Autoradiography

In apoE$^{-/-}$ mice at seven weeks after peri-adventitial application of CaCl$_2$ or NaCl to carotid arteries, the aorta and carotid arteries were dissected from surrounding adherent tissues under a stereoscopic microscope (MZ9.5, Leica) at 2 hours post-tracer injection. The tissues were placed on a phosphor screen (MultiSensitive Phosphor Screen, PerkinElmer) along with standards of known activity. The phosphor screen was scanned with a phosphor imager (Typhoon Trio, GE Healthcare Life Sciences), and the digitalized images were quantified by drawing regions of interest around various tissues to determine tissue activity (Fiji/ImageJ software, NIH).

MicroSPECT/CT:

Animals were imaged using a dedicated high resolution small animal imaging system (X-SPECT, GammaMedica), using one mm low energy (for $^{99m}$Tc) pinhole collimators. The spatial resolution of this system for $^{99m}$Tc in tomographic images with a 1-mm pinhole collimator and 4 cm radius of rotation was 1.1 mm full-width half-maximum. Radiotracer (1 mCi for mice) was injected through an intravenous catheter. Anesthetized mice (with isoflurane) were placed in a fixed position under the camera. Three point sources of known activity (~1 μCi) were placed in the field of view, but outside the body, to quantify tracer uptake and to verify the accuracy of image fusions. One hour after tracer administration microSPECT imaging was performed in a step and shoot manner, using 1 mm pinhole collimators and the following acquisition parameters empirically optimized for similar imaging studies: 180°, 64 projections, 30 sec/projection (~40 minute image acquisition), matrix 82×82, 140 keV photopeak ±10% window.

After completion of microSPECT images CT imaging was performed (energy: 75 kV/280 μA, matrix: 512×512) to identify anatomical structure. Compared with the microSPECT system, the CT system had a larger field of view, with a spatial resolution of ~60 μm. After in vivo imaging, the tissues were harvested and placed on a holder, and planar imaging was performed using 1 mm pinhole low energy high resolution collimators. Images were analyzed using Xeleris Functional Imaging Workstation (General Electric, Waukesha, Wis.). Several regions of interest (ROIs) were placed over selected organs to calculate average activity/pixel. Activities of each organ was expressed as % ID using the point sources.

CT projection images were reconstructed using commercial software (Cobra, Exxim Computing Corp., Pleasanton, Calif.), that implement a cone-beam reconstruction algorithm. MicroSPECT images were reconstructed through iterative reconstruction (5 iterations, 4 subsets) using system software and filtered post-reconstruction using Butterworth filter (cut-off: 0.5 Nyquist frequency, order: 6). SPECT images were smoothed by a low-pass Butterworth filter to reduce random noise. Reconstructed microSPECT images were reoriented according to the CT anatomical images, fused, and exported in "Analyze" format (Analyze, Mayo Clinic, Rochester, USA) for further processing using Amide (a Medical Imaging Data Examiner, amide.sf.net). ROIs were drawn around the aorta and other organs and the uptake was measured and expressed as counts per voxel and converted to % ID using point sources of known activity placed in the field of view.

Tissue Analysis

After microSPECT/CT imaging, the supra-renal abdominal aorta was rapidly cleaned from adherent tissues under stereoscopic microscope, and was frozen in OCT. In order to determine the maximal external diameter, 5 μm-thick serial sections of the abdominal aorta (typically 10 sections, 200-300 μm apart) were used for morphometric analysis (Fiji/ImageJ software, NIH) after hematoxylin and eosin staining. Adjacent tissues were processed to extract protein and RNA at the sites of maximum uptake observed on SPECT images, identified based on anatomical landmarks.

Zymography

Aortic tissue was lysed in a lysis buffer (NaCl 0.3 M, Tris 50 mM, Triton X-100 1%, cOmplete™ Protease Inhibitor Cocktail, Sigma-Aldrich), and protein concentration was measured using a colorimetric assay (Protein Assay Dye Reagent Concentrate, Bio-Rad; BioMate 3, Thermo Scientific). MMP activity was assessed in 1 μg of protein lysate using a fluorometric zymography assay (SENSOLYTE® 520 Generic MMP Activity Kit, AnaSpec), according to the manufacturer's instructions and presented in relative arbitrary units.

Quantitative Reverse Transcription Polymerase Chain Reaction

RNA was isolated from aortic tissue using GenElute Mammalian Total RNA Miniprep Kit (Sigma-Aldrich) and reverse-transcribed using QuantiTect Reverse Transcription Kit (Qiagen). Quantitative reverse transcription polymerase chain reaction analysis was performed with a 7500 Real-Time PCR System (Applied Biosystems) using the following primers and probe sets (MMP-2: Mm00439498_ml; MMP-9: Mm00442991_ml; MMP-12: Mm0050054_ml; CD68: Mm03047343_ml; β-actin: Mn00607939_sl, TaqMan Gene Expression Assays, Thermo Fisher Scientific), according to the manufacturers' instructions. CD68 and MMP gene expression were normalized to β-actin.

Mass Spectroscopy and NMR:

Mass spectra were recorded using electrospray ionization (ESI+/−) or Q-TOF high-resolution mass analyzers (Agilent). $^1$H and $^{13}$C NMR data were obtained using a 400 MHz spectrometer (Agilent), and TMS was used as an internal reference; chemical shifts were reported in parts per million (δ).

Radiochemistry and Stability Analysis

Radiolabeling quality control was performed by reverse phase radio-HPLC analysis (HPLC system 2489, Waters) with a flow rate of 1 mL/min using an analytical column (JUPITER® 4 μm Proteo 90 Å, Phenomenex) with gradients of solvent A (0.16% ammonium formate in aqueous solution) and solvent B (0.16% ammonium formate in 90% acetonitrile). The HPLC gradients were programmed as follows: 10% B for 2 min, 10-70% B in 5 min, 5 min 70% B and 70-90% B in 5 min. In vitro and in vivo stability of the tracer were analyzed by radio-HPLC following in vitro incubation in mouse blood at 37° C. for up to 5 hours, and from urine collected at 2 hours after tracer injection, respectively.

Statistical Analysis

All data are presented as mean±standard deviation. Mann-Whitney U test was used to compare data sets from two experimental groups. Two-way analysis of variance with post-hoc Bonferroni correction was used to compare blood activity between groups. Spearman's rank correlation was used to assess the significance of correlations (Prism 7, GraphPad). A P-value below 0.05 was considered statistically significant.

Example 1: Synthesis of 1, and Corresponding $^{99m}$Tc Complex ($^{99m}$Tc-1)

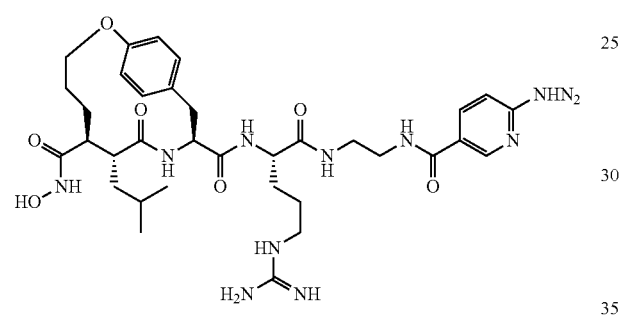

Synthesis of 1 used an anti-2,3-disubstituted succinic acid derivative, i.e. (2R,3S)-3-(tert-butoxycarbonyl)-2-iso-butyl-hex-5-enoic acid, with a protected macrocyclic acid I-7 as a key intermediate (Scheme 1). I-7 was reacted with an Arg fragment to give I-14 (Scheme 2). I-14 was further conjugated with Boc-HYNIC to afford 1 (Scheme 4).

Scheme 1.
Synthesis of a carboxylic acid-containing macrocyclic intermediate (I-7).

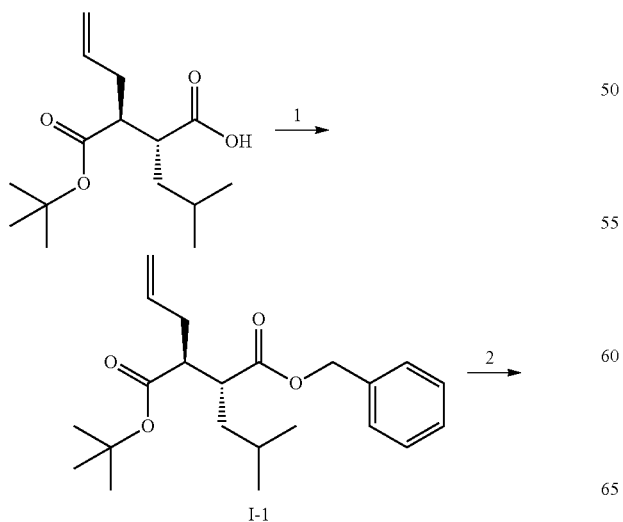

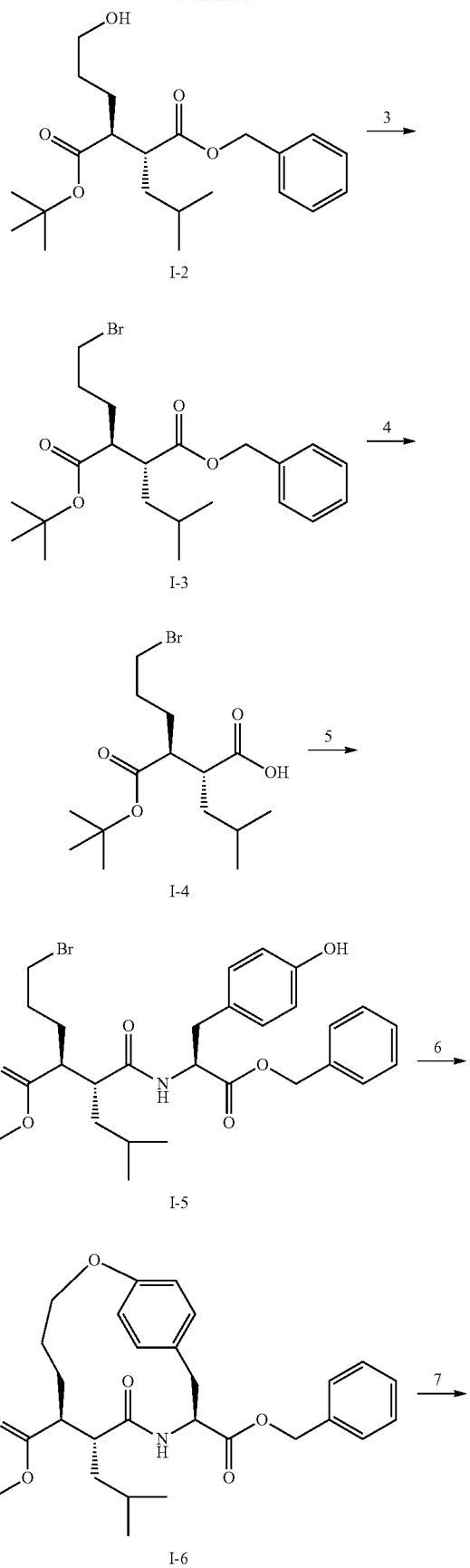

-continued

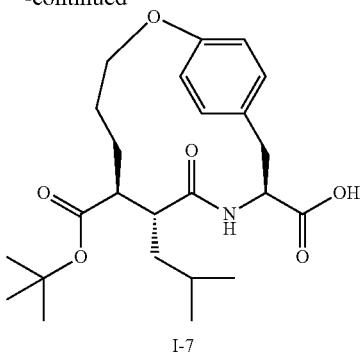

I-7

Reagents & Conditions: 1. BzBr/DBU/Toluene; 2. a) 9-BBN/THF; b) $H_2O_2/H_2O$; 3. $CBr_4/Ph_3P/DCM$; 4. Pd/C(10%)/$HCOONH_4/CH_3OH$; 5. H-Tyr-OBz/EDCI/HOBT/DMF; 6. $Cs_2CO_3$/acetonitrile; 7. Pd/C(10%)/$HCOONH_4/CH_3OH$.

Intermediate 1 (I-1)

To a stirred solution of (2R,3S)-3-(tert-butoxycarbonyl)-2-iso-butylhex-5-enoic acid (10.0 g, 95%, 35.1 mmol) and benzyl bromide (15 g, 85.9 mmol) in toluene (40 mL), were added dropwise 13.0 g (86 mmol) 1,8-diazabicyclo[5.4.0]undec-7-ene (DBU) in 20 mL toluene. The resulting mixture was stirred at room temperature for 2 h and then at 60° C. for 1 h. The toluene solution was separated from the precipitated solid residue. The residue was dissolved in water (20 mL), and extracted with ethyl acetate (20 mL×3). The combined toluene and ethyl acetate solution (100 mL) was washed with 1 N HCl (20 mL×2), water (20 mL×2) and brine (20 mL×2). It was dried over anhydrous $MgSO_4$ overnight, filtered and concentrated under vacuum. The resulting residue was purified by chromatography (silica gel, hexanes/ethyl acetate) to afford 9.0 g (71%) of the title compound as oil. ES-MS: Observed $[MH]^+$ 360.1, $[MNa]^+$ 383.2.

Intermediate 2 (I-2)

To a stirred solution of I-1 (9.0 g, 24.9 mmol) in 30 mL anhydrous THF cooled in an ice bath, was added dropwise 9-BBN in THF (200 mL, 100 mmol) over a period of 30 min. The mixture was further stirred at room temperature overnight. 10 mL water were added dropwise after the solution was cooled in an ice bath. A solution of 9.9 g NaOAc in water (30 mL) was added, followed by adding 30% $H_2O_2$ (30 mL) dropwise. The mixture was stirred at room temperature for 60 min and concentrated under vacuum. The resulting aqueous solution was extracted with ethyl acetate (20 mL×4). The combined toluene and ethyl acetate solution (100 mL) was washed with 1 N HCl (20 mL×2), water (20 mL×2), and brine (20 mL×2). After it was dried over anhydrous $MgSO_4$ overnight, the solution was filtered and concentrated under vacuum. The resulting residue was purified by silica gel chromatography (silica gel, ethyl acetate/hexanes) to give the title compound (7.2 g, 70%). ES-MS: observed $[MH\text{-tert-butyl}]^+$ 323.0, $[MNa]^+$ 401.1, $[MH\text{-tert-butyl-}H_2O]^+$ 305.2.

Intermediate 3 (I-3)

To a stirred solution of I-2 (7.0 g, 19.0 mmol) and $CBr_4$ (12.6 g, 38 mmol) in anhydrous DCM (30 mL), was added $Ph_3P$ (10.4 g, 40 mmol) in small portions for 30 min. The resulting mixture was stirred at room temperature for another 2 h, followed by adding 30 mL hexanes. The resulting mixture was transferred to a short column of silica gel for quick elution using DCM and hexanes (1:1). The desired fractions were combined and concentrated to get a crude product which was further purified by column chromatography (silica gel, hexanes/ethyl acetate). 5.1 g (63%) of the title compound was obtained. ES-MS: Observed double peak $[MNa]^+$ 463.0/465.2, $[M\text{-tert-butyl}]^+$ 385.0/387.0.

Intermediate 4 (I-4)

A mixture of I-3 (5.0 g, 11.3 mmol), Pd/C (2.0 g, 10%, wet) and $HCOONH_4$ (5 g) in 30 mL methanol was stirred at room temperature until the hydrogen gas evolved was observed. The mixture was stirred for another 10 min, filtered, followed by washing the Pd/C with methanol (5 mL×4). The combined methanol filtrate was concentrated and the residue was acidified with 1 N HCl solution. The product was extracted with ethyl acetate (20 mL×3). The solution was washed with water (10 mL×2) and brine (10 mL×2), dried over anhydrous $MgSO_4$, filtered, and concentrated. The product (3.1 g, 80%) obtained was used for the next step without further purification. ES-MS: Observed double peak $[MNa]^+$ 373.0/375.0, $[M\text{-tert-butyl-}H_2O]^+$ 277.0/279.0 (100%), $[MNa\text{-tert-butyl}]^+$ 318.0/320.0.

Intermediate 5 (I-5)

To a stirred solution of I-4 (3.0 g, 8.5 mmol), HOBT (1.7 g, 12.7 mmol), and Tyr-OBz (3.4 g, 12.7 mmol) in 20 mL anhydrous DMF cooled in ice bath, was added EDCI (2.4 g, 12.7 mmol). The resulting mixture was stirred at room temperature for another 2.5 h. The resulting mixture was concentrated under high vacuum and re-dissolved with ethyl acetate. The ethyl acetate solution was washed with water, 1 N HCl, water, 1 N $Na_2CO_3$ solution, water, and brine. The solution was dried over anhydrous $MgSO_4$, filtered, and concentrated under vacuum. The resulting residue was purified by chromatography (silica gel, ethyl acetate/hexanes). 3.8 g (74%) of the title compound was obtained. ES-MS: Observed $[MNa]^+$ double peak 626.0/628.0 and $[MH]^+$ 604.2/606.0. $^1H$ NMR (400 MHz, $CDCl_3$) δ 0.8 (6H, d, J=8 Hz), 1.01 (1H, m), 1.24 (2H, m), 1.45 (9H, s), 1.60-1.77 (4H, m), 2.36 (2H, m), 2.97 (1H, m), 3.09 (1H, m), 3.21 (1H, m), 3.35 (1H, m), 4.97 (1H, m), 5.16 (2H, m), 5.50 (1H, s), 6.01 (1H, m), 6.50-7.37 (9H, aromatic H); $^{13}C$ NMR (100 MHz, $CDCl_3$) δ 21.52, 23.96, 25.85, 28.21, 29.77, 30.60, 33.28, 37.64, 40.69, 48.42, 49.17, 53.15, 67.54, 81.41, 115.72, 127.70, 128.73, 128.75, 128.79, 130.51, 135.14, 155.09, 171.58, 173.42, 173.68.

Intermediate 6 (I-6)

To a stirred solution of $Cs_2CO_3$ (3.2 g, 23.4 mmol) in 500 mL anhydrous acetonitrile at 60° C., was added dropwise a solution of I-5 (3.0 g, 5.3 mmol) in 50 mL over a period of 1 h. The resulting mixture was stirred at 60° C. for another 3 h and concentrated under vacuum. The product was redissolved with ethyl acetate and filtered, followed by washing the solid with ethyl acetate for 5 times (10 mL×5). The combined ethyl acetate filtrate was washed with 1 N HCl solution, water, and brine. The solution was dried over anhydrous $MgSO_4$, filtered, and concentrated. The residue was purified by silica gel chromatography using (silica gel, $DCM\text{-}CH_3OH$) to yield the product (1.6 g, 60%). ES-MS: observed $[MH]^+$ 524.2, $[MNa]^+$ 546.2, $[MH\text{-tert-butyl}]^+$ 468, $[MCs]^+$ 656.2; $^1H$ NMR (400 MHz, $CDCl_3$) δ-0.47 (1H, m), 0.61 (1H, m), 0.75 (6H, m), 0.81 (1H, m), 1.21-1.55 (4H, m), 1.37 (9H, s), 1.86 (1H, m), 2.02 (1H, m), 2.52 (1H, m), 3.57 (1H, m), 4.04 (1H, m), 4.2 (1H, m), 5.11-5.24 (3H, m), 5.51 (1H, m), 6.94-7.40 (9H, aromatic H); $^{13}C$ NMR (100 MHz, $CDCl_3$) δ 21.29, 24.05, 25.61, 28.20, 29.93, 31.20, 37.85, 40.55, 49.45, 50.01, 51.61, 67.56, 73.91, 80.81, 120.52, 123.59, 128.67, 128.77, 128.83, 129.87, 131.44, 132.01, 135.21, 159.38, 171.73, 173.11, 174.01.

Intermediate 7 (I-7)

A mixture of I-6 (5.0 g, 9.5 mmol), 10% Pd/C (2.0 g), and HCOONH$_4$ (5 g) in 15 mL CH$_3$OH was stirred at room temperature for 2-3 h until the hydrogen gas evolved was observed. The mixture was further stirred for another 20 min and filtered, followed by washing the Pd/C with CH$_3$OH (5 mL×4). The methanol filtrate was concentrated and acidified with 1N HCl solution to get a residue, which was extracted with ethyl acetate. The solution was washed with water (10 mL×2) and brine (10 mL×2). The solution was dried over anhydrous MgSO$_4$, filtered, and concentrated. The product (3.7 g, 90%) was used for the next step without further purification. LC-MS: Observed [MH]$^+$ 434.2, [MNa]$^+$ 456.2.

Scheme 2.
Synthesis of an amino-containing macrocyclic hydroxamate (I-14).

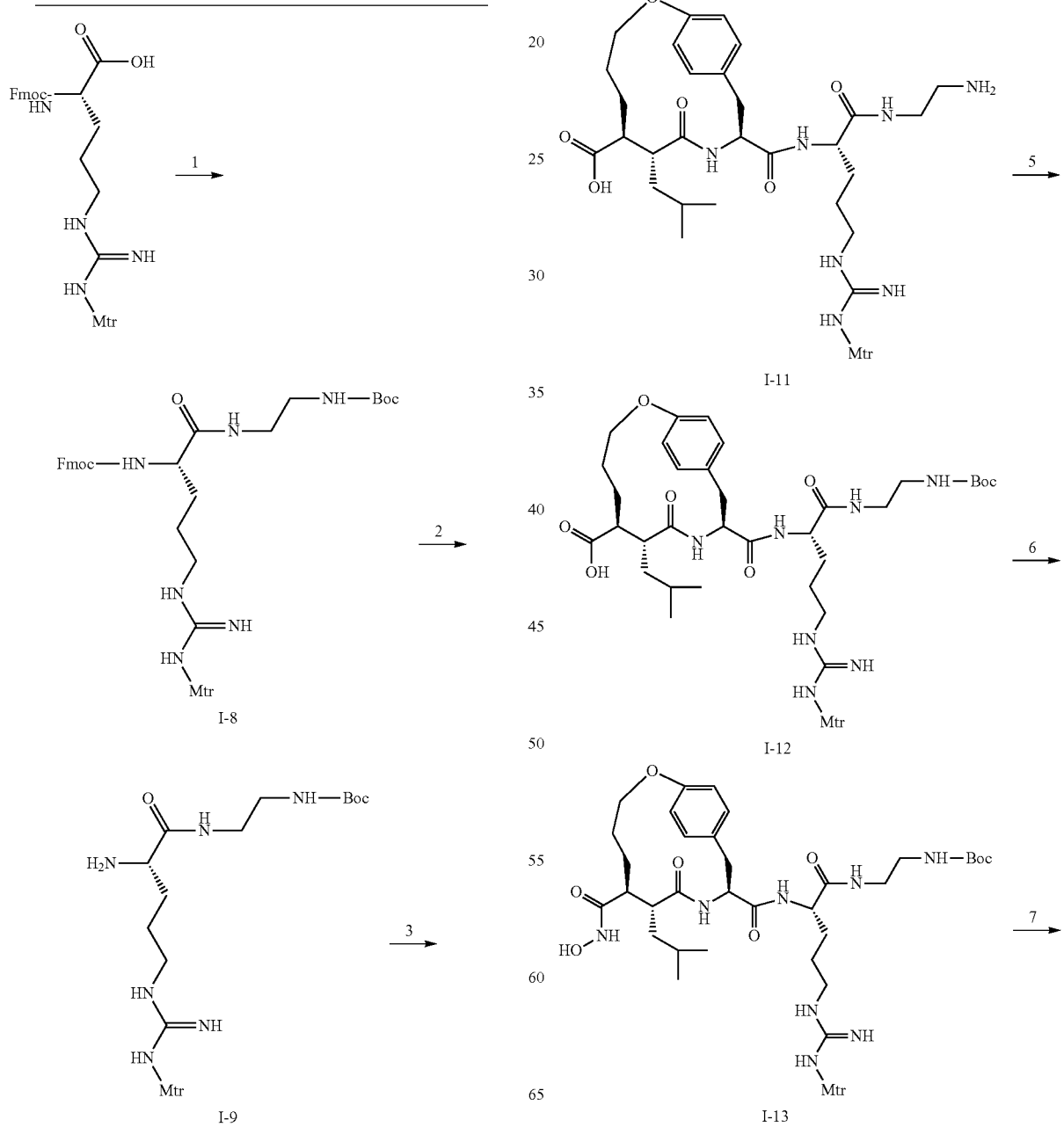

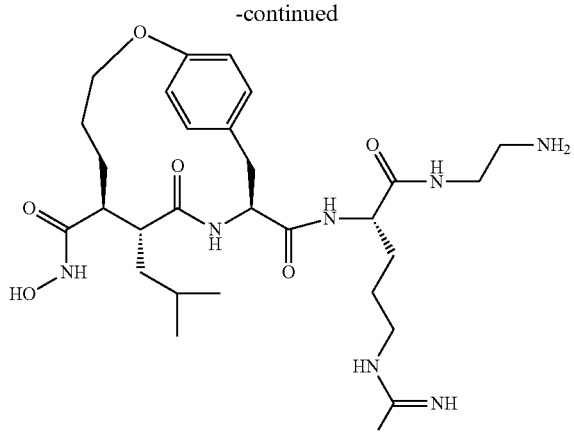

I-14

Reagents & Conditions: 1. NH$_2$CH$_2$CH$_2$NH—Boc/HOBT/EDCI/DMF; 2. Piperidine/DCM; 3. I-7/EDCI/HOBT/DMF; 4. TFA/DCM; 5. (Boc)$_2$O/Na$_2$CO$_3$/water/dioxane; 6. a) HATU/HOAT/DIEA/DMF; b) TBDMS—ONH$_2$; 7. TFA/water/TIS/phenol.

Intermediate 8 (I-8)

A mixture of 1.2 g Fmoc-Arg(Mtr)-OH (1.97 mmol), 0.32 g (2.36 mmol) HOBT, and 0.38 g (2.36 mmol) NH$_2$CH$_2$CH$_2$NHBoc was dissolved in 5 mL anhydrous DMF and cooled at 0~5° C. in ice bath, followed by adding 543.0 mg EDCI (2.83 mmol). After stirred at room temperature overnight, the mixture was concentrated under high vacuum. The residue was triturated with 1 N HCl, filtered, and washed with 1 N HCl, 1 N Na$_2$CO$_3$, and H$_2$O. The solid product was dried to give 1.3 g (90%) of the title compound. ES-MS: Observed [MH]$^+$ 529.6.

Intermediate 9 (I-9)

1.0 g I-8 (1.33 mmol) was dissolved in 7 mL DCM and 3 ml piperidine. After stirred at room temperature for 30 min, the mixture was concentrated under high vacuum. The residue was purified by flash column chromatography using DCM and methanol to give 0.52 g (75%) of the title compound. ES-MS: Observed [MH-Boc]$^+$ 429.2.

Intermediate 10 (I-10)

A mixture of 200.0 mg (0.46 mmol) I-9, 291.0 mg (0.55 mmol) H-Arg(Mtr)-NHCH$_2$CH$_2$NH—Boc, and 74.8 mg (0.55 mmol) HOBT was dissolved in 5 mL DMF and cooled at 0~5° C. in an ice bath, followed by adding 126.5 mg (0.66 mmol) EDCI. The mixture was stirred at room temperature overnight and concentrated. The residue was dissolved in 10 mL CH$_2$Cl$_2$, washed with 1 N HCl, H$_2$O, and brine. The DCM solution was dried over MgSO$_4$, filtered, and concentrated. The product was purified by flash column chromatography using DCM and methanol to give 260 mg (60%) of the title compound. ES-MS: Observed [MH-Boc]$^+$ 845.8, [MH$_2$-tert-butyl]$^{2+}$ 394.7.

Intermediate 11 (I-11)

0.2 g (0.21 mmol) I-10 were dissolved in 8 mL TFA and 2 mL DCM. After stirred at room temperature for 2 h, the solution was concentrated and dried under vacuum to give 0.18 g (98%) of the title compound. ES-MS: Observed [MH]$^+$ 788.3, [MH$_2$]$^{2+}$ 394.8.

Intermediate 12 (I-12)

0.15 g (0.16 mmol) I-11 were dissolved in 5 mL dioxane and 5 mL 1 N Na$_2$CO$_3$ solution. The mixture was stirred in ice bath, followed by adding 70.0 mg (0.32 mmol) (Boc)$_2$O. After stirred at room temperature for 2 h, the solution was concentrated and the residue was acidified with 1 N HCl to pH 3. The product was extracted with DCM, washed with water, and dried over MgSO$_4$. The filtrate was concentrated to give the title compound (135.0 mg, 95%). ES-MS: Observed [MH]$^+$ 888.3.

Intermediate 13 (I-13)

A mixture of 100.0 mg (0.11 mmol) I-12, 30.4 mg (0.22 mmol) HOAT, and 83.6 mg (0.22 mmol) HATU, and 57.0 mg (0.44 mmol) DIEA was dissolved in 5 mL anhydrous DMF. The mixture was stirred at room temperature for 20 min, followed by adding 147.2 mg (1.0 mmol) TBDMS-ONH$_2$. The mixture was stirred at room temperature overnight and concentrated under vacuum. The residue was triturated with 1 N HCl, filtered, and washed with water, 1 N Na$_2$CO$_3$, and brine. The product was further purified by column chromatography to give 30.0 mg (30%) of the title compound. ES-MS: Observed [MH]$^+$ 903.2, [MNa]$^+$ 925.4.

Intermediate 14 (I-14)

20 mg (0.022 mmol) I-13 was dissolved in a mixture of 9.0 mL TFA, 0.5 mL H$_2$O, 0.25 mL TIS, and 0.25 g phenol. The mixture was stirred at room temperature overnight and concentrated under vacuum. The residue was added into 10 mL cooled diethyl ether. The precipitated product was collected by centrifugation and purified by semi-preparative HPLC using an eluent of aqueous acetonitrile. The desired fractions were collected and lyophilized to give the title compound (5.4 mg, 30%). ES-MS: Observed [MH]$^+$ 591.4, [MH$_2$]$^{2+}$ 296.3, [M$_2$H$_3$]$^{3+}$ 394.6.

Scheme 3. Synthesis of Boc-HYNIC (I-16).

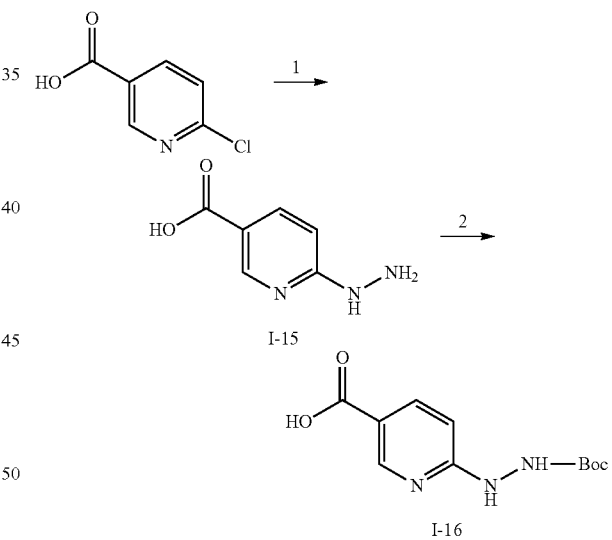

Reagents & Conditions: 1. NH$_2$NH$_2$/H$_2$O/95~100° C.; 2. (Boc)$_2$O/Na$_2$CO$_3$/water/1,4-dioxane Intermediate 15 (I-15)

A mixture of 6-chloronicotinic acid (10.0 g, 63.4 mmol), hydrazine (20 mL), and water (20 mL) was refluxed at 95~100° C. for 4 h. The mixture was concentrated under vacuum and the residue was dissolved in 40 mL water. The resulting solution was acidified with 1 N HCl to reach a pH 5~5.5. The solution was kept in a refrigerator overnight. The precipitated solid was collected by filtration, washed with cold water (10 mL×2) and ether (10 mL×2). The solid was dried to give 8.5 g (87%) of the title compound. ES-MS: Observed [MH]$^+$ 154.1.

Intermediate 16 (I-16)

A mixture of 4.0 g I-15 and 8.0 g $Na_2CO_3$ was stirred in 60 mL 1,4-dioxane and 60 mL water and cooled in ice bath. 8.2 g $Boc_2O$ were added, and the mixture was further stirred at room temperature for 5 h. The mixture was concentrated and the solid residue was acidified with 1 N HCl solution to get some precipitated solid which was collected by filtration and dried to give the title compound.

Intermediate 17 (I-17)

A mixture of 10.0 mg (0.039 mmol) I-16, 5.5 mg HOAT (0.039 mmol), and 15.0 mg HATU (0.039 mmol) was dissolved in 1 mL anhydrous DMF, followed by adding 10.0 mg (0.078 mmol) DIEA. The mixture was stirred at room temperature for 30 min. To the resulting solution was added a solution of 16.0 mg (0.0195 mmol) I-14 and 5 μL (3.71 mg, 0.028 mmol) DIEA in 0.5 mL anhydrous DMF. The resulting solution was stirred at room temperature for 1 h and concentrated under vacuum. The residue was triturated with 1 N HCl, filtered, and washed with 1 N $Na_2CO_3$ and water. The solid product was used in the next reaction without further purification. ES-MS: Observed $[MH]^+$ 826.2, $[MH_2]^{2+}$ 413.6.

Compound 1 ((6S,7R,10S)—$N^{10}$—((S)-5-guanidino-1-((2-(6-hydrazinylnicotinamido)ethyl)amino)-1-oxopentan-2-yl)-$N^6$-hydroxy-7-isobutyl-8-oxo-2-oxa-9-aza-1(1,4)-benzenacycloundecaphane-6,10-dicarboxamide)

I-17 was dissolved in a mixture of 4.5 mL TFA, 0.25 mL $H_2O$, 0.125 mL TIS, and 0.125 g phenol. The mixture was stirred at room temperature for 30 min and concentrated under vacuum. The residue was added into 10 mL cooled diethyl ether. The precipitated product was collected by centrifugation and purified by semi-preparative HPLC using an eluent of aqueous acetonitrile. The desired fractions were collected and lyophilized to give the title compound (3.0 mg, 16%) as confirmed by both LC-MS and analytical HPLC. ES-MS: Observed $[MH]^+$ 726.3, $[MH_2]^{2+}$ 363.7.

Scheme 4. Synthesis of illustrative Arg-containing macrocyclic hydroxamate-HYNIC conjugate 1.

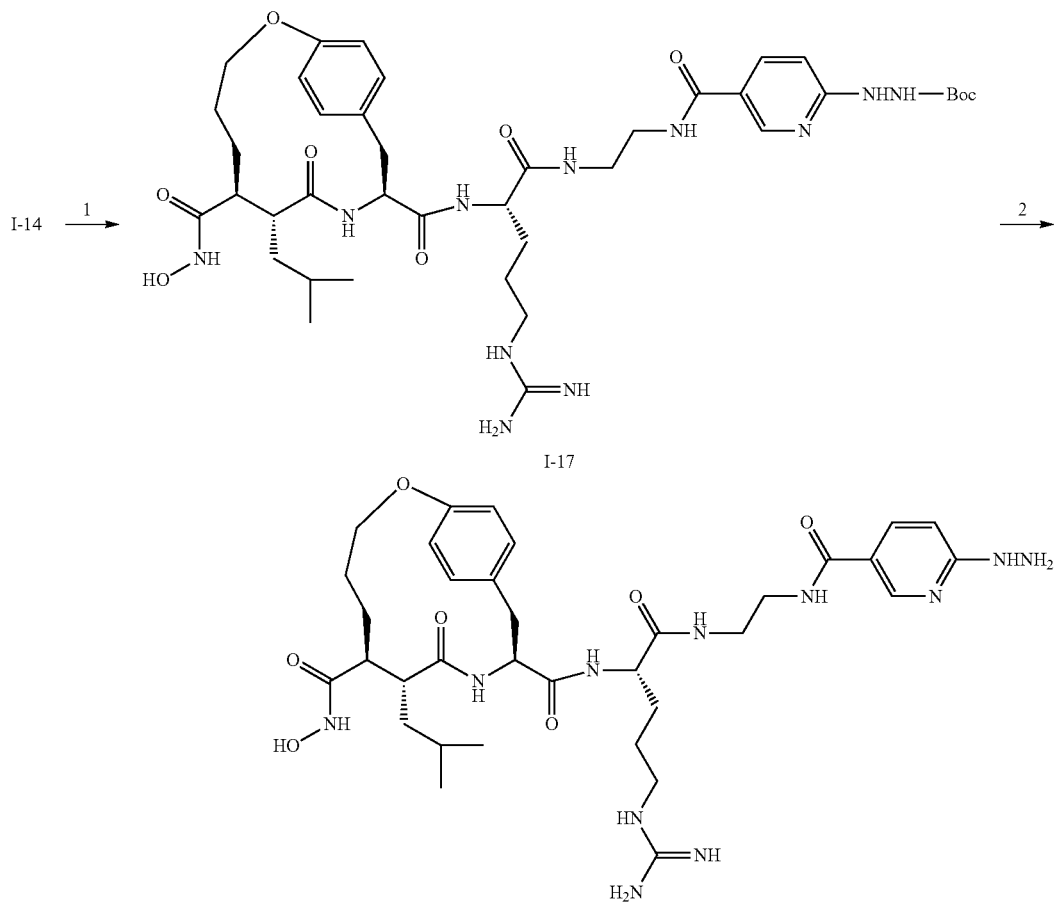

Reagents & Conditions: 1. Boc—HYNIC/HATU/HOAT/DIEA/DMF; 2. TFA/water/TIS/phenol.

Compound $^{99m}$Tc-1

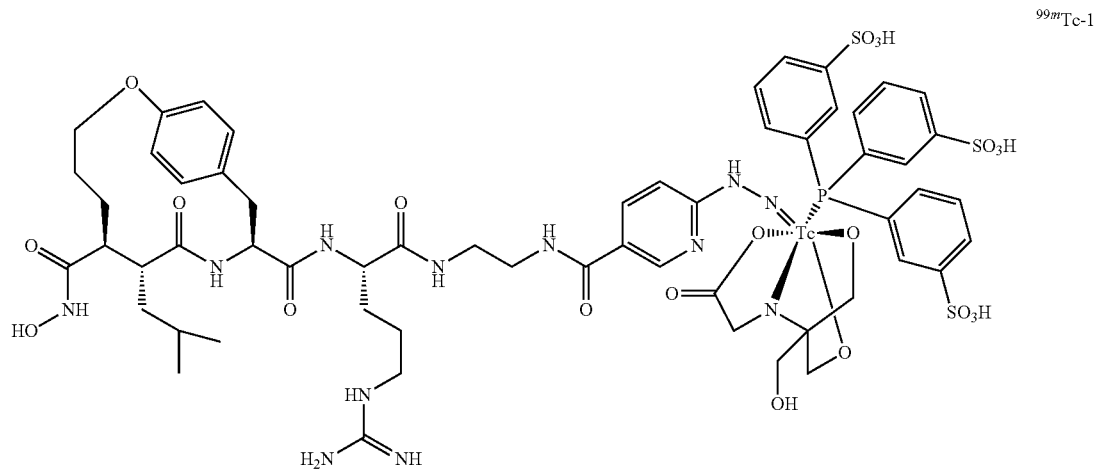

$^{99m}$Tc-1

1 was labeled with $^{99m}$Tc by heating $^{99m}$Tc in a vehicle solution containing tricine and 3,3',3''-phosphanetriyltris (benzenesulfonic acid) trisodium salt (TPPTS) in high purity and yield. Typically, 2 μg of 1 was mixed 5-10 mCi/100 μL $^{99m}$TcO$_4$, followed by addition of with 200 μL of the vehicle solution in a vial. The mixture was heated at 95° C. for 10 min, and cooled to room temperature to yield the $^{99m}$Tc-labeled product as analyzed by radio-HPLC. Radio-HPLC analysis was performed using Waters RP-HPLC (Milford, Mass.) on a reverse-phase analytical column (Phenomenex, Jupiter 4μ Proteo 90A, 250×4.6 mm, 4 micron) with a gradient from 10% to 70% aqueous acetonitrile containing 25 mM ammonium formate at a flow rate of 1 mL/min over 40 min.

Example 2: Synthesis of 2, and Corresponding Cu Complex (Cu-2)

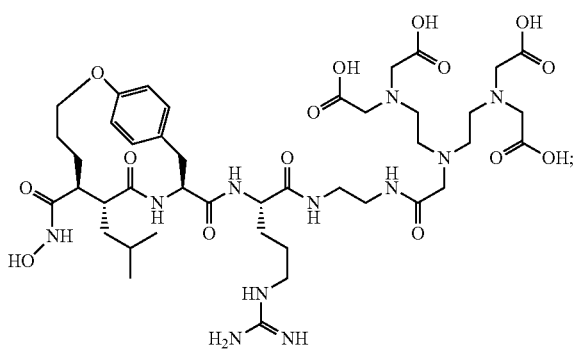

2

(S)-1-amino-14-(2-(bis(carboxymethyl)amino) ethyl)-17-(carboxymethyl)-6-((6S,7R,10S)-6-(hydroxycarbamoyl)-7-isobutyl-8-oxo-2-oxa-9-aza-1(1,4)-benzenacycloundecaphane-10-carboxamido)-1-imino-7,12-dioxo-2,8,11,14,17-pentaazanonadecan-19-oic acid Scheme 5. Synthesis of DTPA conjugate 2.

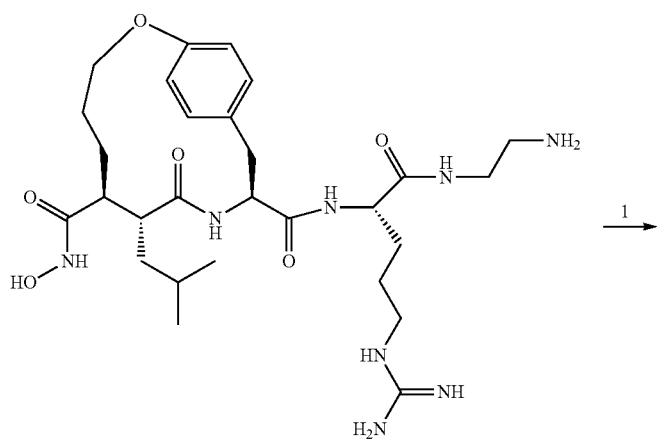

I-14

-continued

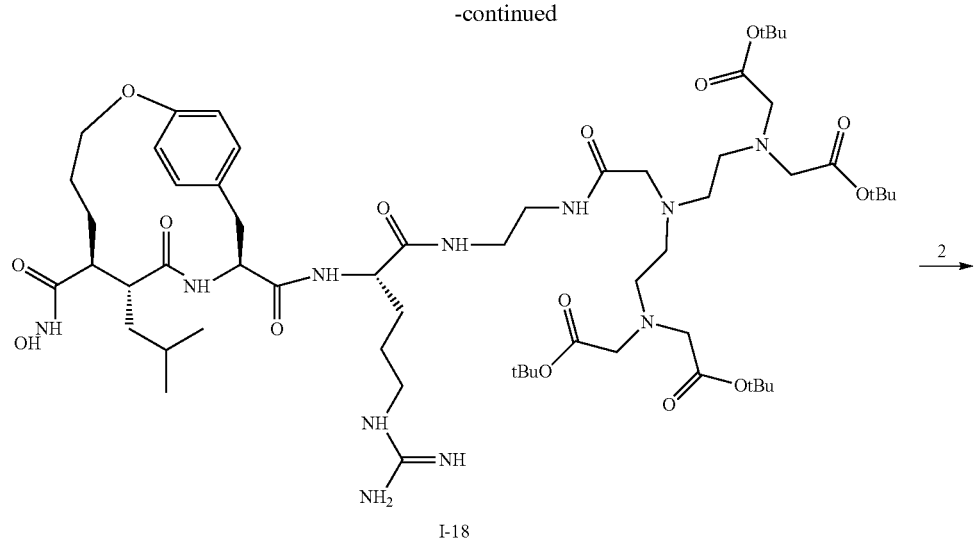

I-18

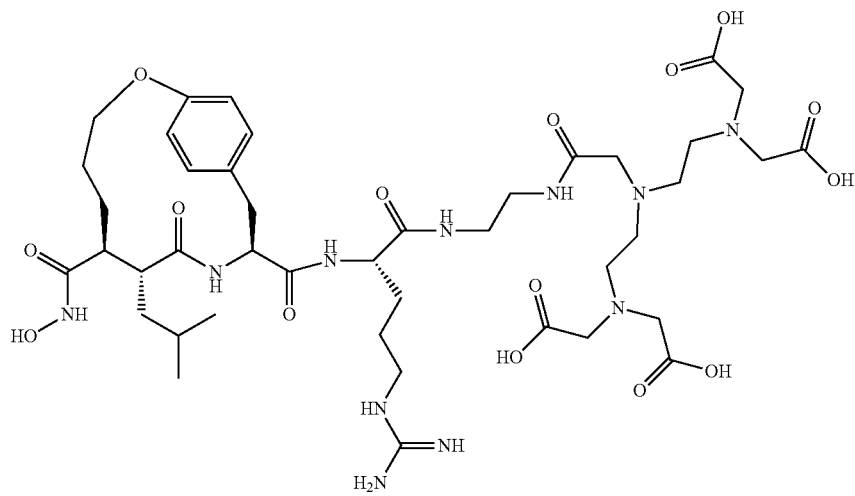

2

Reagents & conditions: 1. DTPA-tetra(t-Bu ester)/HOAT/HATU/DIEA/DMF; 2. TFA/water/phenol/TIS Intermediate 18 (I-18)

DTPA-tetra (t-Bu ester) (20 mg, 0.032 mmol), HOAT (5.2 mg, 0.038 mmol), HATU (14.4 mg, 0.038 mmol), and DIEA (10.0 mg, 0.076 mmol) was mixed in 2 mL anhydrous DMF. The mixture was stirred at room temperature for 30 min, followed by addition of a solution of I-14 (20 mg, 0.02 mmol) and DIEA (5 μL) in 0.5 mL DMF. The mixture was stirred at room temperature for 3 h and concentrated under vacuum. The residue was triturated with water, filtered, and washed sequentially with 1 N HCl, water, 1 N $Na_2CO_3$, and brine. The solid collected was used in the next reaction without further purification. ES-MS: Observed $[MH]^+$ 1190.6, $[MNa]^+$ 1212.6, $[MH_2]^{2+}$ 595.8, $[MH_2\text{-tert-butyl}]^{2+}$ 567.8.

Compound 2

I-18 was dissolved in a mixture of 9.0 mL TFA, 0.5 mL $H_2O$, 0.25 mL TIS, and 0.25 g phenol. The mixture was stirred at room temperature overnight and concentrated under vacuum. The residue was added to 10 mL diethyl ether and cooled. The precipitate was collected by centrifugation and purified by semi-preparative HPLC using gradient elution with aqueous acetonitrile. The desired fractions were identified by LC-MS, combined, and lyophilized to give the title compound 2 (6.0 mg, 21%) as confirmed by both LC-MS and analytical HPLC. ES-MS: Observed $[ME]^+$ 966.4, $[MH_2]^{2+}$ 483.8, $[MH_3]^{3+}$ 322.8.

Preparation of Cu-2 Complex
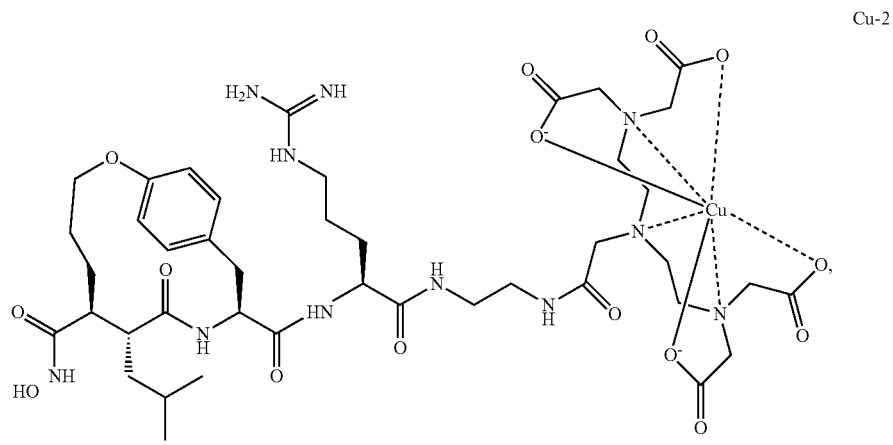
DTPA conjugate 2 (30 µg) was dissolved in 50% acetonitrile (30 µL). To this solution were added ammonia (1 µL) and CuCl$_2$ (5 µg) in 50% acetonitrile (30 µL). The mixture was swirled at room temperature for 30 min. LC-MS analysis confirmed the Cu-complexation with 2: [MCuH$_2$]$^{2+}$ 514.2, [MCuH$_3$]$^{3+}$ 343.2.
Example 3: Synthesis of 3, and its Corresponding Cu-3
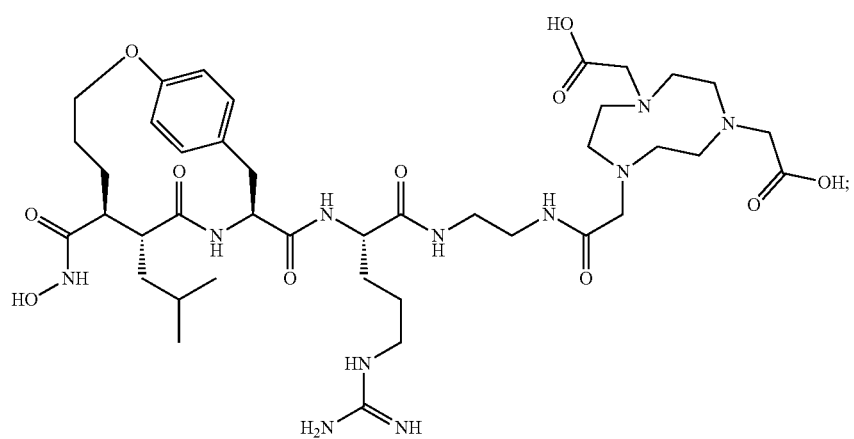

2,2'47-(2-((2-((S)-5-guanidino-2-06S,7R,10S)-6-(hydroxycarbamoyl)-7-isobutyl-8-oxo-2-oxa-9-aza-1(1,4)-benzenacycloundecaphane-10-carboxamido)pentanamido)ethyl)amino)-2-oxoethyl)-1,4,7-triazonane-1,4-diyl)diacetic acid
Scheme 6. Synthesis of NOTA conjugate (3).
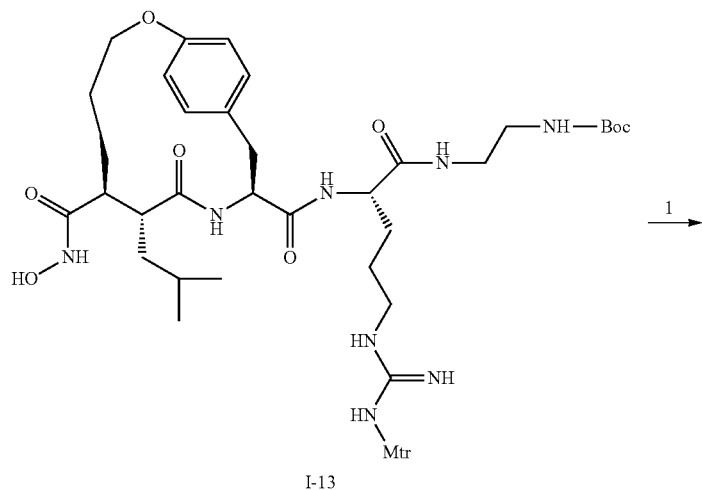
I-13
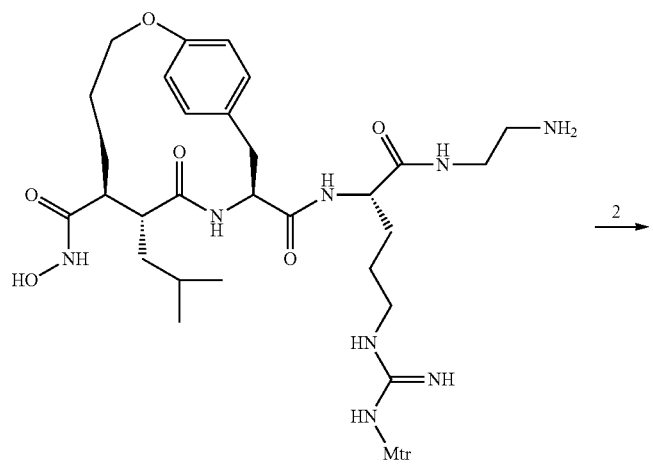
I-19
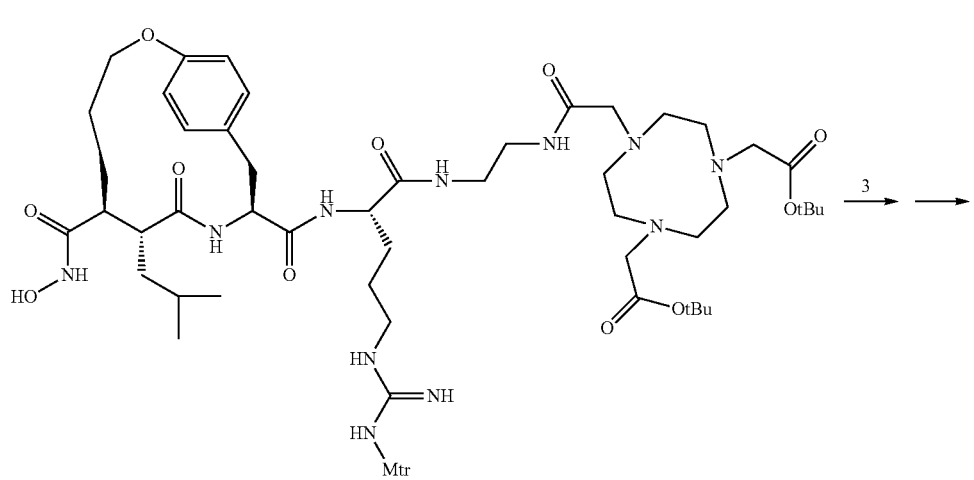
I-20

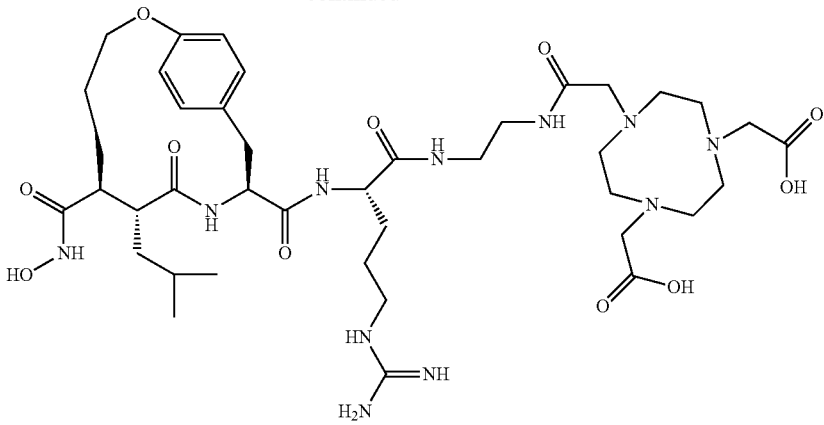

Reagents & conditions:
1. TFA/DCM;
2. NOTA-bis(t-Bu ester)/HOBT/EDCI/DMF;
3. TFA/water/phenol/TIS Intermediate 19 (I-19)

50.0 mg (0.055 mmol) I-13 were dissolved in 5.0 mL TFA, 5 mL DCM. The mixture was stirred at room temperature for 3 h and concentrated under vacuum, and dried to give 50.0 mg (100%) of the title compound. ES-MS: Observed $[MH]^+$ 803.3, $[MH_2]^{2+}$ 402.2.

Intermediate 20 (I-20)

A mixture of 13.3 mg (0.032 mmol) NOTA-bis(t-Bu ester), 5.2 mg (0.038 mmol) HOBT, and 8.8 mg (0.046 mmol) EDCI was dissolved in 1 mL anhydrous DMF. The mixture was stirred at room temperature for 30 min, followed by adding a solution of 10 mg (0.01 mmol) I-19 and 3 μL DIEA in 0.5 mL DMF. The mixture was stirred at room temperature overnight and concentrated under vacuum. The residue was triturated with water, filtered, and washed with 1 N HCl, water, 1 N $Na_2CO_3$, and brine. The solid product collected was used in the next reaction without further purification. ES-MS: Observed $[MH_2]^{2+}$ 600.8, $[MH_3]^{3+}$ 401.0.

Compound 3

10 mg I-20 were dissolved in a mixture of 4.5 mL TFA, 0.25 mL $H_2O$, 0.125 mL TIS, and 0.125 g phenol. The mixture was stirred at room temperature overnight and concentrated under vacuum. The residue was added into 10 mL cooled diethyl ether. The precipitated product was collected by centrifugation and purified by semi-preparative HPLC using gradient elution with aqueous acetonitrile from 5% to 50% over 20 min. The desired fractions were identified by LC-MS, combined and lyophilized to give the title compound (2.0 mg, 15%) as confirmed by both LC-MS and analytical HPLC. ES-MS: Observed $[MH]^+$ 876.4, $[MH_2]^{2+}$ 438.7.

Preparation of Cu-3 Complex

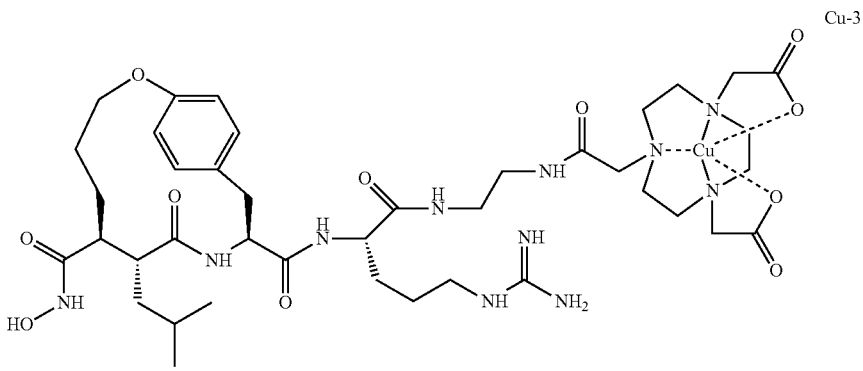

Cu-3

A solution of 30 μg (30 μL) the NOTA conjugate, 1 μL ammonia, and 30 μL (5 μg) CuCl₂ solution in 30 μL 50% acetonitrile was swirled at room temperature for 30 min. LC-MS analysis confirmed the Cu-complexation with 3: [MCuH]⁺ 937.2, [MCuH₂]²⁺ 469.2.
Example 4: Synthesis of Compounds of Formula II
Scheme 7. Synthesis of Arg-containing macrocyclic hydroxamate 19.
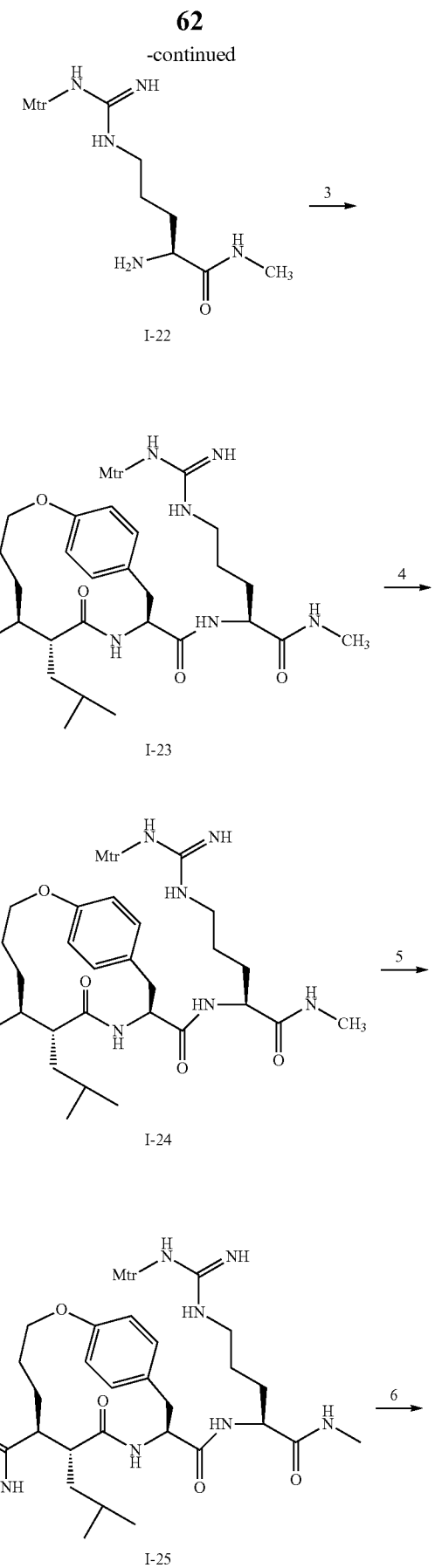

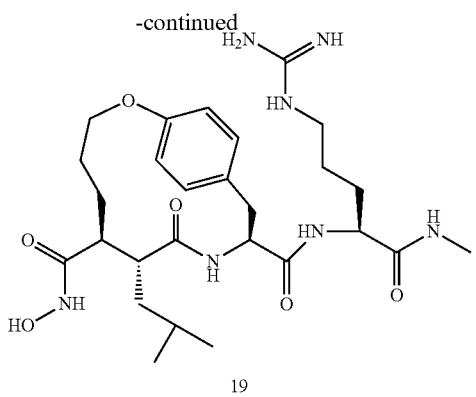

Reagents & conditions:
1. CH3NH2/EDCI/HOBT/DMF;
2. Piperidine/DCM;
3. I-7/HOBT/EDCI/DMF;
4. TFA/DCM;
5. a) HOAT/HATU/DIEA/DMF;
   b) TBDMS—ONH2;
6. TFA/water/TIS/phenol.

Intermediate 21 (I-21)

A mixture of 1.2 g Fmoc-Arg(Mtr)-OH (1.97 mmol), 0.27 g HOBT (2.0 mmol), 2 mL (2 M) CH3NH2 in THF (4.00 mmol) was dissolved in 5 mL anhydrous DMF and cooled at 0~5° C. in ice bath, followed by adding 600 mg EDCI (3.1 mmol). The mixture was stirred at room temperature overnight and concentrated under high vacuum. The residue was triturated with 1 N HCl, filtered, and further washed with 1 N HCl, 5 N Na2CO3, and H2O. The solid was dried to give 1.03 g (84%) of the title compound. ES-MS: Observed [MH]+ 622.2.

Intermediate 22 (I-22)

1.0 g of I-21 obtained above was dissolved in 10 mL DCM and 3 mL piperidine. The mixture was stirred at room temperature for 30 min and concentrated under vacuum. The product was purified by flash column chromatography using DCM and its mixture of 2% methanol as eluents to give the title compound (0.54 g, 85%). ES-MS: Observed [MH]+ 400.2, [M–H]− 398.1.

Intermediate 23 (I-23)

A mixture of 200.0 mg (0.46 mmol) I-7, 219.7 mg (0.55 mmol) I-22, and 115.0 mg (0.55 mmol) HOBT were dissolved in 5 mL DMF and cooled at 0~5° C. in an ice bath, followed by adding 100 mg (0.6 mmol) EDCI. The mixture was stirred at room temperature overnight and concentrated. The residue was dissolved in 10 mL CH2Cl2, washed with 1N HCl, H2O, and brine. The DCM solution was dried over MgSO4, filtered, and concentrated. The product was purified by flash column chromatography using DCM and its mixture of 2% methanol to give the title compound (300.0 mg, 80%). ES-MS: Observed [MH]+ 815.4.

Intermediate 24 (I-24)

250 mg of I-23 were dissolved in 4 mL TFA and 1 mL DCM. After stirred at room temperature for 2 h, the solution was concentrated and dried under vacuum to get the title compound in a quantitative yield. ES-MS: Observed [MH]+ 759.3, [MH2]2+ 392.1.

Intermediate 25 (I-25)

A mixture of 200 mg (0.26 mmol) I-24, 86.0 mg (0.6 mmol) HOAT, and 236.0 mg (0.6 mmol) HATU, and 16.0 mg (0.9 mmol) DIEA was dissolved in 4 mL anhydrous DMF. The mixture was stirred at room temperature for 20 min, followed by adding 137.0 mg (0.93 mmol) TBDMS-ONH2. The mixture was stirred at room temperature overnight and concentrated. The residue was triturated with 1 N HCl, filtered, and washed with 1 N Na2CO3, water, and brine. The product was further purified by flash column chromatography to give 100.0 mg (50%) of the title compound.

Compound 19

50 mg (0.065 mmol) I-25 was dissolved in a mixture of 9.0 mL TFA, 0.5 mL H2O, 0.25 mL TIS, and 0.25 g phenol. The mixture was stirred at room temperature overnight and concentrated under vacuum. The residue was added into 10 mL cooled diethyl ether. The precipitated product was collected by centrifugation and purified by semi-preparative HPLC using an eluent of aqueous acetonitrile. The desired fractions were collected and lyophilized to give the title compound (10.0 mg, 22%; (6S,7R,10S)—N10-((S)-5-guanidino-1-(methylamino)-1-oxopentan-2-yl)-N6-hydroxy-7-isobutyl-8-oxo-2-oxa-9-aza-1(1,4)-benzenacycloundecaphane-6,10-dicarboxamide) as confirmed by both LC-MS and analytical HPLC. ES-MS: Observed [MH]+ 562.3, [MH2]2+ 281.7, [M–H]− 560.2.

Scheme 8. Synthetic scheme of compound 20.

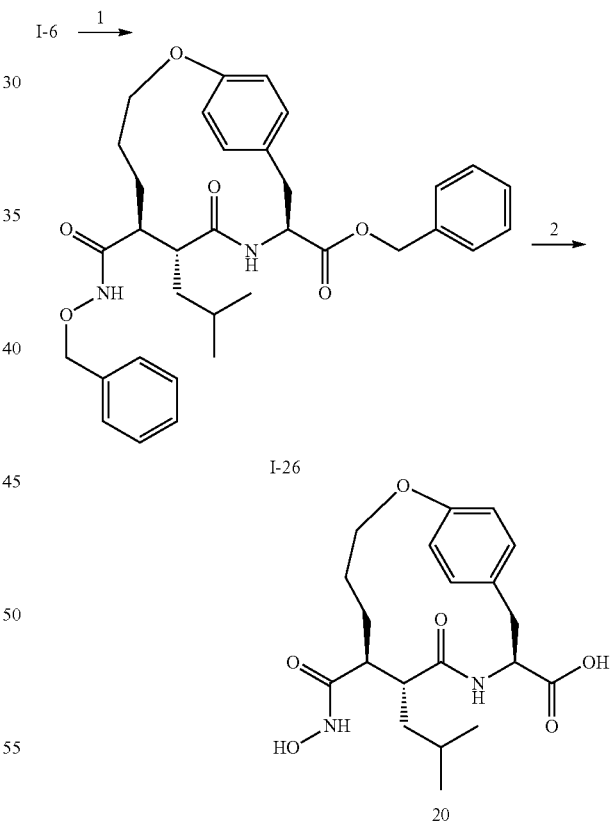

Reagents and conditions: 1. i) TFA, DCM, ii) O-benzylhydroxylamine hydrochloride, HBTU, NMM, DMF; 2. Pd/C, H2, MeOH Intermediate 26 (I-26)

The tert-butyl ester (I-6, 67 mg) was dissolved in DCM (1.6 mL) followed by addition of TFA (1.6 mL). The reaction mixture was stirred at room temperature for 1 h. The solvent was removed and dried under vacuum. The resulting acid, O-benzylhydroxylamine hydrochloride (67 mg), and HBTU (58.3 mg) was dissolved in DMF (0.8 mL) followed by addition of DIEA (112 µL). The reaction was stirred at room temperature overnight and quenched with 10% citric acid. Organic phase was washed with 1 N HCl, water, saturated NaHCO$_3$, and brine. After drying (MgSO$_4$) and concentration, I-26 was purified by silica gel column chromatography (EtOAc:Hexanes=1:2) to afford 67% product; Q-TOF-MS (ESI) m/z 392.2075 (calcd. 572.29 for C$_{34}$H$_{40}$N$_2$O$_6$ [M]+); $^1$H NMR (400 MHz, CD$_3$OD) δ-0.135 (1H, m), 0.82 (6H, m), 0.96 (2H, m), 1.12 (2H, m), 1.46 (6H, m), 1.94 (1H, m), 2.12 (1H, m), 2.63 (1H, m), 3.33 (2H, m), 3.48 (1H, m), 4.12 (1H, m), 4.89 (2H, m), 1.72 (2H, m), 1.81 (1H, m), 2.15 (1H, m), 2.57 (1H, m), 2.74 (1H, m), 3.63 (1H, dd, J=4 and 12 Hz), 4.14 (1H, m), 4.35 (1H, m), 5.16-5.30 (3H, m), 5.72 (1H, d, J=6 Hz), 6.98-8.07 (14H, aromatic H); $^{13}$C NMR (100 MHz, CD$_3$OD) δ 21.18 24.03 25.68, 29.85, 30.01, 31.41, 37.89, 41.06, 47.27, 49.01, 51.84, 67.76, 107.96, 120.44, 120.80, 123.65, 125.02, 128.47, 128.73, 128.89, 129.02, 130.08, 131.48, 132.19, 135.10, 143.53, 159.32, 171.45, 171.51, 171.63.

Compound 20 ((6S,7R,10S)-6-(hydroxycarbamoyl)-7-isobutyl-8-oxo-2-oxa-9-aza-1(1,4)-benzenacycloundecaphane-10-carboxylic acid)

The benzylhydroxamate (I-26, 41 mg) was dissolved in MeOH (3 mL), and 10% Pd/C (~7 mg) was added. The reaction was stirred under H$_2$ (balloon) for 3 h. The Pd/C was removed by passing through celite pad, and the solvent was removed by a rotary evaporator. Compound 20 was further purified by recrystallization with acetonitrile (~50% yield); Q-TOF-MS (ESI) m/z 392.2075 (calcd. 392.19 for C$_{20}$H$_{28}$N$_2$O$_6$ [M]+); $^1$H NMR (400 MHz, CD$_3$OD) δ-0.43 (1H, m), 0.715 (1H, m), 0.805 (6H, m), 0.89 (1H, m), 1.25-1.49 (6H, m), 1.94 (1H, m), 2.12 (1H, m), 2.63 (1H, m), 3.33 (2H, m), 3.48 (1H, m), 4.12 (1H, m), 4.89 (1H, m), 6.86-7.21 (4H, aromatic H); $^{13}$C NMR (100 MHz, CD$_3$OD) δ 14.43, 21.75, 23.70, 24.54, 26.62, 31.37, 32.27, 32.75, 38.29, 42.02, 49.47, 49.57, 49.85, 74.58, 111.42, 121.39, 123.85, 130.39, 133.60, 134.41, 160.24, 175.68.

Example 5: Synthesis of 17 and 18

Scheme 8. Synthesis of 17.

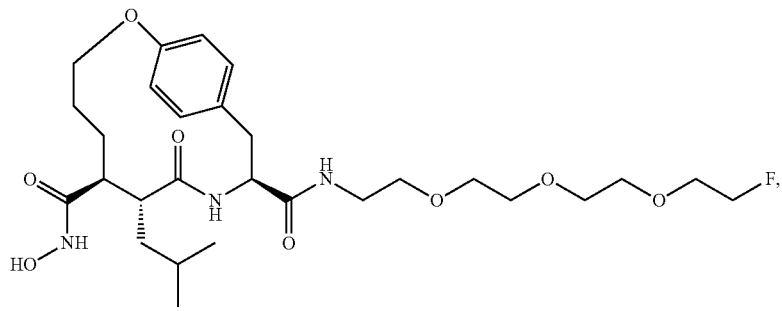

17

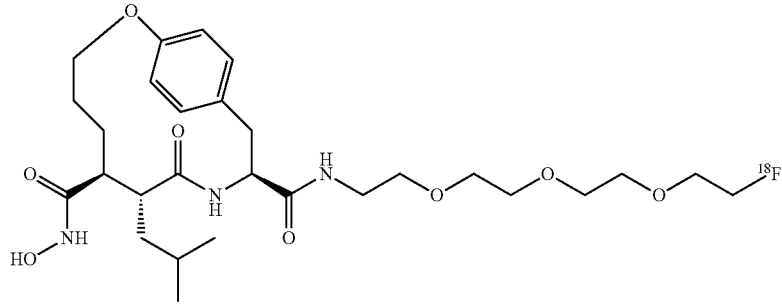

18

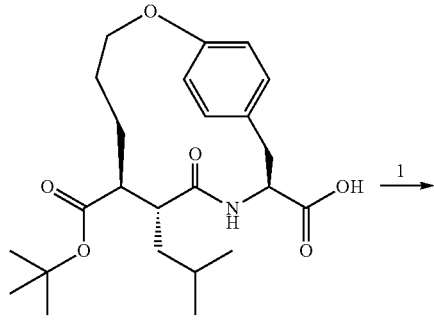

I-7

-continued
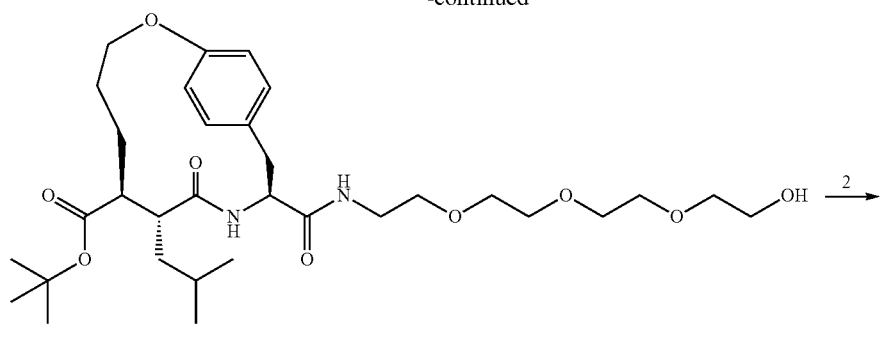
I-27
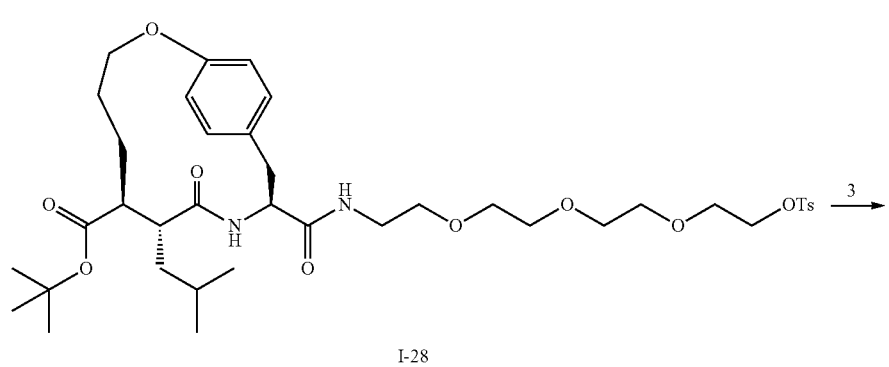
I-28
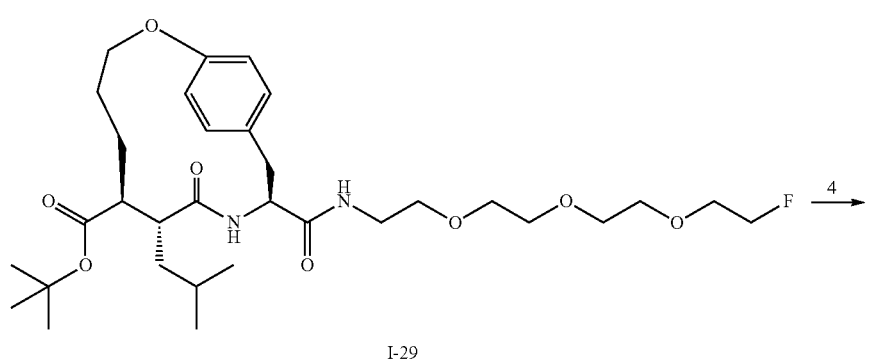
I-29
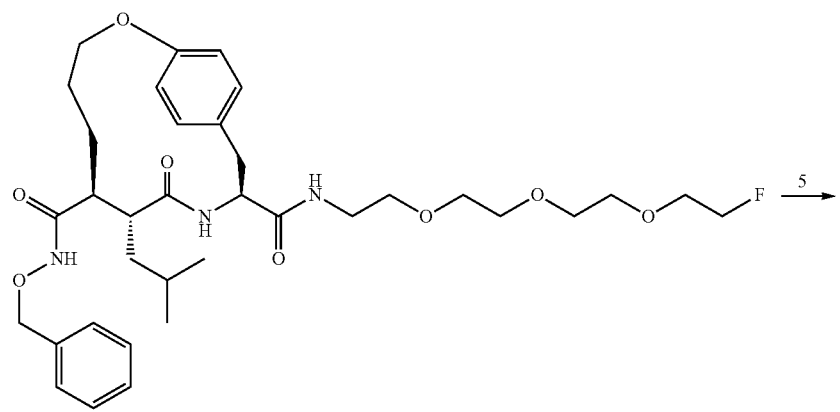
I-30

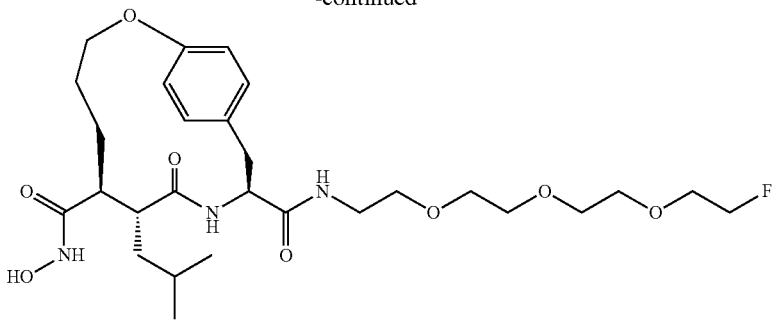

17

Reagents & conditions:
1. tetraethylene glycol monoamine, HATU, DIEA, DMF;
2. Ts—Cl, DMAP, Py, DCM;
3. TBAF, THF;
4. i) TFA/DCM,
  ii) O-benzylhydroxylamine hydrochloride, HBTU, NMM, DMF;
5. Pd/C, H$_2$, MeOH Intermediate 27 (I-27)

To a solution of I-7 and HATU (147 mg) in DMF (1 mL) was added dropwise DIEA (135 µL) and tetraethylene glycol monoamine (45 µL). After stirring at room temperature for 5 h, the reaction was quenched by 10% aqueous citric acid, and the reaction mixture was extracted with EtOAc. The organic phase was washed with 1N HCl, brine, and saturated NaHCO$_3$. After drying over MgSO$_4$ and filtration, solvent was removed with a rotary evaporator, and the mixture was purified by silica gel chromatography (DCM:MeOH=30:1) to afford I-27 in 70% yield. Q-TOF LC/MS m/z 609.3797 [M+H]+ (calcd. 608.37 for C$_{32}$H$_{52}$N$_2$O$_9$ [M]+); $^1$H NMR (400 MHz, CDCl$_3$) δ-0.45 (1H, m), 0.685 (1H, m), 0.825 (6H, m), 1.13 (9H, s), 1.27-1.64 (6H, m), 1.94 (1H, m), 2.05 (1H, m), 2.64 (2H, m), 3.38-3.91 (16H, m), 4.07 (1H, t, J=8 and 12 Hz), 4.25 (1H, m), 4.99 (1H, m), 6.35-7.06 (4H, aromatic H); $^{13}$C NMR (100 MHz, CDCl$_3$) δ 21.45, 24.12, 25.92, 28.20, 30.00, 31.10, 38.40, 39.51, 40.65, 49.28, 50.18, 52.77, 61.65, 69.98, 70.22, 70.60, 70.90, 72.60, 73.92, 80.30, 120.40, 123.35, 129.95, 132.23, 132.46, 159.12, 171.62, 173.23, 174.34.

Intermediate 28 (I-28)

To the solution of alcohol (I-27, 250 mg), DMAP (catalytic amount) and TsCl (86.2 mg) in DCM (4.1 mL) was added pyridine (83.1 µL). The reaction mixture was stirred at room temperature overnight. The mixture was washed with 1N HCl, water, sat. NaHCO$_3$, and organic phase was collected. After drying (MgSO$_4$) and concentration, the residue was purified by silica gel column chromatography (DCM:MeOH=30:1) to afford 43% product. Q-TOF LC/MS m/z 763.3845 [M+H]+ (calcd. 762.38 for C$_{39}$H$_{58}$N$_2$O$_{11}$S [M]+); $^1$H NMR (400 MHz, CDCl$_3$) δ-0.46 (1H, m), 0.64 (1H, m), 0.79 (6H, m), 0.86 (2H, m), 1.40 (9H, s), 1.23-1.58 (6H, m), 1.88-2.05 (2H, m), 2.45 (3H, s), 2.66 (1H, m), 3.38-3.74 (16H, m), 4.0/5 (1H, m), 4.19 (2H, m), 4.90 (1H, m), 6.94-7.83 (8H, aromatic m); $^{13}$C NMR (100 MHz, CDCl$_3$) δ 21.46, 21.80, 24.07, 26.00, 28.21, 29.90, 31.18, 37.62, 39.56, 40.53, 49.36, 50.08, 53.13, 68.84, 69.49, 69.76, 70.46, 70.56, 70.74, 70.97, 73.94, 77.36, 80.79, 120.63, 123.41, 128.13, 129.74, 130.03, 132.14, 132.25, 145.06, 159.16, 171.41, 173.44, 173.99.

Intermediate 29 (I-29)

To the solution of I-27 (60 mg) in THF (0.5 mL) was added TBAF (1.0 M in THF, 200 µL), and the reaction mixture was stirred at 50° C. for 3 h. After removal of solvent, the crude mixture was dissolved in DCM and washed with water and brine. After drying (MgSO$_4$) and concentration, the mixture was purified by silica gel column chromatography (DCM:MeOH=30:1) to afford 58% product. LC/MS m/z 611.3 [M+H]+ (calcd. 610.36 for C$_{32}$H$_{51}$FN$_2$O$_8$ [M]+).

Intermediate 30 (I-30)

The tert-butyl ester (I-29, 28 mg) was dissolved in DCM (0.7 mL) followed by addition of TFA (0.7 mL). The reaction mixture was stirred at room temperature for 1 h. The solvent was removed and dried under vacuum. The resulting acid, O-benzylhydroxyl amine hydrochloride (29.4 mg), and HBTU (38.5 mg) were dissolved in DMF (0.6 mL) followed by addition of DIEA (32 µL). The reaction was stirred at room temperature overnight and quenched with 10% citric acid. Organic phase was washed with 1 N HCl, water, saturated NaHCO$_3$, and brine. After drying (MgSO$_4$) and concentration, I-30 was purified by silica gel column chromatography (DCM:MeOH=20:1) to afford 63% product. LC/MS m/z 660.3 [M+H]+ (calcd. 659.36 for C$_{35}$H$_{50}$FN$_3$O$_8$ [M]+); $^1$H NMR (400 MHz, CDCl$_3$) δ-0.53 (1H, m), 0.74 (6H, d, J=8 and 16 Hz), 0.90 (1H, m), 0.97 (1H, m), 1.19-1.43 (2H, m), 1.74 (1H, m), 2.13 (1H, m), 2.69 (1H, m), 3.37-3.81 (16H, m), 4.12 (2H, m), 4.53 (1H, m), 4.63 (1H, m), 4.86-4.90 (3H, m), 6.86-7.42 (9H, aromatic H); $^{13}$C NMR (100 MHz, CDCl$_3$) δ 21.43, 23.97, 25.98, 29.58, 29.82, 30.38, 39.62, 37.68, 40.01, 46.89, 48.42, 53.53, 69.63, 70.42, 70.58, 70.62, 70.66, 70.88, 73.61, 84.14, 120.67, 123.13, 128.66, 129.21, 129.74, 132.06, 132.37, 135.43, 150.23, 159.11, 160.69, 171.4, 174.3.

17 [(6S,7R,10S)—N10-(2-(2-(2-(2-fluoroethoxy) ethoxy)ethoxy)ethyl)-N$^6$-hydroxy-7-isobutyl-8-oxo-2-oxa-9-aza-1(1,4)-benzenacycloundecaphane-6,10-dicarboxamide]

The benzylhydroxamate (I-30, 19 mg) was dissolved in MeOH (0.5 mL), and 10% Pd/C (~10 mg) was added. The reaction was stirred under H$_2$ (balloon) for 3 h. The Pd/C was removed by passing through celite pad, and solvent was removed by a rotary evaporator. 17 was further purified by a reverse phased semi-preparative C-18 HPLC (solvent A: water, 25 mM NH$_4$OAc; solvent B; acetonitrile; 20% to 90% of B for 17 min; flow rate=5 mL/min). LC/MS m/z 570.2 [M+H]+ (calcd. 569.31 for C$_{28}$H$_{44}$FN$_3$O$_8$ [M]+); $^1$H NMR

71
(400 MHz, CD$_3$OD) δ-0.53 (1H, m), 0.82 (6H, m), 0.90 (1H, m), 1.24-1.39 (4H, m), 1.68 (1H, m), 2.15 (1H, m), 2.67 (1H, m), 3.30-3.78 (16H, m), 4.08-4.19 (2H, m), 4.46 (1H, m), 4.58 (1H, m), 6.87-7.25 (4H, aromatic H); $^{13}$C NMR (100 MHz, CD$_3$OD) δ 21.62, 24.49, 26.92, 30.98, 31.32, 38.30, 40.49, 41.49, 54.74, 70.48, 71.34, 71.50, 71.59, 71.63, 71.68, 74.53, 83.26, 84.93, 121.51, 123.81, 130.34, 133.76, 133.82, 160.037, 172.79, 173.61, 175.90.
Scheme 8. Synthesis of 18.
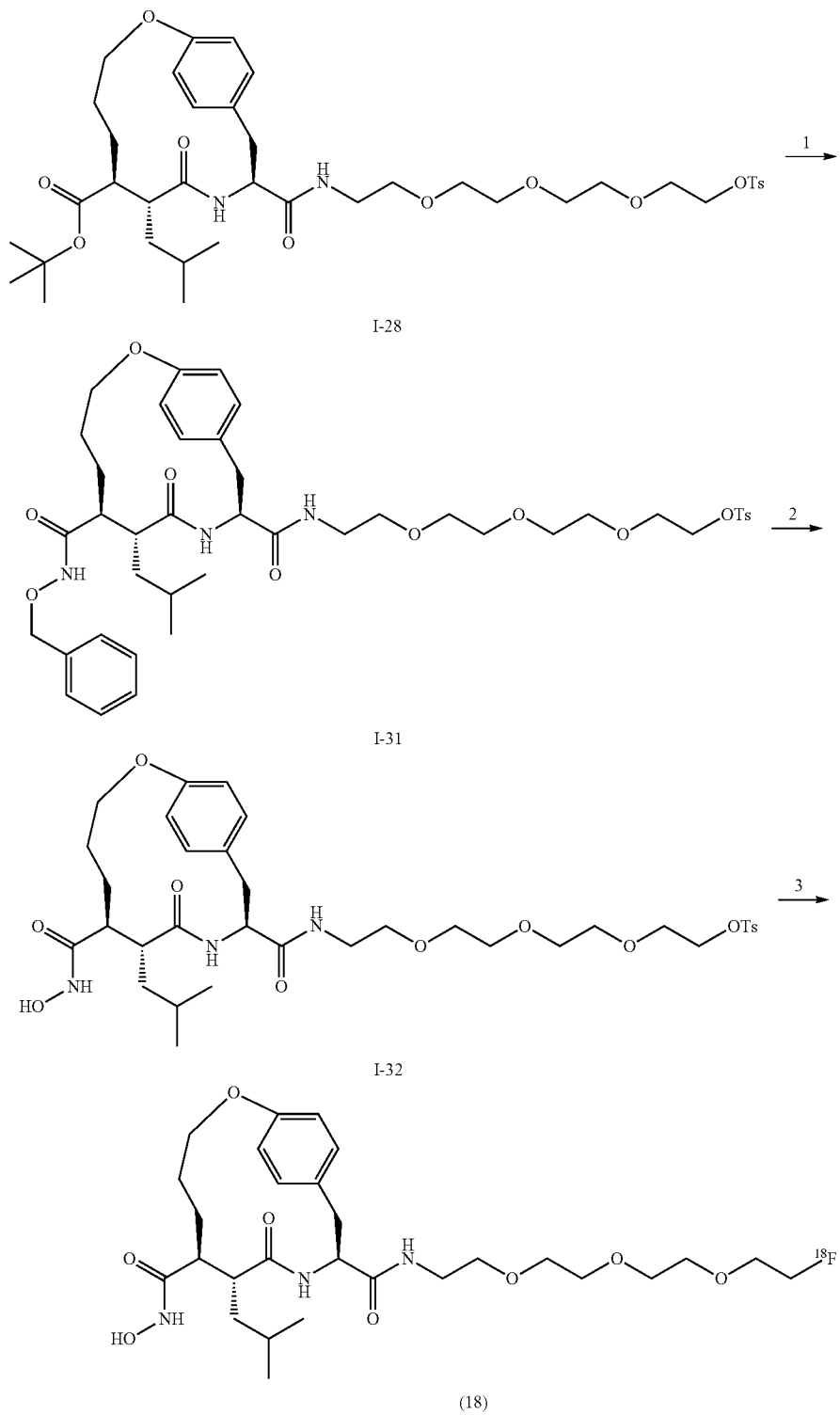
Reagents & conditions: 1. i) TFA/DCM, ii) O-benzylhydroxyl amine hydrochloride, HBTU, NMM, DMF; 2. Pd/C, H$_2$, MeOH; 3. K$^{18}$F/Kryptofix or Me$_4$N$^{18}$F.

Intermediate 31 (I-31)

The tert-butyl ester (I-28, 112.4 mg) was dissolved in DCM (1 mL) followed by addition of TFA (1 mL). The reaction mixture was stirred at room temperature for 1 h. The solvent was removed and dried under vacuum. The resulting acid, O-benzylhydroxylamine hydrochloride (28.1 mg), and HBTU (67 mg) were dissolved in DMF (1 mL) followed by addition of NMM (26 µL). The reaction was stirred at room temperature overnight and quenched with 10% citric acid at 0° C. Organic phase was washed with 1 N HCl, water, saturated NaHCO$_3$, and brine. After drying (MgSO$_4$) and concentration, I-31 was purified by silica gel column chromatography (DCM:MeOH=20:1) to afford 61% product. Q-TOF LC/MS m/z 812.3740 [M+H]+ (calcd. 811.37 for C$_{42}$H$_{57}$N$_3$O$_{11}$S [M]+); $^1$H NMR (400 MHz, CDCl$_3$) δ-0.17 (1H, m), 0.841 (1H, m), 0.89 (7H, m), 0.96 (1H, m), 1.19 (1H, m), 1.45 (1H, m), 1.65 (1H, m), 1.82 (1H, m), 2.27 (1H, m), 2.45 (3H, s), 2.65 (2H, m), 3.43-3.73 (17H, m), 4.13 (2H, m), 4.17 (1H, m), 4.30 (1H, m), 5.00 (1H, m), 7.26-7.82 (13H, aromatic H); $^{13}$C NMR (100 MHz, CDCl$_3$) δ 21.29, 21.84, 24.13, 26.02, 30.00, 31.28, 37.98, 39.62, 41.03, 47.34, 48.76, 53.34, 68.78, 69.54, 69.79, 70.46, 70.52, 70.77, 70.96, 73.35, 108.01, 120.48, 120.77, 123.42, 125.02, 128.11, 129.01, 129.91, 130.09, 132.41, 132.73, 143.51, 145.26, 158.99, 171.20, 171.57, 171.80.

Intermediate 32 (I-32)

The benzylhydroxamate (I-31, 67 mg) was dissolved in MeOH (2 mL), and 10% Pd/C (20 mg) was added. The reaction was stirred under H$_2$ (balloon) for 3 h. The Pd/C was removed by passing through a celite pad, and the solvent was removed by a rotary evaporator. I-32 was obtained with 87% yield after HPLC purification and lyophilization (a reverse phased semi-preparative C-18 HPLC; solvent A: water with 25 mM NH$_4$OAc; solvent B; acetonitrile; 45% to 90% of B for 20 min; flow rate=5 mL/min). Q-TOF LC/MS m/z 721.3353 [M]+ (calcd. 721.32 for C$_{35}$H$_{51}$N$_3$O$_{11}$S [M]+); $^1$H NMR (400 MHz, CD$_3$OD) δ-0.23 (1H, m), 0.74 (3H, m), 0.78 (1H, m), 0.84 (3H, m), 0.97 (1H, m), 1.33 (1H, m), 1.49 (1H, m), 1.53 (1H, m), 1.69 (1H, m), 1.89 (1H, m), 2.26 (1H, m), 2.45 (3H, s), 2.78 (1H, m), 3.56-3.66 (16H, M), 3.81 (1H, m), 4.14 (2H, m), 4.73 (1H, m), 6.95-7.80 (8H, aromatic H); $^{13}$C NMR (100 MHz, CD$_3$OD) δ 21.44, 21.61, 24.16, 26.94, 29.02, 29.98, 37.96, 40.35, 40.50, 49.57, 50.70, 51.3, 52.05, 69.77, 70.43, 70.93, 71.33, 71.52, 71.57, 71.65, 73.89, 123.65, 123.81, 129.10, 130.93, 131.08, 133.15, 134.98, 146.48, 159.0, 173.63, 176.01

Example 6: Preparation of $^{99m}$Tc-2

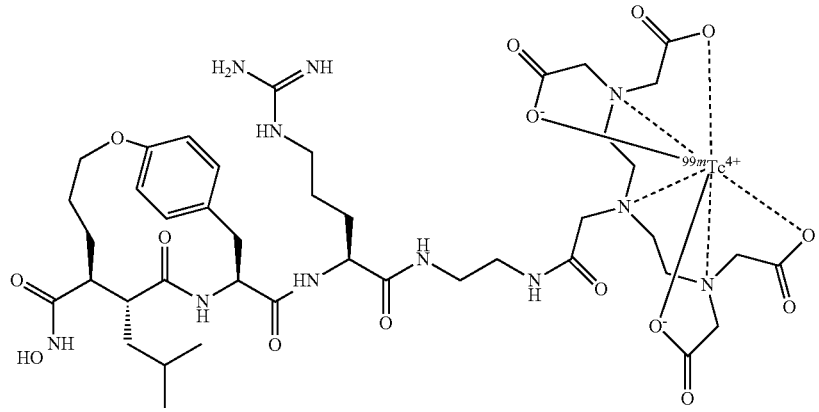

10 µl (30 µg) the DTPA conjugate 2, and 50 µL (6.6mCi) $^{99m}$Tc pertechnetate solution were mixed in a vial, followed by adding 4 µL (300 µg) freshly prepared SnCl$_2$ solution and 500 µl succinic acid buffer. The mixture was incubated at room temperature for 20 min. Radio-HPLC analysis showed the desired labeling product with 99% yield and specific activity of 0.22 mCi/m. The product is reformulated with saline for in vitro and in vivo studies (FIG. 1).

Example 7: Preparation of $^{67}$Ga-3

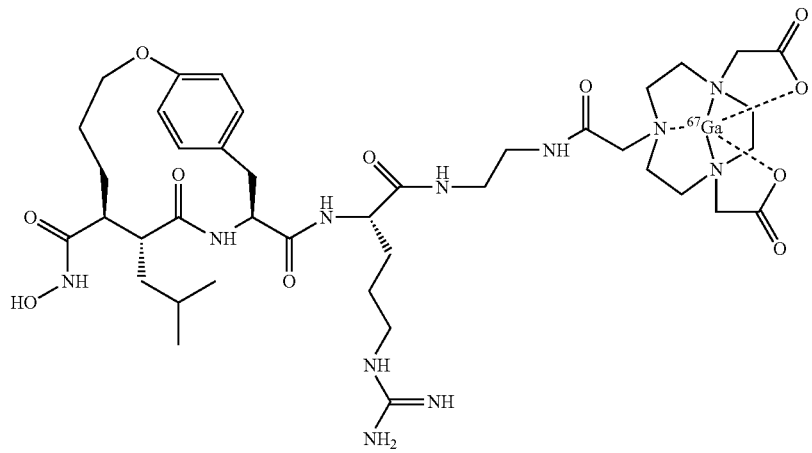

NOTA conjugate 3 is radiolabeled with $^{67}$Ga in a 0.5 M NH$_4$OAc-buffered solution (pH 3.5) at 40° C. for 30 min. Briefly, 10 μL of $^{67}$GaCl$_3$ (1mCi in 0.05 M HCl), 104 (10 μg) the NOTA conjugate 3 in water, and 100 μL of 0.5 M NH$_4$OAc (pH 3.5) are mixed in a reaction vial and incubated at room temperature for 30 min. The labeling is analyzed by both radio-HPLC and radio-TLC to demonstrate its radiochemical identity, retention time, radiochemical purity, radiochemical specificity, and radiochemical yield. It is further purified by radio-HPLC and C$_{18}$ Sep-Pak cartridge. The labeled product is reformulated with saline for in vitro and in vivo studies.

Figure 7A:
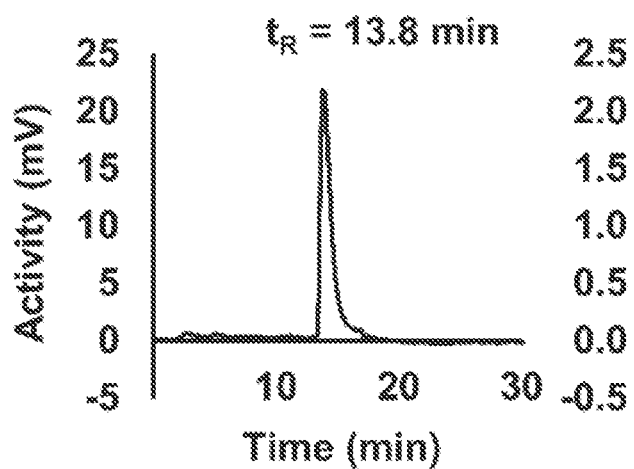
FIGS. 7A-7B illustrate $^{99m}$Tc-1 stability. Representative radiochromatograms of $^{99m}$Tc-1 after radiolabeling (FIG. 7A) and in urine collected from a C57BL/6J mouse at 2 hours post-injection (FIG. 7B). t$_R$: retention time.
Figure 7B:
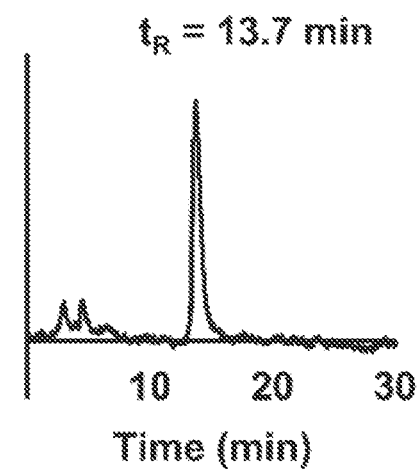

Example 8: Preparation of $^{64}$Cu-3 from mice 2 hours after intravenous injection of the tracer showed similar radio-HPLC profiles with a single major peak at a similar retention time without significant degradation (FIGS. 7A-7B).

Based on log P values and HPLC retention time, $^{99m}$Tc-1 showed higher hydrophilicity than $^{99m}$Tc-RP805. $^{99m}$Tc-1 showed high water solubility (Log P$_{n\text{-}octanol/water}$=−4.0±0.1), with high radiochemical stability and favorable properties for cardiovascular imaging.

Example 10: Biodistribution

Biodistribution at 2 h post-injection (p.i.) and blood clearance were evaluated in C57Bl/6J mice injected with 16±5 MBq of $^{99m}$Tc-1 (n=6) or $^{99m}$Tc-RP805 (n=6). In vivo

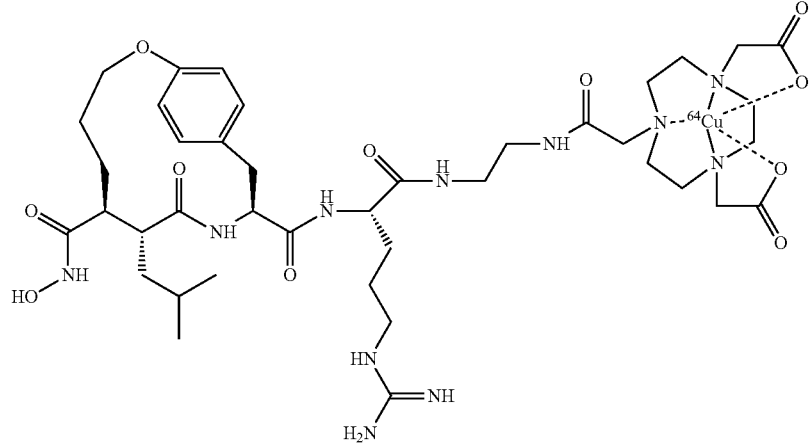

$^{64}$CuCl$_2$ is converted to $^{64}$Cu(OAc)$_2$ by adding 0.5 mL of 0.4 M ammonium acetate (NH$_4$OAc) solution (pH=5.5) to 20 μL $^{64}$CuCl$_2$. $^{64}$Cu(OAc)$_2$ solution (1.0 mCi) is added into a solution of the NOTA conjugate (4.0 μg) in 0.4 M NH$_4$OAc (pH=5.5). The solution is stirred for 20 min at 40° C. The $^{64}$Cu-labeled product is monitored by both radio-HPLC and radio-TLC. It is further purified by radio-HPLC and C$_{18}$ Sep-Pak cartridge. Quality control is performed by analytical HPLC to identify retention time, radiochemical yield, radiochemical purity, radiochemical specificity, and radiochemical stability. The labeled product is reformulated with saline for in vitro and in vivo studies.

Example 9: Synthesis, Stability and Solubility

Arginine-containing macrocyclic hydroxamate 19 and its HYNIC-conjugated analog (1, or RYM1) for Tc-99m labeling were prepared. Without wishing to be limited by any theory, incorporation of Arg increased hydrophilicity, and improved pharmacokinetics and MMP targeting.

All compounds were synthesized in multiple steps starting from an anti-succinic acid analog, (2R,3S)-3-(tert-butoxycarbonyl)-2-iso-butylhex-5-enoic acid. Both 19 and 1 had MMP binding profiles similar to the RP805 precursor. 1 showed a high affinity for recombinant human rhMMP-2, rhMMP-9 and rhMMP-12. $^{99m}$Tc-1 was obtained with a high radiochemical yield and purity (>98%).

Figure 8A:
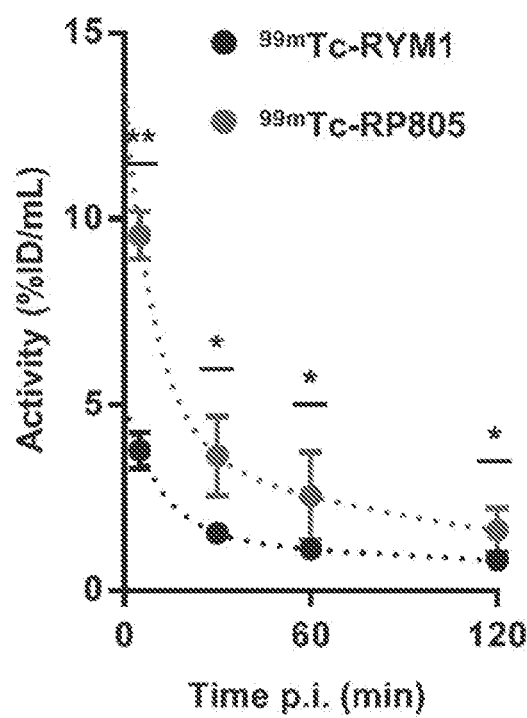
FIGS. 8A-8B illustrate tracer biodistribution and clearance. Blood kinetics (FIG. 8A) and biodistribution at 2 hours (FIG. 8B) of $^{99m}$Tc-1 (●) and $^{99m}$Tc-RP805 (✳) in C57BL/6J mice. SG: Salivary Glands, WAT: White Adipose Tissue; pAT: Periaortic Adipose Tissue; ID: injected dose. n=5 in each group. *P<0.05, **P<0.01.
Figure 8B:
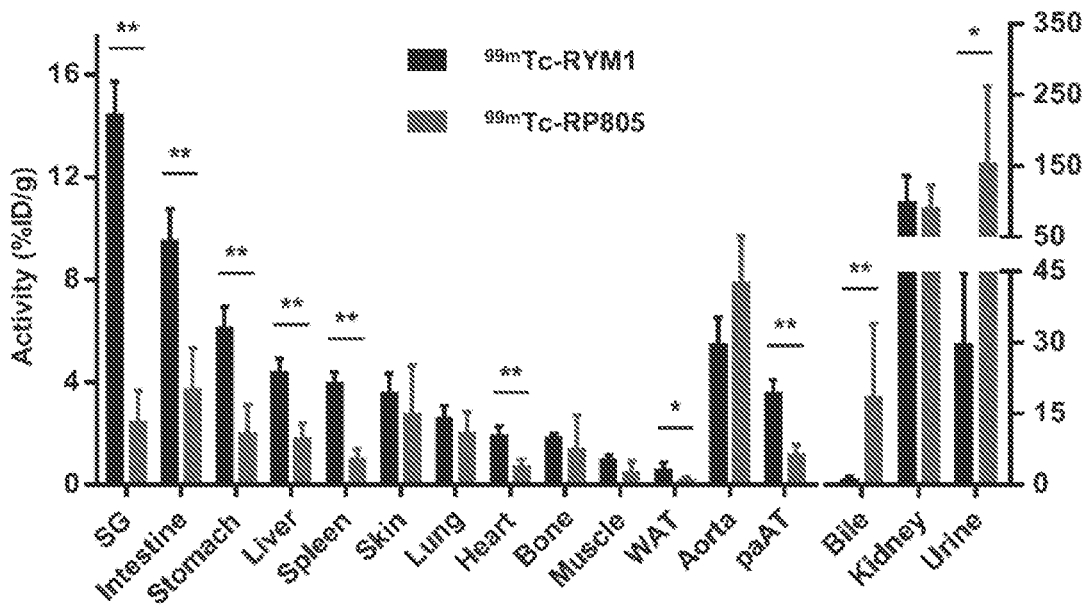
Figure 9A:
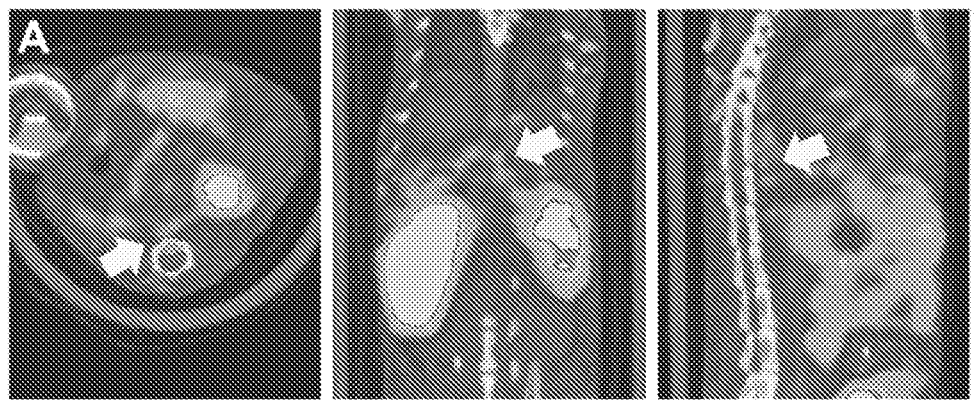
FIGS. 9A-9D illustrate $^{99m}$Tc-1 imaging of AAA.
Figure 9B:
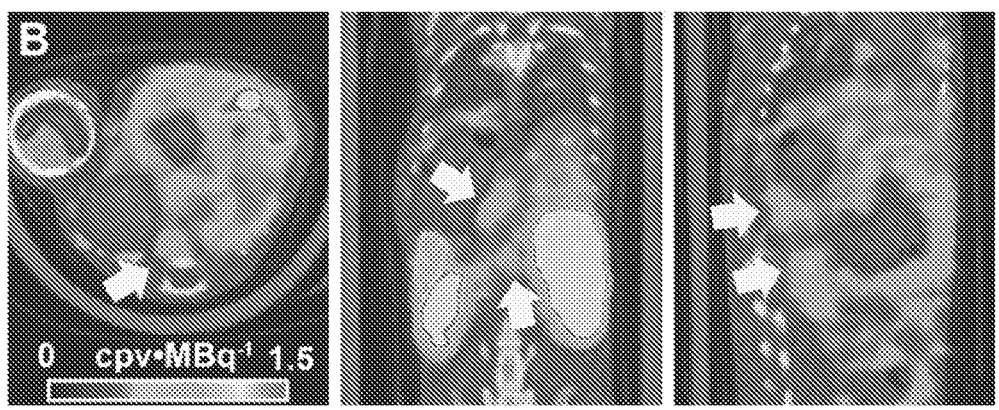
Figure 9C:
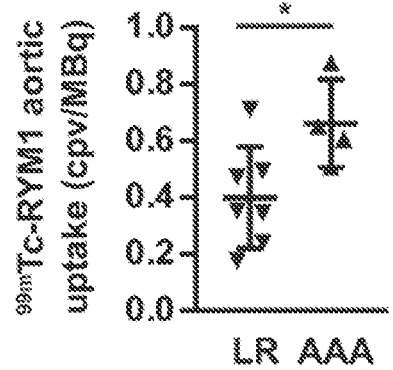
Figure 9D:
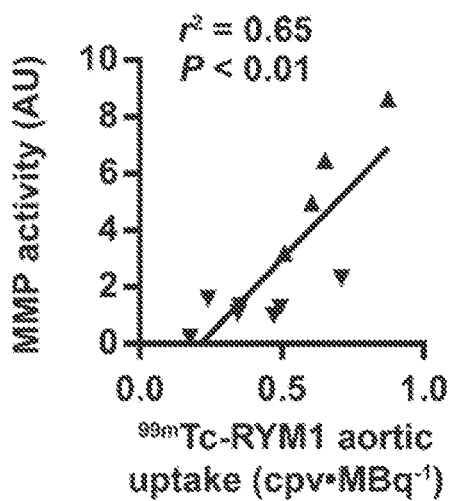
Figure 13:
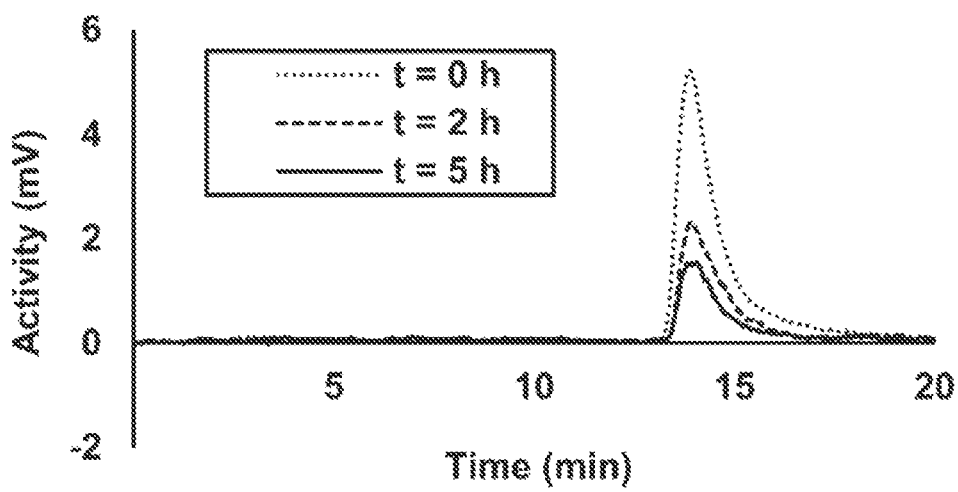
FIG. 13 illustrates $^{99m}$Tc-1 stability in blood. Radiochromatograms of $^{99m}$Tc-1 obtained after incubation in mouse blood at 37° C. for 0, 2 and 5 hours (h) demonstrate a single peak.

$^{99m}$Tc-1 showed a high radiochemical stability in the radiolabeling media, and in urine and blood. The radioactive material extracted after in vitro incubation of $^{99m}$Tc-1 in mouse blood for up to 5 hours (FIG. 13) or urine collected targeting to aneurysm and specificity of $^{99m}$Tc-1 was evaluated in high-fat fed apolipoprotein E-deficient mice, 4 weeks after carotid aneurysm induction through peri-adventitial application of CaCl$_2$. The animals were injected with 31±14 MBq of $^{99m}$Tc-1 with (n=3) or without (n=4) pre-injection of non-labeled 1. This was followed by quantitative autoradiography of arterial tracer uptake at 2 h p.i. $^{99m}$Tc-1 showed a lower blood pool activity compared to $^{99m}$Tc-RP805 at 1 and 2 h p.i. [1.3±0.4 vs 2.8±1.2% injected dose (ID)/mL and 1.0±0.4 vs 1.8±0.7% ID/mL, respectively, P<0.05 for both] and lower hepatobiliary excretion (bile: 1.5±0.3 vs 17.8±13.3% ID/g, P<0.05) (FIG. 8B).

Tissue uptake was higher in several collected tissues, but not in control aorta (6.0±1.4 vs 8.4±1.9% ID/g, P<0.05). This difference was primarily reflected in the initial activity values, suggesting a difference in first-pass clearance of the tracer from blood. Despite a lower blood level, $^{99m}$Tc-1 tissue uptake at 2 hours post-injection was significantly higher than $^{99m}$Tc-RP805 in several organs, but not in the normal aorta. Both tracers displayed a high activity in the kidneys and urine, indicative of renal clearance. However, contrary to the animals injected with $^{99m}$Tc-1 who had limited bile activity, animals injected with $^{99m}$Tc-RP805 showed elevated activity in the bile (FIG. 8B).

Figure 14A:
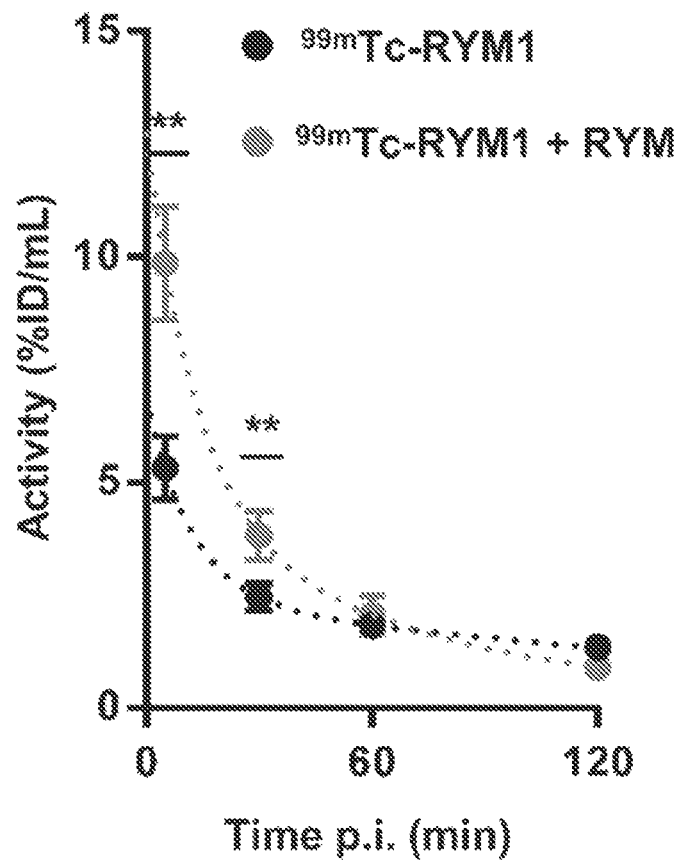
FIGS. 14A-14B illustrate $^{99m}$Tc-1 biodistribution and clearance. Blood kinetics (FIG. 14A) and biodistribution at two hours (FIG. 14B) of $^{99m}$Tc-1 in apoE$^{-/-}$ with CaCl$_2$-induced carotid aneurysm without (●) and with the pre-injection of an excess of 19 (✳). SG: Salivary Glands, WAT: White Adipose Tissue. n=6 and 5, respectively for $^{99m}$Tc-1 and $^{99m}$Tc-1+19 (RYM). **P<0.01
Figure 14B:
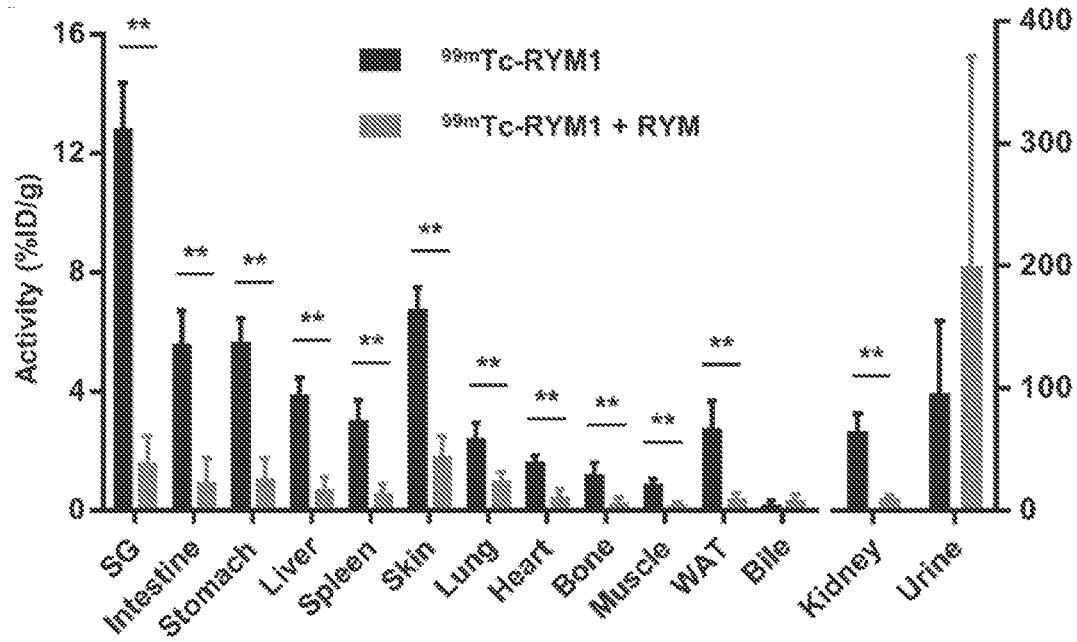

$^{99m}$Tc-1 binding to carotid aneurysm and specificity in vivo were evaluated in apoE$^{−/−}$ mice at seven weeks after peri-adventitial application of CaCl$_2$ to left carotid arteries. Similar to C57BL/6J mice. $^{99m}$Tc-1 (31±14 MBq, i.v.) displayed a fast blood clearance, resulting in a residual blood pool activity at 1 and 2 hours post-injection of 1.8±0.2 and 1.3±0.1% ID/mL, respectively. Autoradiographic evaluation of the carotids and aorta harvested at 2 h showed high uptake of the tracer in the left carotid artery aneurysm (n=6, FIGS. 4A-4F). Pre-injection of an excess of the parent pan-MMP-inhibitor 1 led to a 4.6-fold decrease in carotid aneurysm tracer uptake (n=5, P<0.01). Albeit to a smaller degree, tracer uptake was also reduced in the aorta, resulting in a significant 1.8-fold decrease in the aneurysm-to-aorta uptake ratio by autoradiography under blocking conditions (P<0.05, FIGS. 4A-4F). Pre-injection of the parent pan-MMP-inhibitor 1 significantly reduced $^{99m}$Tc-1 uptake, as assessed by gamma well counting in all tissues evaluated, but not in the bile (FIGS. 14A-14B), indicating a certain degree of systemic MMP activation in these mice. As such, the novel hydroxamate-based panMMP inhibitor-derived tracer $^{99m}$Tc-1 demonstrated improved pharmacokinetics for cardiovascular imaging and specific in vivo binding to aneurysm.

Figure 5:
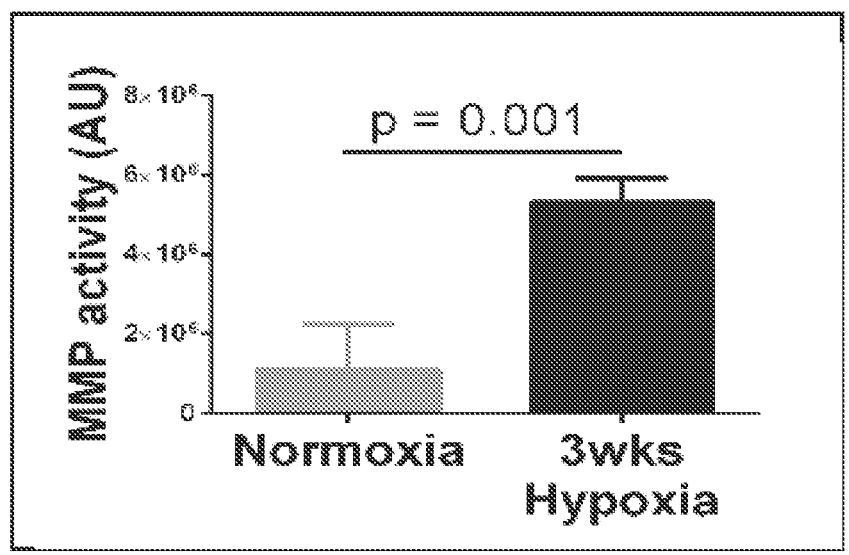
FIG. 5 illustrates non-limiting MMP activity of the lung tissue of hypoxia-exposed mice with pulmonary arterial hypertension (PAH) and control, normoxia mice, quantified using a panMMP substrate (AU: arbitrary units).
Figure 6:
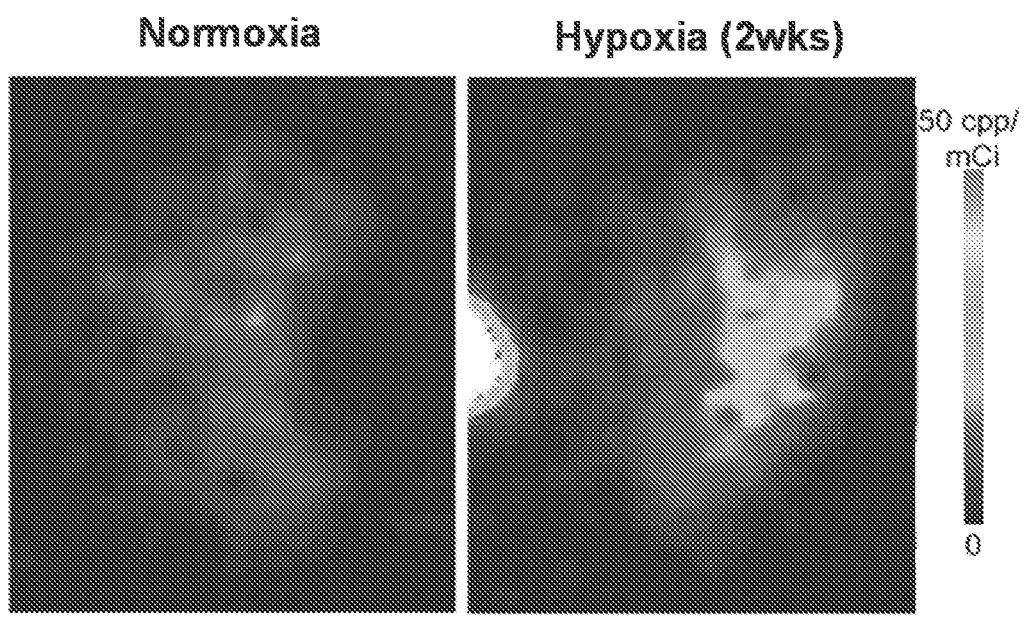
FIG. 6 illustrates ex vivo planar images of the lungs harvested about 60 minutes after intravenous administration of $^{99m}$Tc-1, demonstrating considerably higher signal in the lung of hypoxia-exposed mouse with pulmonary arterial hypertension (PAH).

The performance of the tracers was also evaluated in a mouse model of pulmonary arterial hypertension (PAH) following exposure to hypoxia (10%) for 2-3 weeks. This led to significant upregulation of MMP activity (FIG. 5). In vivo microSPECT-CT imaging of a mouse exposed to 10% hypoxia for 2 weeks was performed 30 minutes following intravenous injection of $^{99m}$Tc-1 (1mCi) and showed considerably higher $^{99m}$Tc-1 signal in the lungs of this mouse compared to a control, normoxic animal. In certain embodiments, the background indicated a more delayed imaging, possibly at 1 hour, could be implemented. On ex vivo planar images acquired at 1 hour, the lung signal was considerably higher (>2-fold) in hypoxia-exposed lungs than normoxic controls (FIG. 6).

Example 11: $^{99m}$Tc-1 Imaging in AAA

Ang II infusion resulted in the death of 31% (5/16) of apoE$^{-/-}$ mice within 4 weeks. The surviving animals underwent $^{99m}$Tc-1 microSPECT/CT imaging at 1 h post-tracer injection. On visual and quantitative analysis of the images, a range of tracer uptake was detectable in suprarenal abdominal aortae of the animals. While in a subset of animals, the aortic $^{99m}$Tc-1 signal was readily detectable on in vivo SPECT/CT images, other animals displayed only modest uptake of the tracer in their suprarenal abdominal aortae (FIGS. 9A-9D and 15).

Visual examination of the aorta at the time of tissue harvesting immediately after microSPECT/CT image acquisition detected varying degrees of aortic remodeling. Based on this visual analysis, 25% of animals (4/11) showed major focal dilation, and were classified as those with suprarenal AAA. Conversely, 44% of animals (7/11) showed no or only modest remodeling, and were categorized as the low remodeling group. This visual categorization was confirmed on morphometric analysis of tissue sections, which showed a significantly higher maximal external aortic diameter in the AAA, compared to the low remodeling group (1.74±0.35 vs 0.99±0.08 mm, P<0.01, FIGS. 10A-10B and 16A-16B).

Figure 10A:
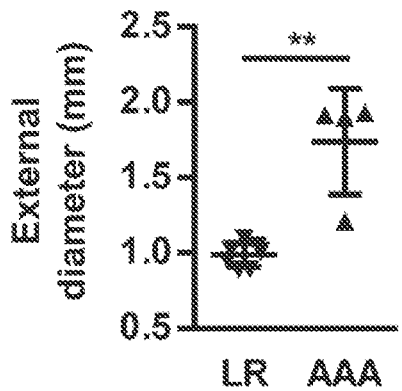
FIGS. 10A-10B illustrate ex vivo characterization of suprarenal abdominal aorta.
Figure 10B:
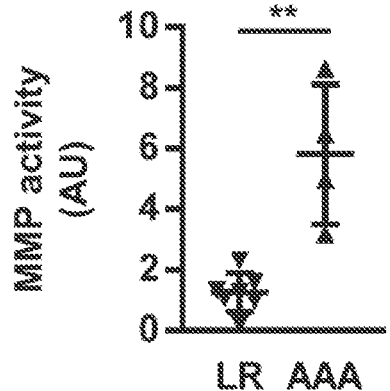

When categorized based on aortic size, there was a significant difference in suprarenal aortic $^{99m}$Tc-1 signal between the AAA and low remodeling groups (0.66±0.16 vs 0.40±0.18 counts per voxel (cpv)/MBq, P<0.05). Similarly, fluorometric assessment of MMP activity showed significantly higher MMP activity in the AAA group compared to the low remodeling group (FIGS. 10A-10B). Consistent with the MMP-specificity of the tracer, a significant correlation existed between the aortic $^{99m}$Tc-1 signal in vivo and MMP activity detected by zymography ex vivo (r$^2$=0.65, P<0.01, FIGS. 9A-9D). There was no difference in the left ventricle blood pool activity between the two groups of animals (0.14±0.10 vs 0.12±0.08 cpv/MBq, for AAA and low remodeling groups, respectively, P=NS).

Example 12: Gene Expression Analysis

Figure 11A:
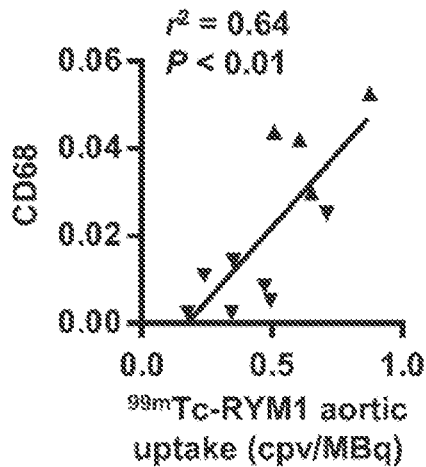
FIGS. 11A-11B illustrate correlates of aortic $^{99m}$Tc-1 signal on in vivo microSPECT/CT images. Correlation between suprarenal abdominal aorta$^{99m}$Tc-1 uptake and β-actin-normalized CD68 (FIG. 11A) and MMP-12 (FIG. 11B) gene expression. cpv: counts per voxel.
Figure 11B:
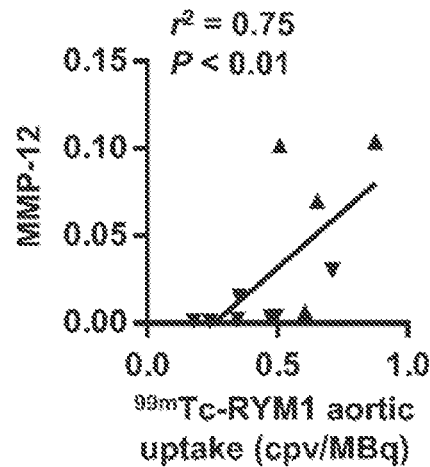
Figure 17A:
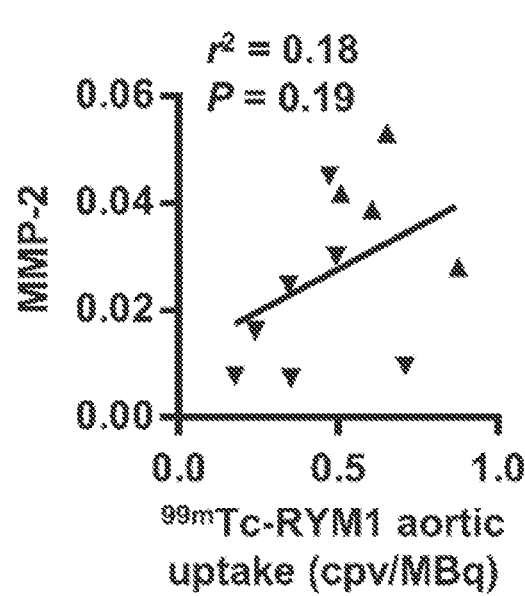
FIGS. 17A-17B illustrate correlations between suprarenal abdominal aorta$^{99m}$Tc-1 signal on in vivo microSPECT/CT images and β-actin-normalized MMP-2 (FIG. 17A) and MMP-9 (FIG. 17B) gene expression. cpv: counts per voxel.
Figure 17B:
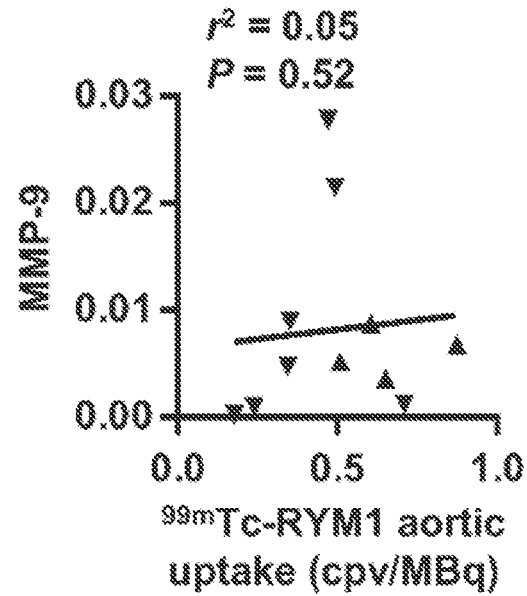
Figure 18A:
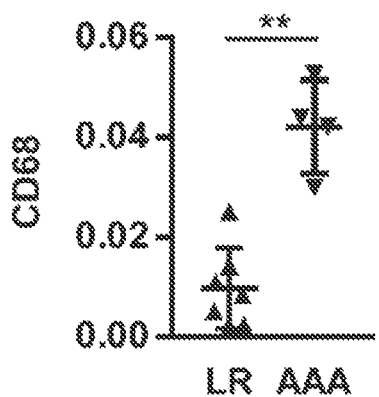
FIGS. 18A-18D illustrate gene expression in suprarenal abdominal aorta. Aortic β-actin-normalized CD68 (FIG. 18A), MMP-2 (FIG. 18B), MMP-9 (FIG. 18C) and MMP-12 (FIG. 18D) mRNA expression in angiotensin II-infused apoE$^{-/-}$ mice with low aortic remodeling (LR) or aneurysm (AAA). *P<0.05, **P<0.01.
Figure 18B:
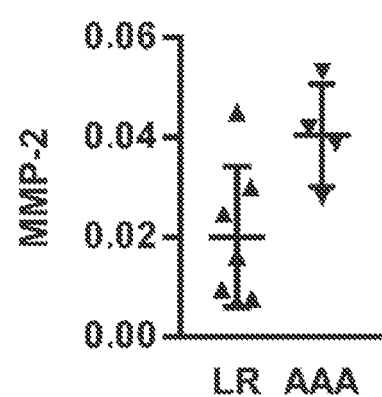
Figure 18C:
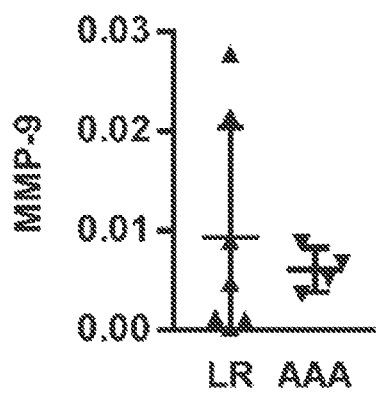
Figure 18D:
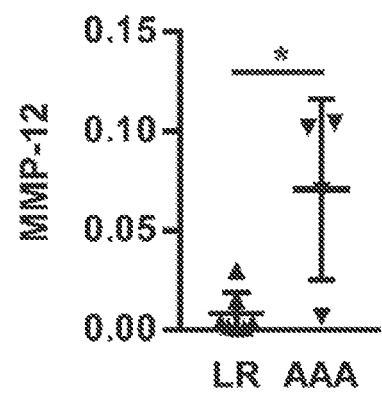

There was no significant difference in MMP-2 and MMP-9 gene expression between AAA and low remodeling groups, whereas macrophage marker, CD68 and MMP-12 expression were significantly higher in the AAA, compared to the low remodeling group (FIGS. 17A-17B). Moreover, aortic $^{99m}$Tc-1 signal in vivo correlated with CD68 and MMP-12 (FIGS. 11A-11B), but not MMP-2 and MMP-9 gene expression (FIGS. 18A-18D). Similarly, CD68 and MMP-12, but not MMP-2 and MMP-9, expression correlated with tissue MMP activity (Table 1).

TABLE 1

Spearman's rank correlation coefficient (p-value) between $^{99m}$Tc-1 uptake (counts per voxel/MBq), external diameter (mm), MMP activity (arbitrary units) and β-actin-normalized expression of CD68, MMP-2, MMP-9 and MMP-12 in the abdominal aorta of angiotensin II-infused apoE$^{-/-}$ mice.

|  | $^{99m}$Tc-1 uptake | External diameter | MMP activity | CD68 | MMP-2 | MMP-9 |
|---|---|---|---|---|---|---|
| MMP-12 | 0.86 (0.001) | 0.38 (0.25) | 0.77 (0.007) | 0.85 (0.002) | 0.33 (0.33) | 0.23 (0.50) |
| MMP-9 | 0.22 (0.52) | −0.13 (0.71) | −0.03 (0.95) | 0.14 (0.69) | 0.37 (0.26) |  |
| MMP-2 | 0.43 (0.19) | 0.59 (0.06) | 0.35 (0.29) | 0.36 (0.27) |  |  |
| CD68 | 0.80 (0.005) | 0.63 (0.04) | 0.93 (0.000) |  |  |  |
| MMP activity | 0.81 (0.004) | 0.68 (0.03) |  |  |  |  |
| External diameter | 0.44 (0.18) |  |  |  |  |  |

Example 13: MMP Binding Screens

MMPs inhibition assays were all carried out based on the effects of an inhibitor on MMP-mediated catalytic cleavage of a fluorogenic substrate i.e. Mca-Pro-Leu-Gly-Leu-Dpa-Ala-Arg-NH$_2$. The recombinant human MMPs including rhMMP-2, rhMMP-9, and rhMMP-12 obtained from R&D Systems (Minneapolis, Minn., USA) were activated by 1 mM p-aminophenylmercuric acetate (APMA, Sigma) at 37° C. for certain hours according to the manufacturer's instructions. The activated MMPs were diluted in the assay buffer consisting of 50 mM Tris, 10 mM CaCl$_2$, 150 mM NaCl, 0.05% Brij-35 (w/v), pH 7.5 (TCNB). The assays were carried out in 96-well non-binding surface black microplates (Fisher Scientific).

Typically, 10 μL of an inhibitor solution at several different concentrations such as 250 nM, 125 nM, 62.5 nM, 31.25 nM, and 15.6 nM were added into 70 μL assay buffer in each well, followed by adding 10 μL (10 ng) of the activated MMP solutions into each well. The solutions were incubated at room temperature for 20 min. 10 μL of the fluorogenic MMP substrate i.e. Mca-KPLGL-Dpa-AR-NH$_2$ (R&D Systems) at 4 different concentrations (such as 50.0 μM, 40.0 μM, 30.0 μM, and 20.0 μM) in assay buffer were added before starting the fluorescence measurements. The kinetics (v) of fluorescence changes were measured at excitation and emission wavelengths of 320 nm and 405 nm for 30 min (1.44 min intervals, sensitivity 100, shaking intensity 4, duration 30 s) by a fluorescent plate reader (BIO-TEK/

Synergy HT). The inhibition constants ($K_i$) of the inhibitor with MMPs were calculated from the mean velocity values using GraphPad Prism 6 by the equation:

$$v = \frac{V_{max}[S]}{K_m\left(1 + \frac{[I]}{K_i}\right) + [S]}$$

TABLE 2

$K_i$ values of (1), (17), (19) and (20)

| Compounds $K_i$ (nM) | rhMMP-2 | rhMMP-7 | rhMMP-9 | rhMMP-12 | rhMMP-13 |
|---|---|---|---|---|---|
| Compound 1 | 10.4 ± 0.0 | 33.2 ± 5.0 | 17.4 ± 2.1 | 2.2 ± 0.5 | 16.9 ± 2.7 |
| Compound 19 | 5.8 ± 0.4 | 17.1 ± 0.1 | 20.4 ± 2.0 | 1.0 ± 0.2 | 15.3 ± 5.4 |
| Compound 20* | 101.0 ± 12.2 | | 60.6 ± 11.0 | 1.7 ± 0.2 | |
| Compound 17* | 8.6 ± 1.3 | | 8.8 ± 0.8 | 2.1 ± 0.3 | |
| GM-6001 | 0.5 ± 0.1 | 0.4 ± 0.0 | 1.2 ± 0.0 | 0.57 ± 0.0 | 0.3 ± 0.0 |
| RP-805 precursor | 19.1 ± 3.1 | | 19.2 ± 3.8 | 4.6 ± 0.5 | |

(*n > 3, mean ± SE)

Figure 2:
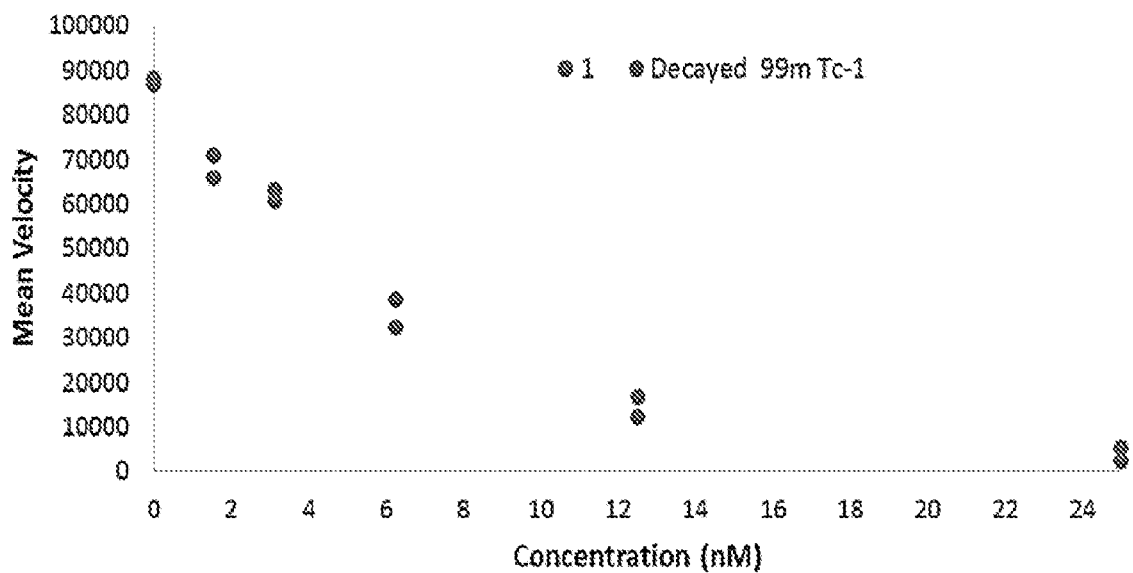
FIG. 2 illustrates a non-limiting effect of $^{99m}$Tc-labeling on recombinant MMP-12 (rhMMP-12) activity inhibition by 1.
Figure 3:
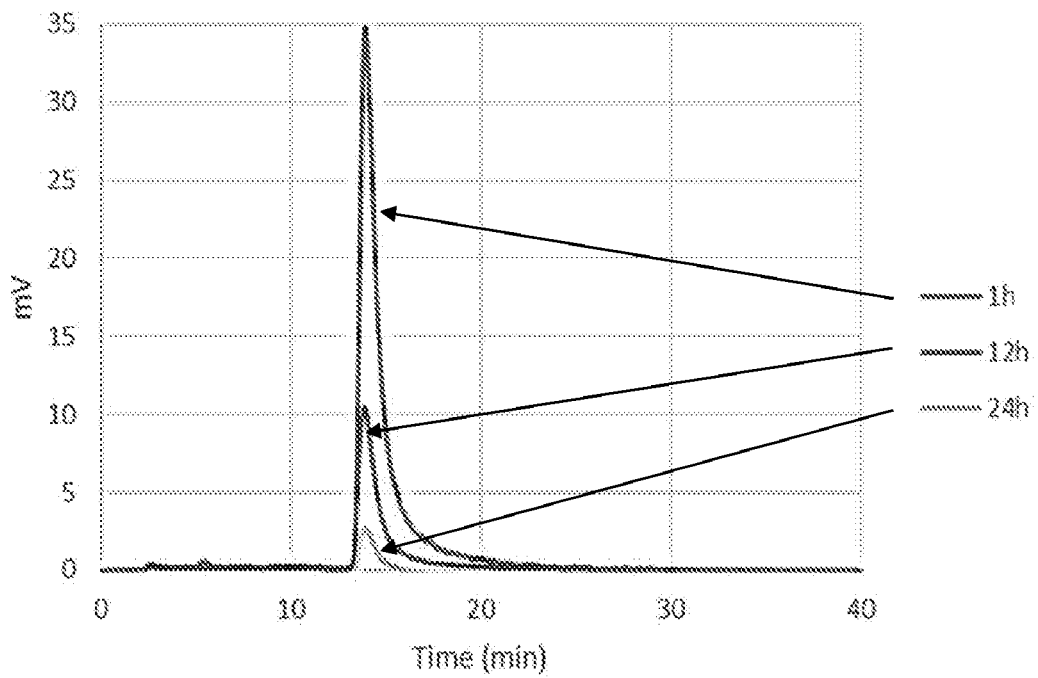
FIG. 3 illustrates a non-limiting radio-HPLC analysis of $^{99m}$Tc-1 and its stability in solution.

A similar protocol was used to check the effect of $^{99m}$Tc-labeling on MMP inhibition. A solution of $^{99m}$Tc-1 (250 μL) was prepared from 2 μg of 1 as described elsewhere herein. After two days at –80° C. for, the mixture was lyophilized and redissolved in saline buffer for MMP inhibition assays. The decayed $^{99m}$Tc-1 showed a similar inhibition tendency as the precursor 1 (FIG. 2), indicating that $^{99m}$Tc-labeling has no significant effect on MMP binding.

Accordingly, through in vitro binding screens, compounds of formulas I and II were shown exhibited strong binding to rhMMPs. Without wishing to be limited by any theory, changes to the length and characteristics of the groups distal to the hydroxamate group had very little effect on the binding of these compounds to MMP. Compounds with arginine groups, PEG groups or both arginine and PEG groups, bound MMP similarly well and they did not have significant effects on the compound's binding to the rhMMP catalytic domain.

Example 14: Hydrophilicity and Blood Clearance Comparisons

Matrix metalloproteinase-targeted imaging agents known in the art suffer from poor solubility of their precursors and have blood clearance times that make them ill-suited for practical application. The partition coefficient (Log D) values of $^{99m}$Tc-1 and $^{99m}$Tc-RP805 were determined based on their proportional distribution between n-octanol and water or Tris buffer at pH 7.4. As shown in Table 3, $^{99m}$Tc-1 had lower log D values and was more hydrophilic than $^{99m}$Tc-RP805, which characteristics were reported in WO2013070471A1 and US20150023873A1, which are incorporated herein in their entireties by reference. Compared with $^{99m}$Tc-RP805 and its precursor, the increased hydrophilicity of $^{99m}$Tc-1 (and 1) can in one aspect be ascribed to the introduction of arginine residue. The $^{99m}$Tc labeling compounds showed a little higher solubility in tris buffer at pH 7.4 than in water. $^{99m}$Tc-1 was analyzed for its degradation and stability by RP-HPLC, and showed good stability in saline at room temperature and in murine blood samples incubated at 37° C. for different times. HPLC analysis of urine samples collected after intravenous injection of $^{99m}$Tc-1 also showed its in vivo radiochemical stability in mice (FIG. 7).

Biodistribution study of $^{99m}$Tc-1 in mice showed faster blood clearance than $^{99m}$Tc-RP805, through a renal clearance pathway. $^{99m}$Tc-1 showed a lower residual blood activity at 1 and 2 h post injection compared to $^{99m}$Tc-RP805 (1.3±0.4 vs 2.8±1.2% injected dose (ID)/mL and 1.0±0.4 vs 1.8±0.7% ID/mL, respectively) and lower hepatobiliary excretion (bile: 1.5±0.3 vs 17.8±13.3% ID/g)]; both differences were statistically significant (FIG. 8).

TABLE 3

| Compound | Coligands | Two phases for partition | Log D |
|---|---|---|---|
| $^{99m}$Tc-RP805 | Tricine-TPPTS | Octanol/Tris (pH = 7.4) | –3.2 ± 0.1 |
| | | Octanol/water | –2.8 ± 0.0 |
| $^{99m}$Tc-1 | Tricine-TPPTS | Octanol/Tris (pH = 7.4) | –4.4 ± 0.1 |
| | | Octanol/water | –4.0 ± 0.1 |

Example 15: Imaging Tests Using Compounds of Formula I

Figures 4A, 4B, 4C, 4D:
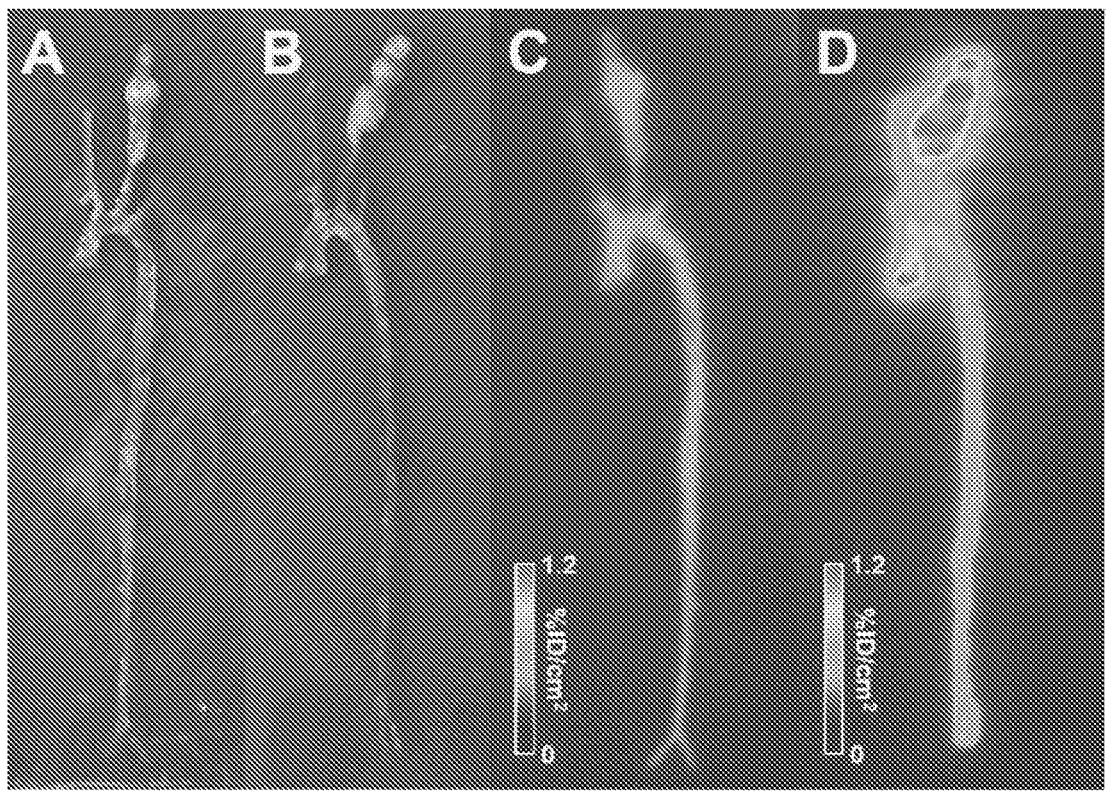
FIGS. 4A-4F illustrate $^{99m}$Tc-1 imaging of carotid aneurysm.
Figure 4E:
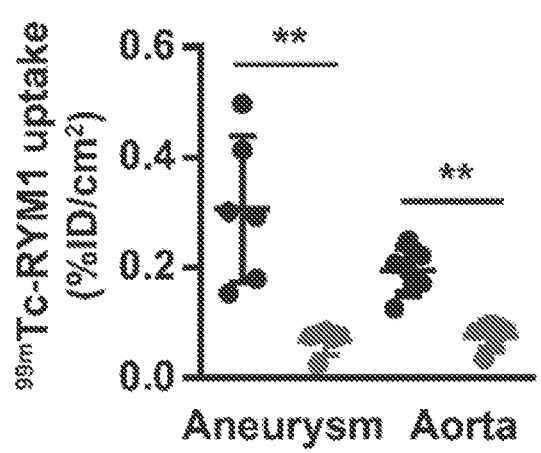
Figure 4F:
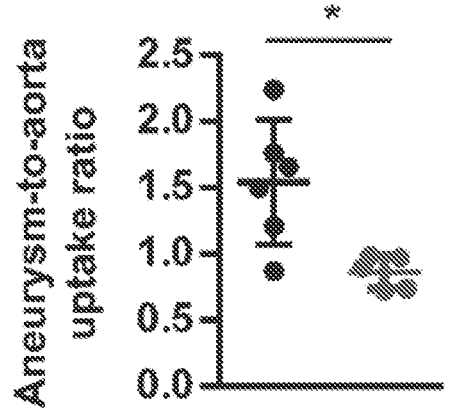

In vivo binding characteristics of $^{99m}$Tc-1 was addressed in murine models of carotid aneurysm and pulmonary arterial hypertension by autoradiography and in vivo SPECT/CT imaging followed by ex vivo planar imaging. Autoradiography, SPECT/CT and planar imaging studies indicated MMP specific binding of $^{99m}$Tc-1 in in vivo murine models of CaCl$_2$ induced carotid aneurysm and pulmonary arterial hypertension that express high levels of MMPs (FIGS. 4A-4E, 5-6). $^{99m}$Tc-1 uptake in carotid aneurysm mouse studies was specific as pre-injection of an excess of unlabeled 1 led to 46% signal reduction in aneurysm-to-aorta relative uptake (FIG. 4F).

Example 16

The present studies provide preclinical evaluation of an illustrative pan-MMP inhibitor-based radiotracer, $^{99m}$Tc-1, which was designed to address the shortcomings for clinical translation of other commonly used preclinical MMP-targeting SPECT tracers for cardiovascular applications. The data demonstrate high affinity of this novel tracer for a set of MMPs involved in aneurysm development, its good radiochemical stability, favorable properties for vascular imaging, and specific uptake in aneurysm in vivo that correlates with tissue MMP activity and inflammation.

Increased MMP activation is a key feature of aneurysm, and plays a central role in aortic remodeling. Accordingly, in vivo imaging of MMP activation can help predict the evolution of the disease and guide therapeutic decisions. The feasibility and potential value of in vivo MMP-targeted imaging in cardiovascular pathology has been shown in preclinical studies. Despite the wealth of the available preclinical data, a number of shortcomings, including a relatively slow blood clearance, can potentially limit clinical translation of $^{99m}$Tc-RP805 as an effective MMP tracer for cardiovascular applications. In addition, the limited aqueous solubility of RP805 precursor is a barrier to establishing uptake specificity in vivo. As such, only a few studies, mainly in vascular and valvular disease models, have attempted to demonstrate uptake specificity of this imaging agent in vivo.

As designed, 1 was found to have good aqueous solubility, even at relatively high concentrations needed for blocking studies. In addition, in comparison to $^{99m}$Tc-RP805, $^{99m}$Tc-1 showed a faster blood clearance, which facilitates early imaging and improves vessel wall-to-blood contrast in vivo. These favorable characteristics were empirically demonstrated in AAA microSPECT imaging studies, performed starting at 1 hour post-injection.

The optimal imaging time depends on many factors and for vascular imaging the vessel wall-to-blood ratio (contrast) is important. A longer tracer circulation time would increase tissue uptake, provided that the tracer has not reached a plateau or is increasingly retained, e.g., through internalization. Despite a lower blood level, $^{99m}$Tc-1 uptake in many organs was significantly higher than $^{99m}$Tc-RP805 (FIGS. 8A-8B) and the final activity in urine was lower. Without wishing to be limited by any theory, this latter point can in part be explained by a combination of high first-pass clearance, higher global tissue uptake, and random nature of urine samples. In vivo blocking studies (FIGS. 14A-14B) showed that the major component of tissue uptake is specific, reflecting a hitherto less recognized basal MMP activation in those tissues. This higher uptake, which indicates a higher sensitivity for the target, is not explained by differences in MMP affinity, as both tracers have comparable affinities toward MMPs, and in non-limiting embodiments can reflect better tissue penetration and easier accessibility to the target of $^{99m}$Tc-1. In contrast to many other tissues, there was a trend toward higher uptake of $^{99m}$Tc-RP805 compared to $^{99m}$Tc-1 in the normal aorta at 2 hours post-injection. This basal uptake in the normal vessel is a disadvantage for $^{99m}$Tc-RP805 and highlights the necessity of blocking studies with the non-labeled precursor to demonstrate specificity for any imaging application, whether vascular or not. In the absence of such blocking studies, it is impossible to ascertain the validity of the conclusions of any study. As alternative, other MMP inhibitors can be used in vivo to demonstrate signal specificity.

Figure 15:
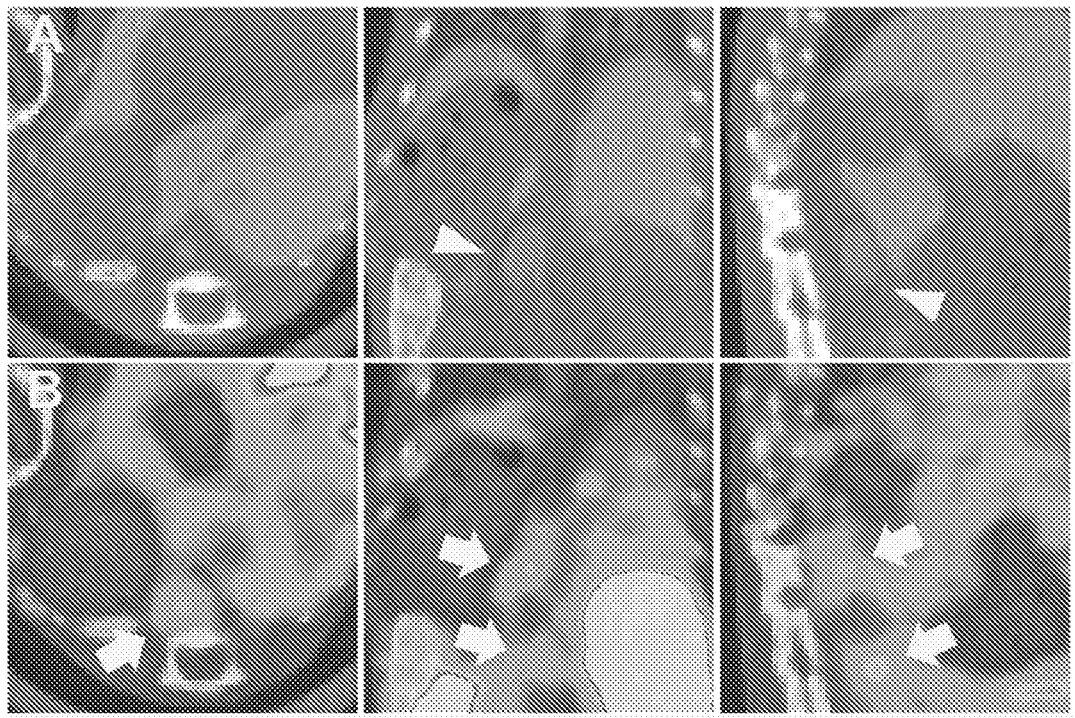
FIG. 15 illustrates $^{99m}$Tc-1 imaging of AAA. Examples of CT (A) and fused $^{99m}$Tc-1 SPECT/CT (B) images of an animal from the aneurysm group. Transversal (left), coronal (middle) and sagittal (right) views are shown. Arrows points to the area of maximal tracer uptake and arrowheads to the center of aneurysm on contrast-enhanced CT images. Scale: 0 to 1.5 counts per voxel per MBq.
Figure 16A:
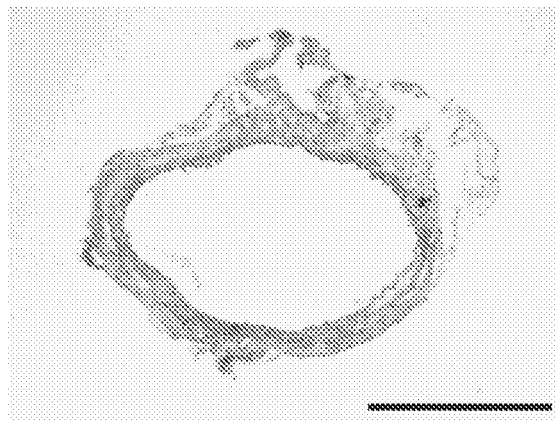
FIGS. 16A-16B illustrate representative examples of hematoxylin and eosin staining of suprarenal abdominal aortic sections in angiotensin II-infused apoE$^{-/-}$ mice with low aortic remodeling (FIG. 16A) or AAA (FIG. 16B). Scale bar: 500 µm.
Figure 16B:
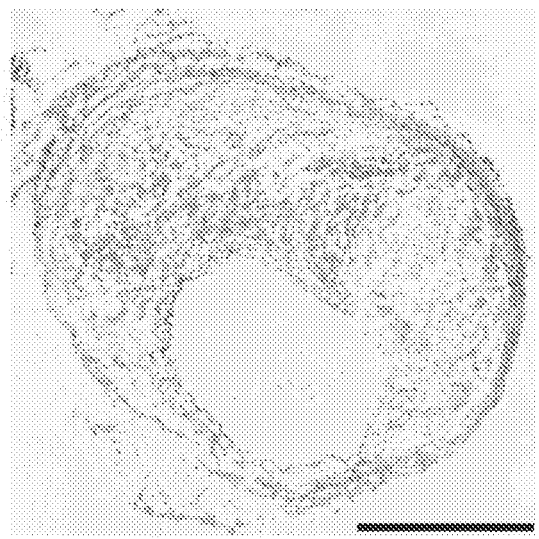

Evaluation of $^{99m}$Tc-1 in two preclinical models not only demonstrated the feasibility of in vivo imaging in aneurysm, but also provided complementary information regarding $^{99m}$Tc-1 uptake in aneurysm. Pre-injection of an excess of 1 in the carotid aneurysm model resulted in a significant decrease in $^{99m}$Tc-1 uptake in aneurysm, establishing uptake specificity of the tracer. Consistent with a certain level of basal MMP activation in the normal artery, this blocking also led to a reduction in aortic tracer uptake. The more prominent blocking effect in aneurysm, reflected in a reduced aneurysm-to-aorta uptake ratio under blocking conditions, mirrored the higher level of MMP activation in aneurysm. In Ang II-infused mice, animals that had developed aneurysm showed higher tracer uptake in suprarenal abdominal aorta. There was no correlation between aortic size and MMP signal in vivo, indicating that this enhanced uptake is not primarily related with aortic size. Of note, tracer uptake was often higher in aneurysm shoulders, at the border of areas of arterial enlargement (FIG. 15).

The heterogeneity of the response to Ang II infusion in apoE$^{-/-}$ mice was leveraged to investigate $^{99m}$Tc-1 uptake and its correlates in AAA. $^{99m}$Tc-1 signal was significantly higher in the AAA group and correlated well with aortic MMP activity detected by zymography ex vivo. Tissue MMP activity is tightly regulated at several levels, including MMP gene expression, MMP activation (through proteolytic cleavage of the pro-domain or allosteric activation), as well as the presence of endogenous inhibitors [e.g., tissue inhibitors of MMPs (TIMPs)]. A significant correlation was observed between in vivo aortic $^{99m}$Tc-1 signal with MMP-12 mRNA expression in Ang II-infused animals. Inflammatory cells are major sources of MMPs production, and protease activity is closely linked to tissue inflammation (e.g., link between macrophages and MMP-12 (macrophage elastase)). Strong correlations between aortic $^{99m}$Tc-1 signal, MMP activity and MMP-12 expression on one hand, and macrophage marker, CD68 expression on the other hand, were observed.

Qualitatively, while $^{99m}$Tc-1 and $^{99m}$Tc-RP805 share similar affinity profile to activated MMPs, higher uptake of $^{99m}$Tc-1 was observed in various tissues. This is apparent when comparing SPECT images with $^{99m}$Tc-1 to those obtained with $^{99m}$Tc-RP805 in a similar animal model (Golestani, et al., 2015, Circ. Cardiovasc Imaging 8:e002471). As shown by the blocking study, a large portion of this uptake is specific, and related to basal MMP activity.

In addition to AAA, dysregulated MMP activity is involved in other cardiovascular disorders, such as left ventricle remodeling post-myocardial infarction and atherosclerosis, as well as many primarily non-cardiovascular pathologies, including neurodegenerative diseases and cancer. Therefore, molecular imaging using compounds of the invention, such as but not limited to $^{99m}$Tc-1, can improve diagnosis and assessment of therapeutic response, and influence patient management in a wide range of applications. In clinical trials, several non-selective MMP inhibitors have shown adverse effects that preclude their use as therapeutic agents. In certain embodiments, evaluation of global proteolytic activity of MMPs, more integrative of different processes at play, is more informative, especially if the signal is stronger and less prone to background noise.

As demonstrated herein, in one aspect the compounds of the invention are MMP-targeted tracers, with favorable pharmacokinetics for early in vivo imaging. In vivo, the compounds' signal in aneurysm is specific and correlates with MMP activity and inflammation in murine AAA. Molecular imaging using compounds of the invention can improve patient management in AAA, as well as other disorders associated with dysregulated MMP activity.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound selected from the group consisting of:

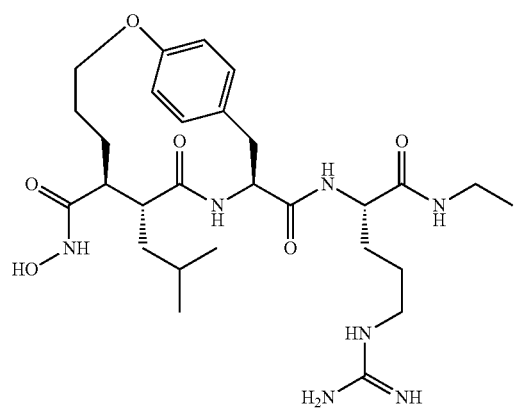

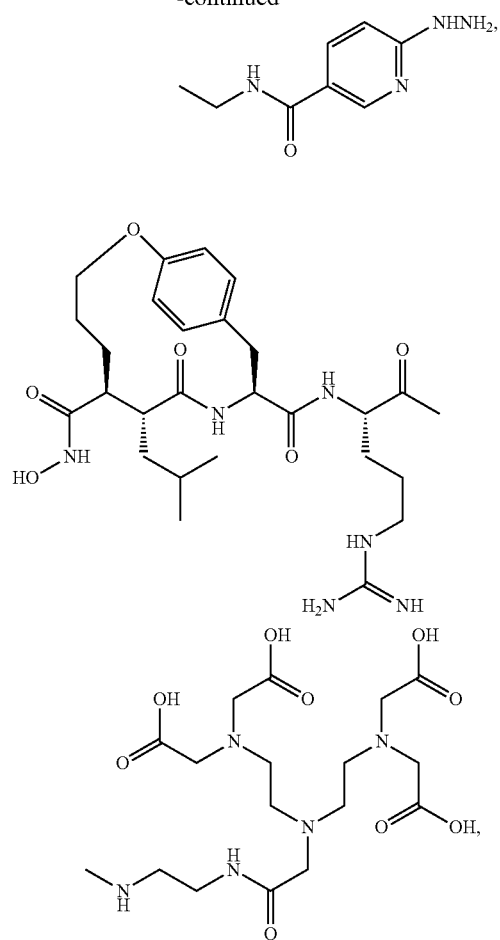
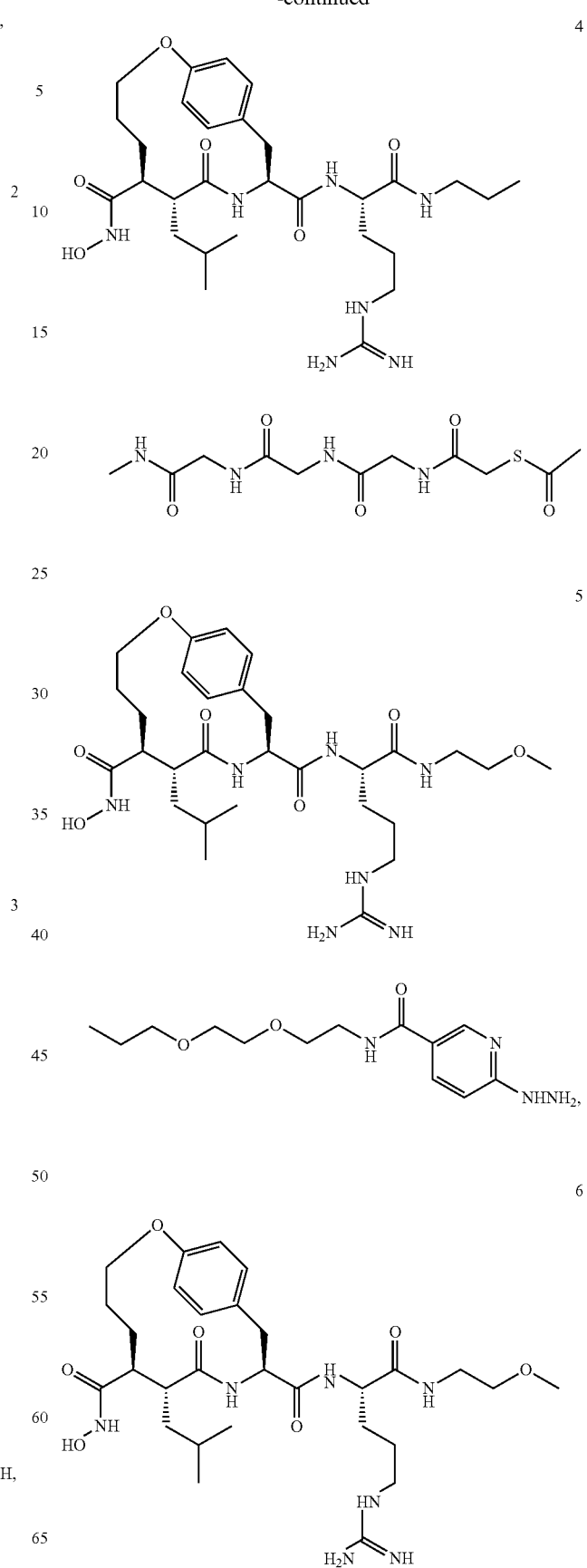

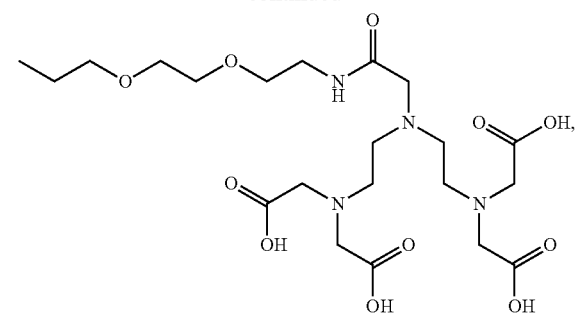
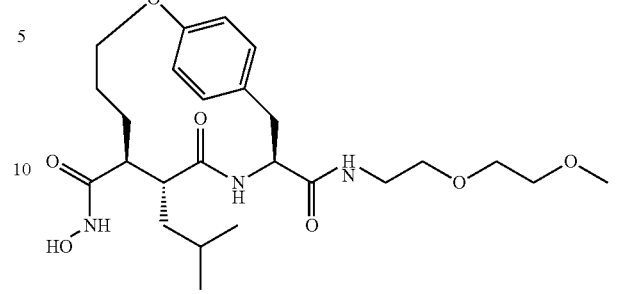
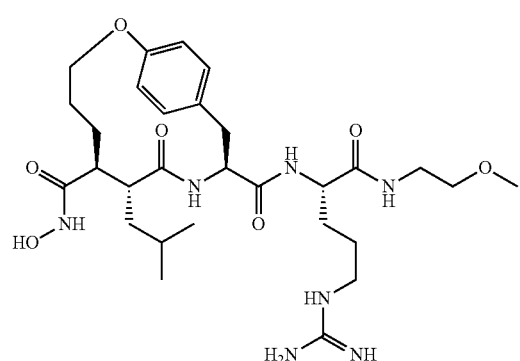
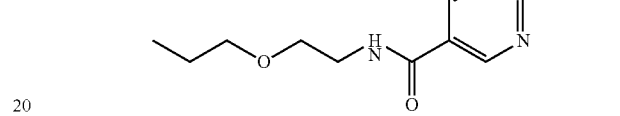
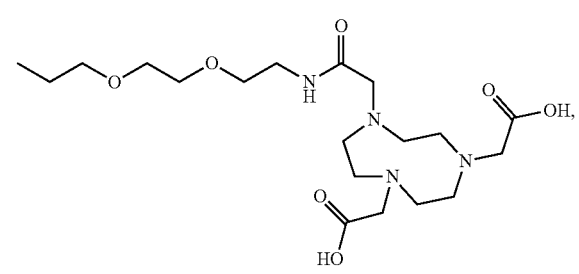
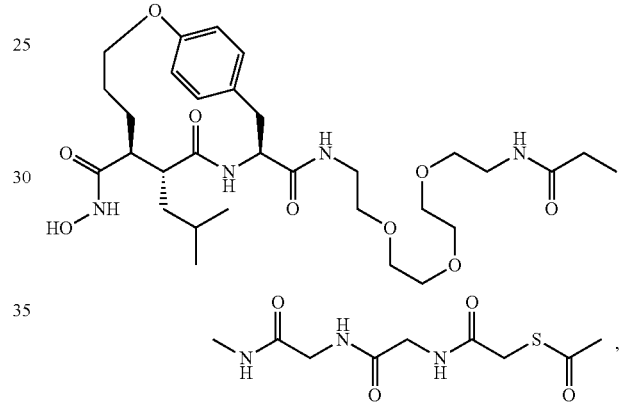
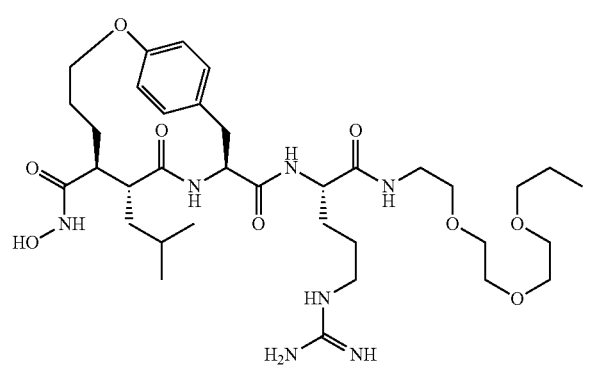
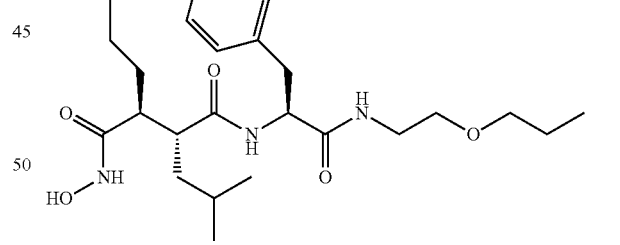
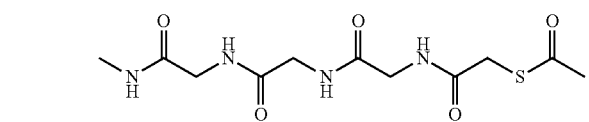
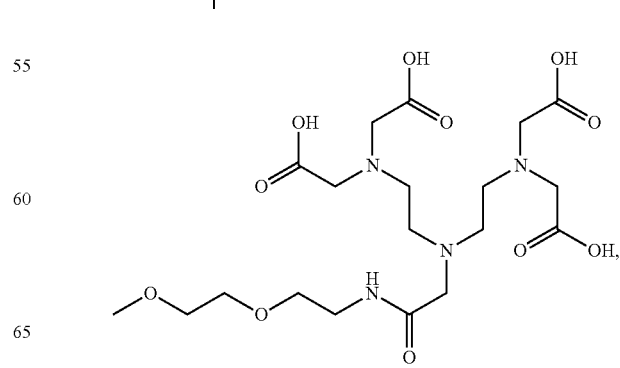

12
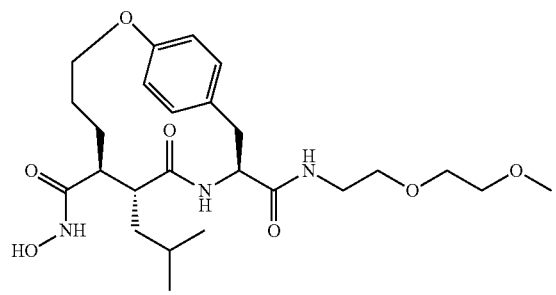
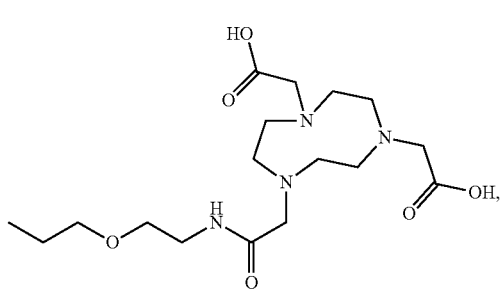
13
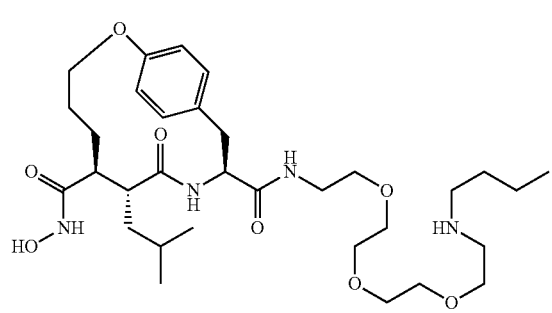
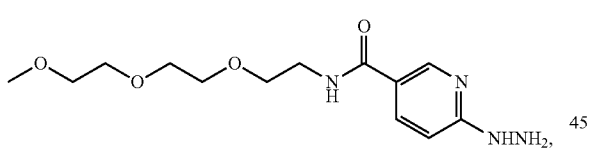
14
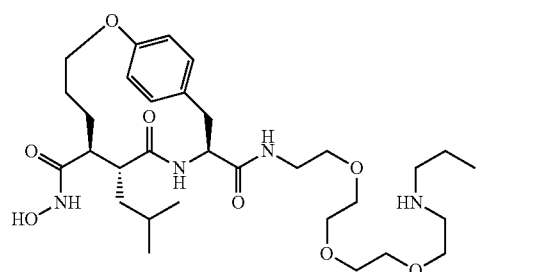
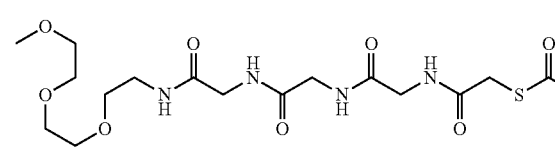
15
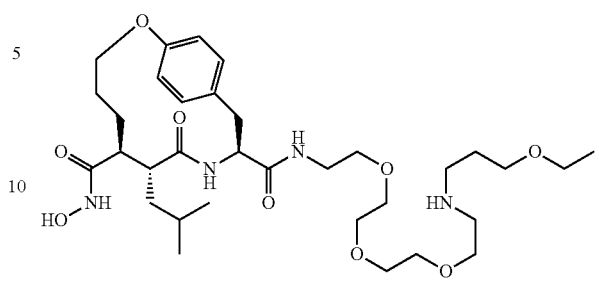
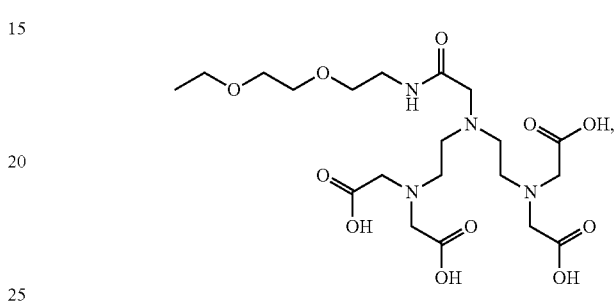
16
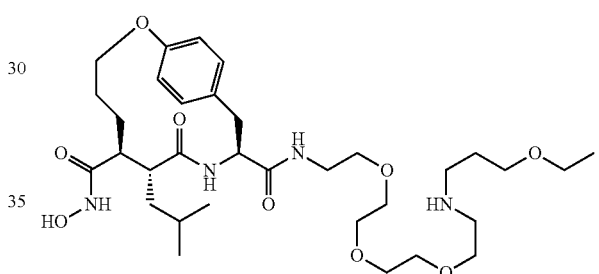
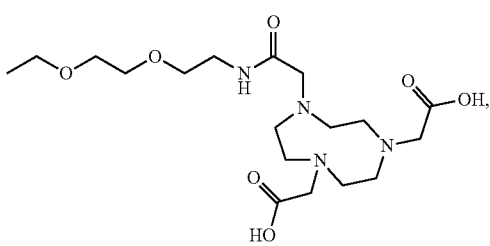
17
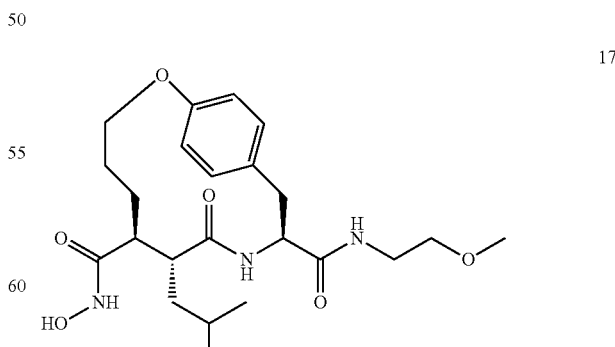
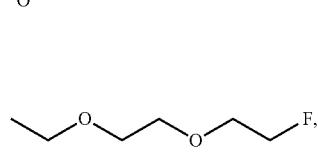

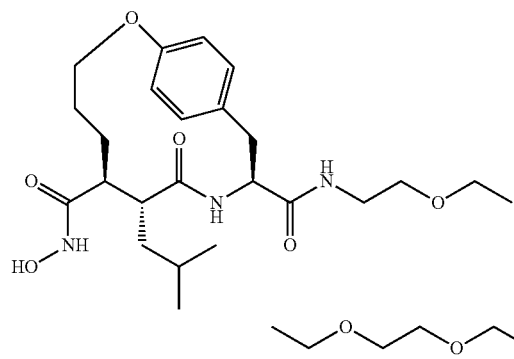

or a salt, solvate, stereoisomer, or tautomer thereof.

2. A compound of formula I, or a salt, solvate, stereoisomer, or tautomer thereof:

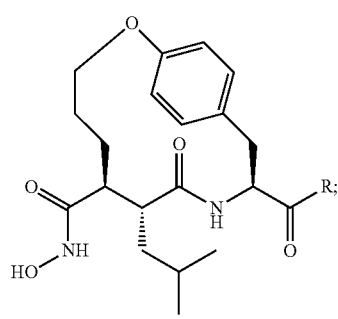

I wherein:
R is —NHR$^1$;
R$^1$ is selected from the group consisting of:

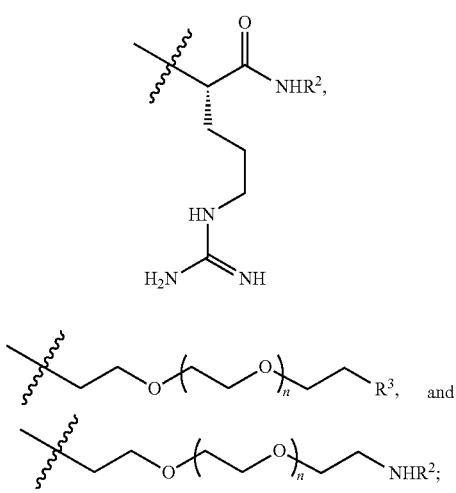

R$^2$ is selected from the group consisting of:

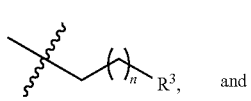

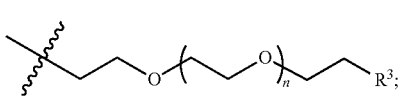

R$^3$ is selected from the group consisting of

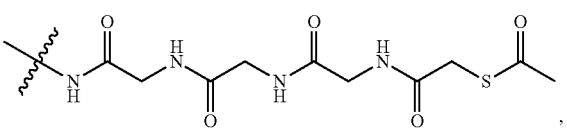

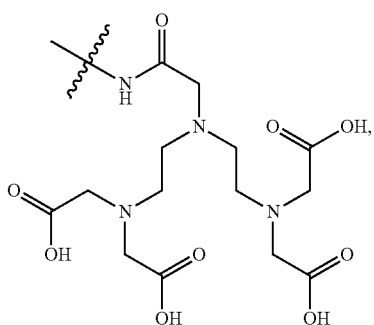

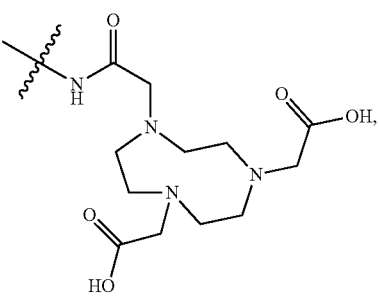

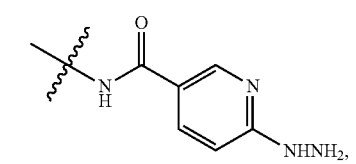

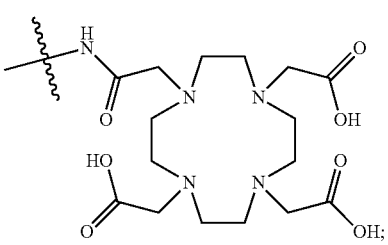

and each occurrence of n is independently an integer ranging from 0 to 30;

wherein the compound further comprises a radioisotope, which is bound to R$^3$. in its place.

3. The compound of claim 2, wherein the radioisotope is at least one selected from the group consisting of $^{99m}$Tc, $^{18}$F, $^{111}$In, $^{64}$Cu, and $^{68}$Ga.

4. The compound of claim 3, which is at least one selected from the group consisting of:
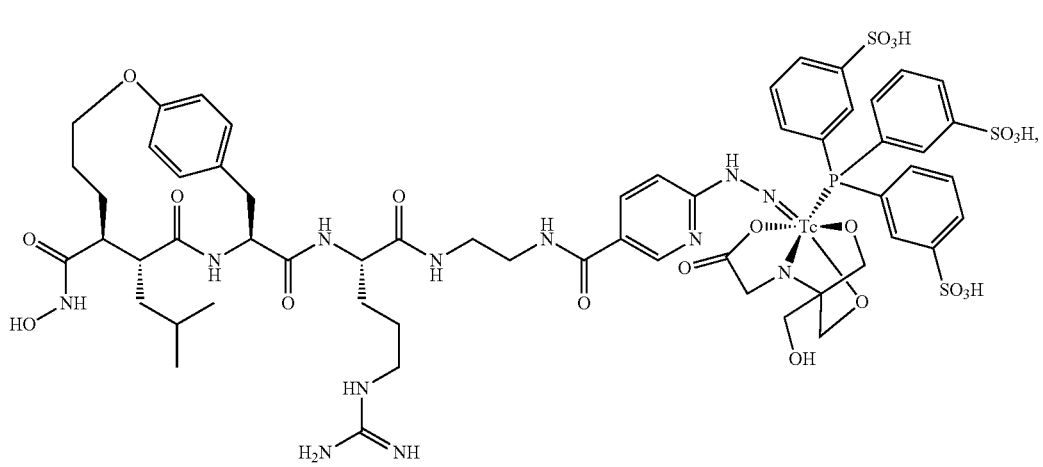
99mTc-1
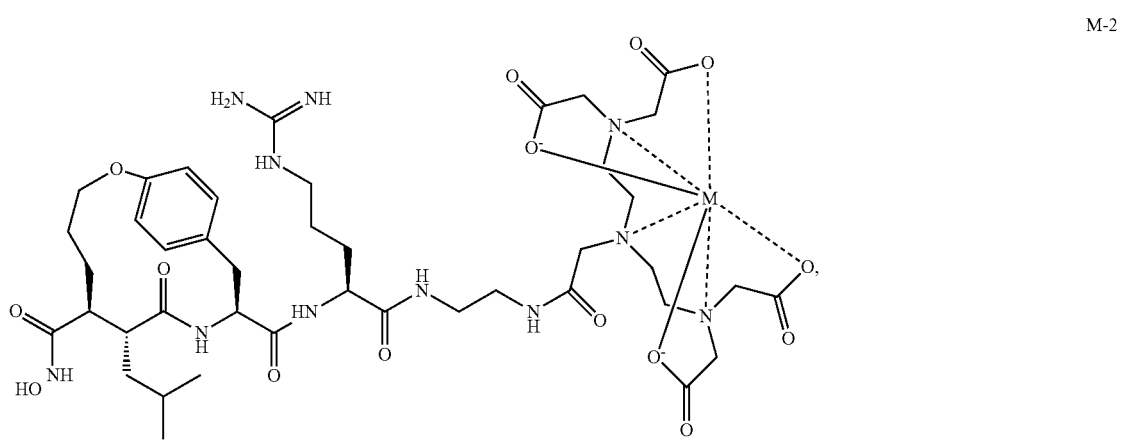
M-2
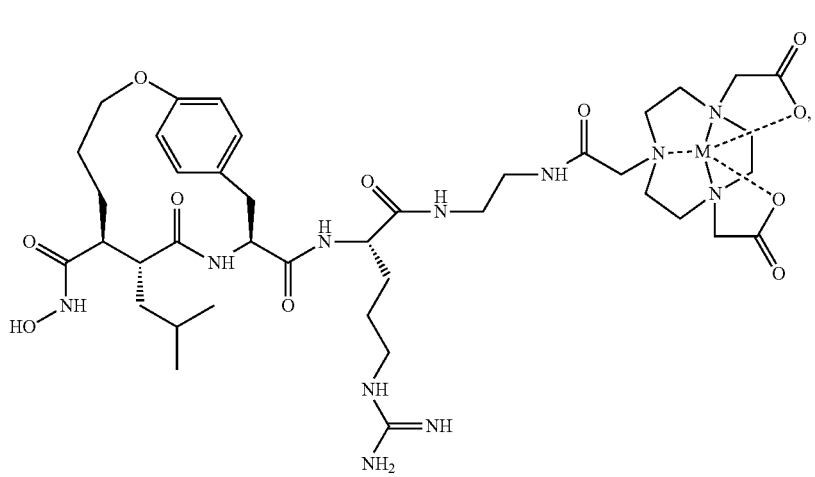
M-3
or a salt, solvate, stereoisomer, or tautomer thereof, wherein M is a metal.

5. A pharmaceutical composition comprising at least one compound of claim 2 and further comprising at least one pharmaceutically acceptable carrier.

6. A compound of formula II or a salt, solvate, stereoisomer, or tautomer thereof:

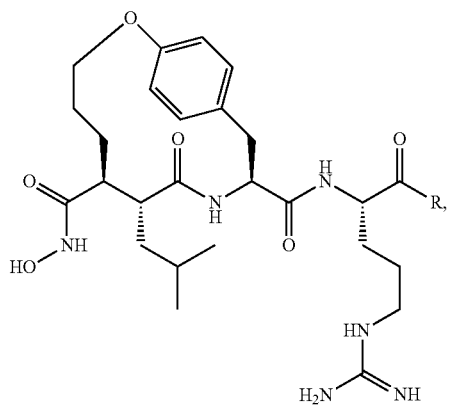

wherein:
R is selected from the group consisting of H, OH, alkoxy, cycloalkoxy, aroxy, heteroaroxy, SH, thioalkoxy, thiocycloalkoxy, —NH$_2$, —NHR', —NR'R', —NH(aryl), and —NH(heteroaryl); and
each occurrence of R' is independently selected from the group consisting of C$_1$-C$_6$ alkyl and C$_3$-C$_7$ cycloalkyl.

7. The compound of claim 6, which is selected from the group consisting of:

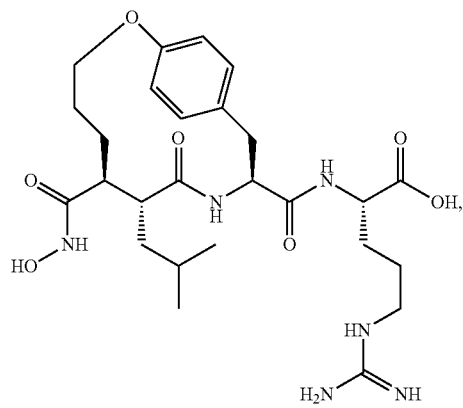

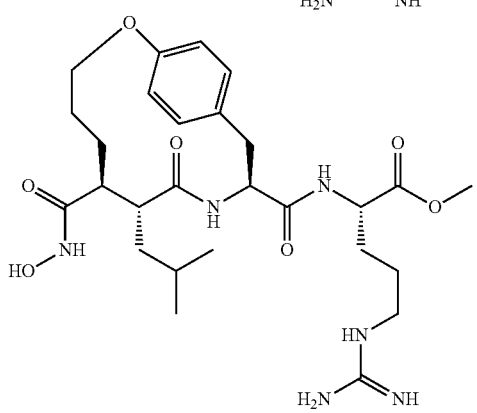

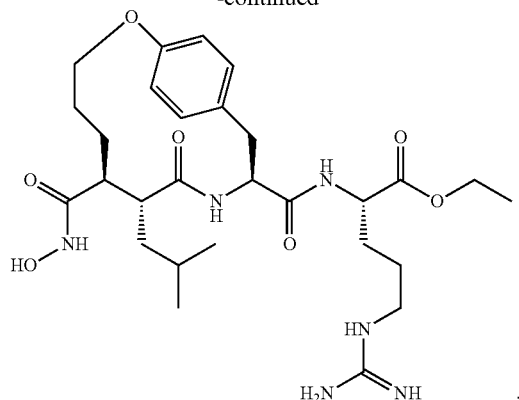

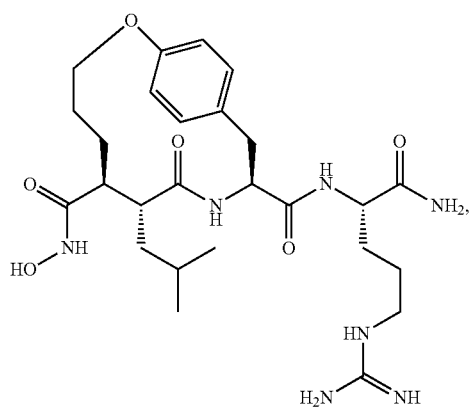

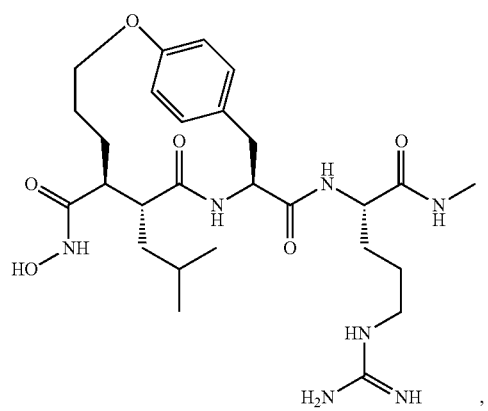

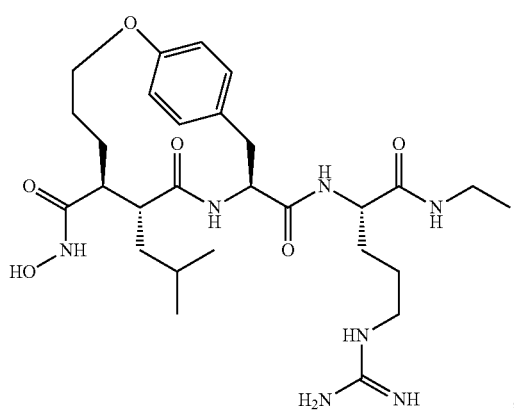

, and

-continued

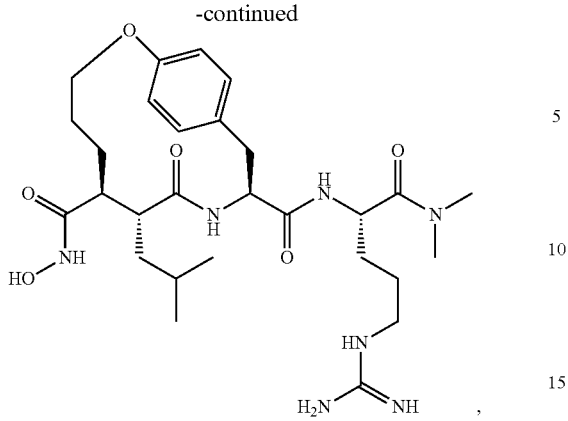

or a salt, solvate, stereoisomer, or tautomer thereof.

8. A pharmaceutical composition comprising at least one compound of claim 6 and further comprising at least one pharmaceutically acceptable carrier.

9. A kit comprising at least one compound of claim 2, an applicator, and instructions to use the at least one compound to evaluate a subject's risk of developing a cardiovascular disease or disorder or to treat a matrix metalloproteinase-related disease or disorder in a subject.

10. A kit comprising at least one compound of claim 6, an applicator, and instructions to use the at least one compound to evaluate a subject's risk of developing a cardiovascular disease or disorder or to treat a matrix metalloproteinase-related disease or disorder in a subject.

* * * * *

UNITED STATES PATENT AND TRADEMARK OFFICE
CERTIFICATE OF CORRECTION

| | | |
|---|---|---|
| PATENT NO. | : 11,286,251 B2 | Page 1 of 1 |
| APPLICATION NO. | : 16/088868 | |
| DATED | : March 29, 2022 | |
| INVENTOR(S) | : Sadeghi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 331 days.

Signed and Sealed this
Eleventh Day of February, 2025

Coke Morgan Stewart
*Acting Director of the United States Patent and Trademark Office*